United States Patent
Kikuchi et al.

(10) Patent No.: US 6,329,402 B1
(45) Date of Patent: Dec. 11, 2001

(54) HETEROCYCLE-CONTAINING CARBOXYLIC ACID DERIVATIVE AND DRUG CONTAINING THE SAME

(75) Inventors: Kouichi Kikuchi; Katsuya Tagami, both of Tsuchiura; Hiroyuki Yoshimura, Tsukuba; Shigeki Hibi, Tsukuba; Mitsuo Nagai, Tsukuba; Shinya Abe, Ushiku; Makoto Okita; Takayuki Hida, both of Tsukuba; Seiko Higashi, Nerima; Naoki Tokuhara, Tsukuba; Seiichi Kobayashi, Tsuchiura, all of (JP)

(73) Assignee: Eisai Co., Ltd., Tokyo (JP)

( * ) Notice: Subject to any disclaimer, the term of this patent is extended or adjusted under 35 U.S.C. 154(b) by 0 days.

(21) Appl. No.: 09/313,087

(22) Filed: May 17, 1999

Related U.S. Application Data

(62) Division of application No. 08/981,770, filed on Dec. 30, 1997, now Pat. No. 5,977,108.

(30) Foreign Application Priority Data

Jun. 30, 1995 (JP) .................................................. 7-166004
Jun. 4, 1996 (JP) .................................................. 8-141433
Jun. 27, 1996 (WO) ................................. PCT/JP96/01782

(51) Int. Cl.[7] .................. A61K 31/415; A61K 31/4155; A61K 31/4439; C07D 401/14; C07D 403/04

(52) U.S. Cl. ...................... 514/341; 514/406; 546/275.4; 546/276.4; 548/364.1; 548/365.7; 548/374.1; 548/373.1

(58) Field of Search ............................... 546/276.4, 275.4; 548/364.1, 374.1, 365.7; 514/341, 406

(56) References Cited

U.S. PATENT DOCUMENTS

| | | | |
|---|---|---|---|
| 4,612,321 | 9/1986 | Terao et al. | 514/338 |
| 4,703,110 | 10/1987 | Shudo | 534/566 |
| 5,420,145 | 5/1995 | Shudo | 514/352 |
| 5,420,273 | 5/1995 | Klaus et al. | 544/148 |
| 5,668,175 | 9/1997 | Evans et al. | 514/569 |

FOREIGN PATENT DOCUMENTS

| | | |
|---|---|---|
| 58-219162 | 12/1983 | (JP) . |
| 59-139379 | 8/1984 | (JP) . |
| 59-157044 | 9/1984 | (JP) . |
| 60-58981 | 4/1985 | (JP) . |
| 62-030172 * | 9/1987 | (JP) . |
| 62-256831 | 11/1987 | (JP) . |
| 63-54369 | 3/1988 | (JP) . |
| 63-1194525 | 5/1988 | (JP) . |
| 97/24116 | 7/1997 | (WO) . |

OTHER PUBLICATIONS

Khim. —Farm. Zh. 12(7), (1978), p. 71–77 Oleinik, A.F. et al "Synthesis and antileishmaniasis activity of arylfurylquinoxalines".
Chemical Abstract, 88 (23) (1978) p. 513 Szucs Ladislav et al "derivatives of alpha.–and beta.–unsaturated ketones derived from acetylpyridine. VIII. Spectral properties of some pyridine analogs of 1,3,5–triphenyl–2–pyrazoline" & Acta Fac. Pharm. Univ. comenianae, 30 (1977), p. 127–146, 88:169217.
Chemical Abstract, 74 (21), (1971) p. 125, Iyer, K.S. N. et al "p–aminosalicylic acid derivatives as possible tuberculostats" & Indian J. Chem., 8 (11), (1970), p. 964–968, 74:108600.
Heterocycles, 35(2) 1993 p. 975–995, Harry H. Wasserman et al "Synthesis and characterization of pyrrolinonecaroxylates formed by reaction of vivinal tricarbonyl derivatives with aldehyde schiff bases".
J. Med. Chem., 11(2), (1968), p. 295–300, G. J. Atwell et al., "Potential antitumor agents".
J. Org. Chem., 60(25), (1925), p. 8231–5, Wasserman et al "Selective Oxidation of phosphorus ylides by dimethyldioxirane Application to the formation of Vicinal Tricarbonyls".
Akiyama et al., Chemical Abstracts, 126:89368, 1997.*
Omran et al., Chemical Abstracts, 108:131443, 1988.*
Daidone et al., J. Heterocyclic Chem., 19(3), 689–690, 1982.*
Harhash et al., Tetrahedron, 31(1), 25–29, 1975.*
Parlow et al., J. Org. Chem., 62(17), 5908–5919, 1997.*
Sugiura et al., J. Med. Chem., 20(1), 80–85, 1977.*

* cited by examiner

*Primary Examiner*—Fiona T. Powers
(74) *Attorney, Agent, or Firm*—Nixon & Vanderhye

(57) ABSTRACT

Described is a heterocycle-containing carboxylic acid derivative represented by the following formula (I):

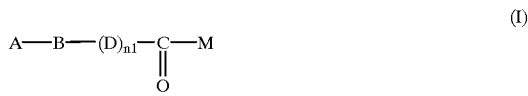

wherein A represents, for example, a heteroaryl group which contains at least one nitrogen atom and may have a substituent, B represents, for example, a heteroarylene group, a —CONH— group or a group represented by the formula —$CR^6$=$CR^7$— in which $R^6$ and $R^7$ represents H, a lower alkyl group or the like, D represents an arylene group, a heteroarylene group or the like, n1 stands for 0 or 1, M represents, for example, a hydroxyl group or a lower alkoxy group; or a physiologically acceptable salt thereof. As a retinoic-related compound replacing retinoic acid, it permits the provision of a preventive and/or therapeutic for various diseases.

6 Claims, No Drawings

HETEROCYCLE-CONTAINING CARBOXYLIC ACID DERIVATIVE AND DRUG CONTAINING THE SAME

This application is a division of application Ser. No. 08/981,770, filed Dec. 30, 1997, now U.S. Pat. No. 5,977,108.

TECHNICAL FIELD

The present invention relates to a heterocycle-containing carboxylic acid derivative and a drug containing said derivative.

BACKGROUND ART

Retinoic acid is an essential substance for the growth or life support of mammals including humans. It is known to have various effects, for example, upon ontogenesis, it serves as a morphogenetic factor, while in the adult body, it has effects on the differentiation and proliferation of cells. Described specifically, it is known to take part in the keratinization reaction, hair formation, sebaceous gland function or the like in the epidermis; the metabolism of bone or cartilage in the connective tissue; immunnomodulatory in the immune system; differentiation of neurocytes in the nerve system; differentiation and proliferation hemocytes in the blood system; and lipid metabolism, mineral metabolism and basal metabolism. A wide variety of physiological effects of retinoic acid as exemplified above are exhibited by its various control mechanisms such as expression regulation of a transcription activator through an intranuclear retinoid receptor (RARs, RXRs) family, regulation of the hormone secretion or function at the target organ, regulation of growth factors such as EGF receptor or TGFα, expression regulation of enzymes such as collagenase, tissue plasminogen activator or tyrosine kinase, and production regulation of cytokinesuich as IL-6.

In recent years, the relationship between these physiological effects of retinoic acid and various morbid conditions has come to be apparent. Particularly in some cancers typified by acute myelocytic leukemia, differentiation and induction treatment by using all-trans retinoic acid has drawn attentions as a novel therapeutic method of these cancers.

Retinoic acid, however, is found to involve various problems such as appearance of resistance caused by induction of P450 and expression of side effects due to its accumulation. Under such situations, there is accordingly a strong demand for the development of a novel retinoid-related compound, instead of retinoic acid, as a preventive and/or therapeutic for various diseases.

SUMMARY OF THE INVENTION

The present invention provides a heterocycle-containing derivative represented by the following formula (I):

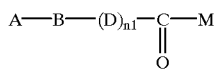

(I)

wherein:

A is a group represented by the following formula (i), (ii), (iii) or (iv):

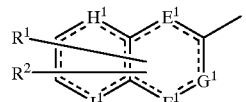

(i)

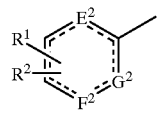

(ii)

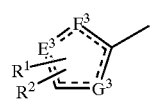

(iii)

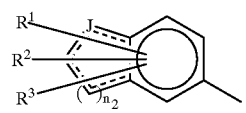

(iv)

in which $E^1$, $F^1$, $G^1$, $H^1$, $I^1$, $E^2$, $F^2$, $G^2$, $E^3$, $F^3$ and $G^3$ are the same or different and each independently represents an oxygen atom or a. nitrogen, carbon or sulfur atom which may have a substituent; J represents a nitrogen atom which may have a substituent, with the proviso that the cases where in the ring (i), $E^1$, $F^1$, $G^1$, $H^1$ and $I^1$ each represents a carbon group which may have a substituent, where in the ring (ii), $E^2$, $F^2$ and $G^2$ each represents a carbon-group which may have a substituent, and where in the ring (iii), $E^3$, $F^3$ and $G^2$ each represents a carbon group which may have a substituent are excluded; $R^1$, $R^2$ and $R^3$ are the same or different and each independently represents a hydrogen atom, a halogen atom., a lower alkyl group which may have a substituent, a cycloalkyl group which may have a substituent, a lower alkoxy group which may have a substituent, a cycloalkyloxy group which may have a substituent, an aryl group which may have a substituent, a heteroaryl group which may have a substituent, an aryloxy group which may have a substituent, a heteroaryloxy group which may have a substituent, a cycloalkylalkyl group which may have a substituent, an arylalkyl group which may have a substituent, a heteroarylalkyl group which may have a substituent, a cycloalkylalkyloxy group which may have a substituent, an arylalkyloxy group which may have a substituent, a heteroarylalkyloxy group which may have a substituent, an alkrenyl group which may have a substituent or an alkynyl group which may have a substituent, or $R^1$ and $R^2$ are coupled together to form a cycloalkylene group which may have a substituent, a carbon group forming said cycloalkylene group may be substituted by a sulfur atom, an oxygen atom, a sulfinyl group, a sulfonyl group or >$NR^4$, $R^4$ representing a hydrogen atom or a lower alkyl group, and $n_2$ stands for 1 to 3;

B is a heteroarylene group which may have a substituent, an arylene group which may have a substituent, or a group represented by the following formula:

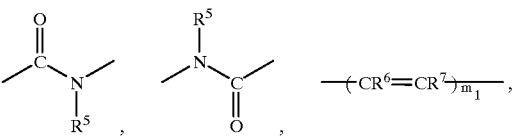

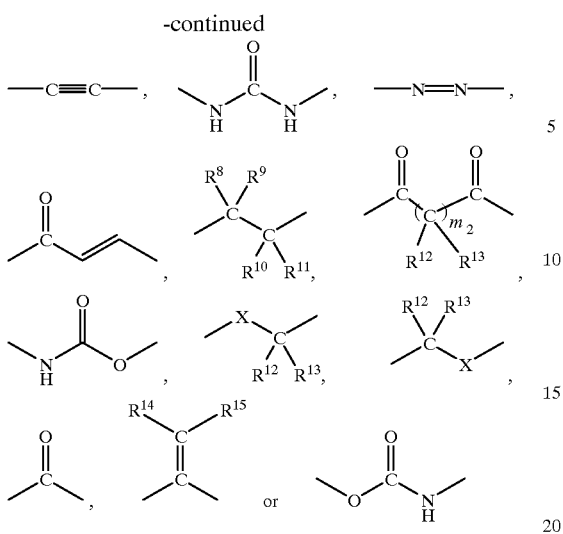

wherein $R^5$ represents a hydrogen atom or a lower alkyl group; $R^6$ and $R^7$ are the same or different and each independently represents a hydrogen atom, a lower alkyl group or a halogen atom and $m_1$ stands for 1 to 3, $m_2$ stands for 0 to 2; $R^8$ to $R^{15}$ are the same or different and each independently represents a hydrogen atom or a lower alkyl group; X represents an oxygen atom, a sulfur atom or $>NR^4$, $R^4$ having the same meaning as defined above;

D is an arylene group which may have a substituent, a heteroarylene group which may have a substituent, or a group represented by the formula: $-CR^6=CR^7-$, $R^6$ and $R^7$ having the same meanings as defined above;

$n_1$ stands for 0 or 1;

M is a hydroxyl group, a lower alkoxy group or a group represented by the following formula: $-NR^{16}R^{17}$ in which $R^{16}$ and $R^{17}$ are the same or different and each independently represents a hydrogen atom, a hydroxyl group, a lower alkyl group, a lower alkoxy group, a hydroxyalkyl group, an aryl group or a heteroaryl group or $R^{16}$ and $R^{17}$ are coupled together with the adjacent nitrogen atom to form an oxygen- or sulfur-containing ring; and ═══ represents a single bond or double bond; or a physiologically acceptable salt thereof.

In the definition of the formula (I), examples of the group represented by A include:

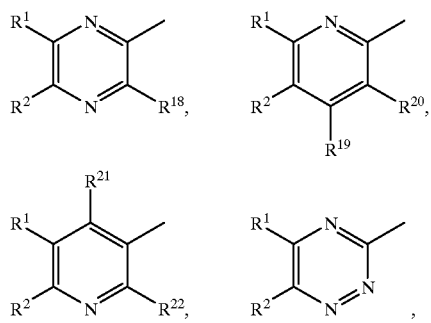

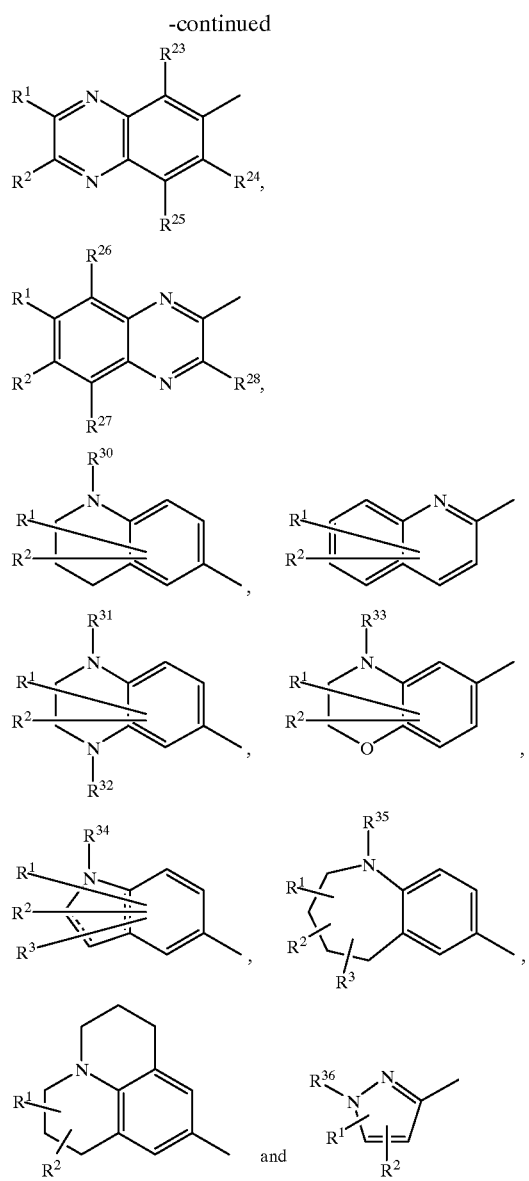

wherein $R^1$ and $R^2$ have the same meanings as defined above; $R^{18}$ to $R^{36}$ are the same or different and each independently represents a hydrogen atom, a lower alkyl group or a phenyl group. Among them, preferred are the groups represented by the following formulae:

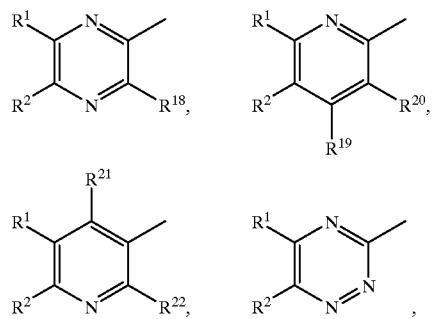

-continued

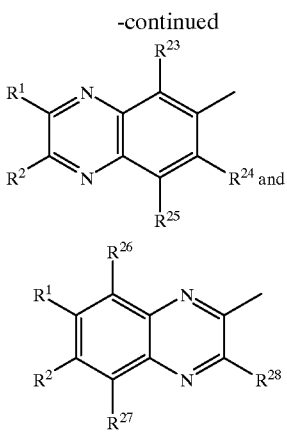

wherein $R^1$ and $R^2$ and $R^{18}$ to $R^{28}$ have the same meanings as defined above.

Preferred examples of the group represented by B include heteroarylene groups each of which may have a substituent, groups represented by the formula: —CONH— or groups represented by the formula: —$CR^6$=$CR^7$— in which $R^6$ and $R^7$ have the same meanings as defined above.

In the above definition, B embraces the group represented by the following formula:

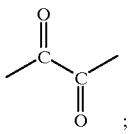

D embraces the group represented by the formula —$(CR^6$=$CR^7)m_1$— in which $R^6$, $R^7$ and $m_1$ have the same meanings as defined above; and A embraces the groups represented by the following formulae:

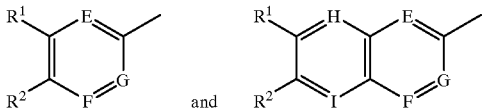

wherein $R^1$ and $R^2$ have the same meanings as defined above, and E, F, G, H and I are the same or different and each independently represents a nitrogen or carbon atom which may have a substituent and at least one of E, F, G, H and I represents a nitrogen atom.

The halogen atom represented by $R^1$, $R^2$, $R^3$, $R^6$ or $R^7$ in the definition of the formula (I) means a fluorine, chlorine, bromine or iodine atom. Examples of the lower alkyl group which is represented by $R^1$ to $R^3$ and may have a substituent include linear or branched $C_{1-6}$ alkyl groups such as methyl, ethyl, propyl, isopropyl, butyl, isobutyl, sec-butyl, tert-butyl, am-yl, isopentyl and neopentyl groups. Examples of the substituent which the lower alkyl group may have include a halogen atom, a lower alkoxy group, a cycloalkyl group, an alkenyl group, an alkynyl group, an aryl group, a heteroaryl group, an arylalkyl group, a heteroarylalkyl group and —$NR^{40}R^{41}$ in which $R^{40}$ and $R^{41}$ are the same or different and each independently represents a hydrogen atom, a lower alkyl group or a lower alkoxy group. Among them, methyl, ethyl, propyl and isopropyl groups are preferred. The lower alkyl group represented by $R^4$ to $R^3$ $^6$means any one of the above-exemplified lower alkyl groups.

Examples of the cycloalkyl group which is represented by $R^1$ to $R^3$ and may have a substituent include cyclopropyl, cyclobutyl, cyclopentyl, cyclohexyl and cycloheptyl groups which may have a substituent. Examples of the substituent which the cycloalkyl group may have include a lower alkyl group, a halogen atom, a lower alkoxy group, a cycloalkyl group, an alkenyl group, an alkynyl group, an aryl group, a heteroaryl group, an arylalkyl group, a heteroarylalkyl group and —$NR^{40}R^{41}$ in which $R^{40}$ and $R^{41}$ have the same meanings as defined above. Among them, a lower alkyl group such as methyl, ethyl and isopropyl, a lower alkoxy, group such as methoxy and ethoxy and halogen atoms such as fluorine acid chlorine are preferred.

Examples of the lower alkoxy group which is represented by $R^1$ to $R^3$ and may contain a substituent include linear or branched $C_{1-6}$ alkoxy groups such as methoxy, ethoxy, n-propoxy, isopropoxy and n-butoxy groups. These lower alkoxy groups may each contain any one of the above-exemplified substituents.

Examples of the cycloalkyloxy group which is represented by $R^1$ to $R^3$ and may contain a substituent include $C_{3-7}$ cycloalkyloxy groups such as cyclopropyloxy, cyclobutyloxy, cyclopentylpropyl, cyclohexyloxy and cycloheptyloxy. These cycloalkyloxy groups may each contain any one of the above-exemplified substituents.

Examples of the aryl group which is represented by $R^1$ to $R^3$ and may contain a substituent include phenyl, 1-naphthyl and 2-naphtyl groups. These aryl groups may each contain any one of the above-exemplified substituents.

Examples of the heteroaryl group which is represented by $R^1$ to $R^3$ and may contain a substituent include groups derived from a heterocyclic ring such as pyridyl, thiazole, oxazole, pyrimidyl, pyrrole, pyrazole, imidazole, furyl and thienyl. These heteroaryl groups may each contain any one of the above-exemplified substituents.

Examples of the aryloxy group which is represented by $R^1$ to $R^3$ and may contain a substituent include phenyloxy and naphthyloxy groups. These aryloxy groups may each contain any one of the above-exemplified substituents.

Examples of the heteroaryl oxy group which is represented by $R^1$ to $R^3$ and may contain a substituent include pyridyloxy, thiazolyloxy, oxazolyloxy, pyrimidyloxy, pyrroleoxy, pyrazolyloxy, imidazolyloxy, furyloxy and thienyloxy groups. These aryl groups may each contain any one of the above-exemplified substituents.

Examples of the cycloalkylalkyl group which is represented by $R^1$ to $R^3$ arid may contain a substituent include cyloalkylalkyl groups such as cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl and cycloheptylethyl. These cyloalkylalkyl groups may each contain any one of the above-exemplified substituents.

Examples of the arylalkyl group which is represented by $R^1$ to $R^3$ and may contain a substituent include phenylmethyl, phenylethyl, 1-naphthylmethyl, 1-naphthylethyl, 2-naphthylmethyl and 2-naphthylethyl groups. These arylalkyl groups may each contain any one of the above-exemplified substituents.

Examples of the heteroarylalkyl group which is represented by $R^1$ to $R^3$ and may contain a substituent include groups derived from a heterocyclic ring such as pyridylmethyl, pyridylethyl, thiazolylmethyl, thiazolylethyl, oxazolylmethyl, oxazolylethyl, pyrimidylmethyl, pyrimidylethyl, pyrrolemethyl, pyrroleethyl, pyrazolylmethyl, pyrazolylethyl, imidazolylmethyl, imidazolylethyl, furylmethyl, furylethyl, thienylmethyl and thienylethyl groups. These heteroarylalkyl groups m ay each contain any one of the above-exemplified substituents.

Examples of the cycloalkylalkyloxy group which is represented by $R^1$ to $R^3$ and may contain a substituent include cyclopropylmethyloxy, cyclopropylethyloxy, cyclobutylmethyloxy, cyclobutylethyloxy, cyclopentylmethyloxy, cyclopentylethyloxy, cyclohexylmethyloxy, cyclohexylethyloxy, cycloheptylmethyloxy and cycloheptylethyloxy groups. These cycloalkylalkyloxy groups may each contain any one of the above-exemplified substituents.

Examples of the arylalkyloxy group which is represented by $R^1$ to $R^3$ and may contain a substituent include phenylmethyloxy, phenylethylcoxy, 1-naphthylmethyloxy, 1-naphthylethyloxy, 2-naphtylmethyloxy and 2-naphthylethyloxy groups. These arylalkyloxy groups may each contain any one of the above-exemplified substituents.

Examples of the heteroarylalkyloxy group which is represented by $R^1$ to $R^3$ and may contain a substituent include groups derived from a heterocyclic ring such as pyridylmethyloxy, pyridylethyloxy, thiazolylmethyloxy, thiazolylethyloxy, oxazolylmethyloxy, oxazolylethyloxy, pyrimidylmethyloxy, pyrimidylethyloxy, pyrrolemethyloxy, pyrroleethyloxy, pyrazolylmethyloxy, pyrazolylethyloxy, imidazolylmethyloxy, imidiazolylethyloxyv, furylmethyloxyv, furylethyloxy, thienylmethyloxy and thienylethyloxy groups. These heteroarylalkyloxy groups may each contain any one of the above-exemplified substituents.

Examples of the alkenyl group which is represented by $R^1$ to $R^3$ and may contain a substituent include linear or branched $C_{2-6}$ alkenyl groups, for example, those having a double bond such as ethenyl, propenyl, butenyl, pentenyl and hexenyl. These alkenyl groups may each contain any one of the above-exemplified substituents.

Examples of the alkynyl group which is represented by $R^1$ to $R^3$ and may contain a substituent include linear or branched $C_{2-6}$ alkynyl groups, for example, those having a triple bond such as ethynyl, propynyl, butynyl, pentynyl and hexynyl. These alkynyl groups may each contain any one of the above-exemplified substituents.

As the cycloalkylene group which is formed by $R^1$ and $R^2$ and may contain a substituent, 5 to 7-membered cycloalkylene groups are preferred. Specific examples include the following groups:

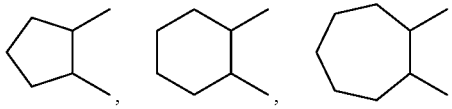

These cycloalkylene groups may each contain any one of the above-exemplified substituents.

The carbon atom forming the above-exemplified cycloalkylene group may be; substituted with a sulfur atom, an oxygen atom, a sulfinyl group, a sulfonyl group or >NR$^4$ in which $R^4$ has the same meaning as defined above. Specific examples include the following groups:

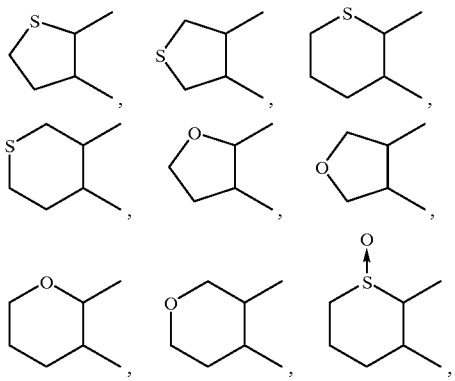

-continued

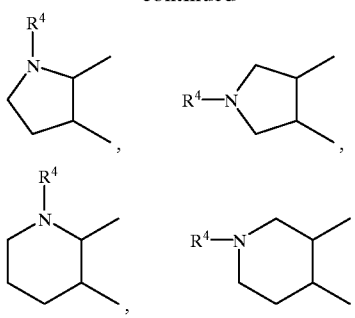

wherein $R^4$ has the same meaning as defined above.

The above heterocyclic rings may each contain a substituent, for example, a lower alkyl group such as methyl or ethyl, a halogen atom or a lower alkoxy group. In the definition of B or D, examples of the heteroarylene group which may contain a substituent include divalent groups derived from a heterocyclic ring such as pyridylene, thiazolene, oxazolene, pyrimidylene, pyrrolene, pyrazolene, imidazolene, furylene and thienylene group. These heteroarylene groups may each contain any one of the above-exemplified substituents.

In the definition of B or D, examples of the arylene group which may contain a substituent include phenylene and naphthylene groups. These arylene groups may each contain any one of the above-exemplified substituents.

As the lower alkoxy groups represented by M, $R^{16}$ or $R^{17}$, those defined in the above $R^1$ to $R^3$ can be used.

As the hydroxyalkyl groups represented by $R^{16}$ or $R^{17}$ the above-exemplified lower alkyl group, any one of carbon atoms of said lower alkyl group containing one to three hydroxyl groups, can be used. As the lower alkyl, aryl and heteroaryl groups, those exemplified above, respectively can be used.

In the definition of $R^{16}$ and $R^{17}$ or examples of the ring which is formed by $R^{16}$ and $R^{17}$ together with the adjacent nitrogen atom and may contain an oxygen atom or sulfur atom include the following rings.

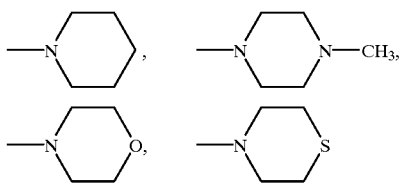

The term "physiologically acceptable salt" as used herein means a "conventionally used nontoxic salt". Examples include inorganic acid salts such as hydrochloride, hydrobromide, sulfate and phosphate; organic acid salts such as acetate, maleate, tartrate, methanesulfonate, benzenesulfonate and toluenesulfonate; and salts with an amino acid such as arginine, asparatic acid or glutamic acid. Metal salts of Na, K, Ca and Mg are also embraced by the physiologically acceptable salt of the present invention.

A description will next be made of the typical preparation processes of the invention compound.

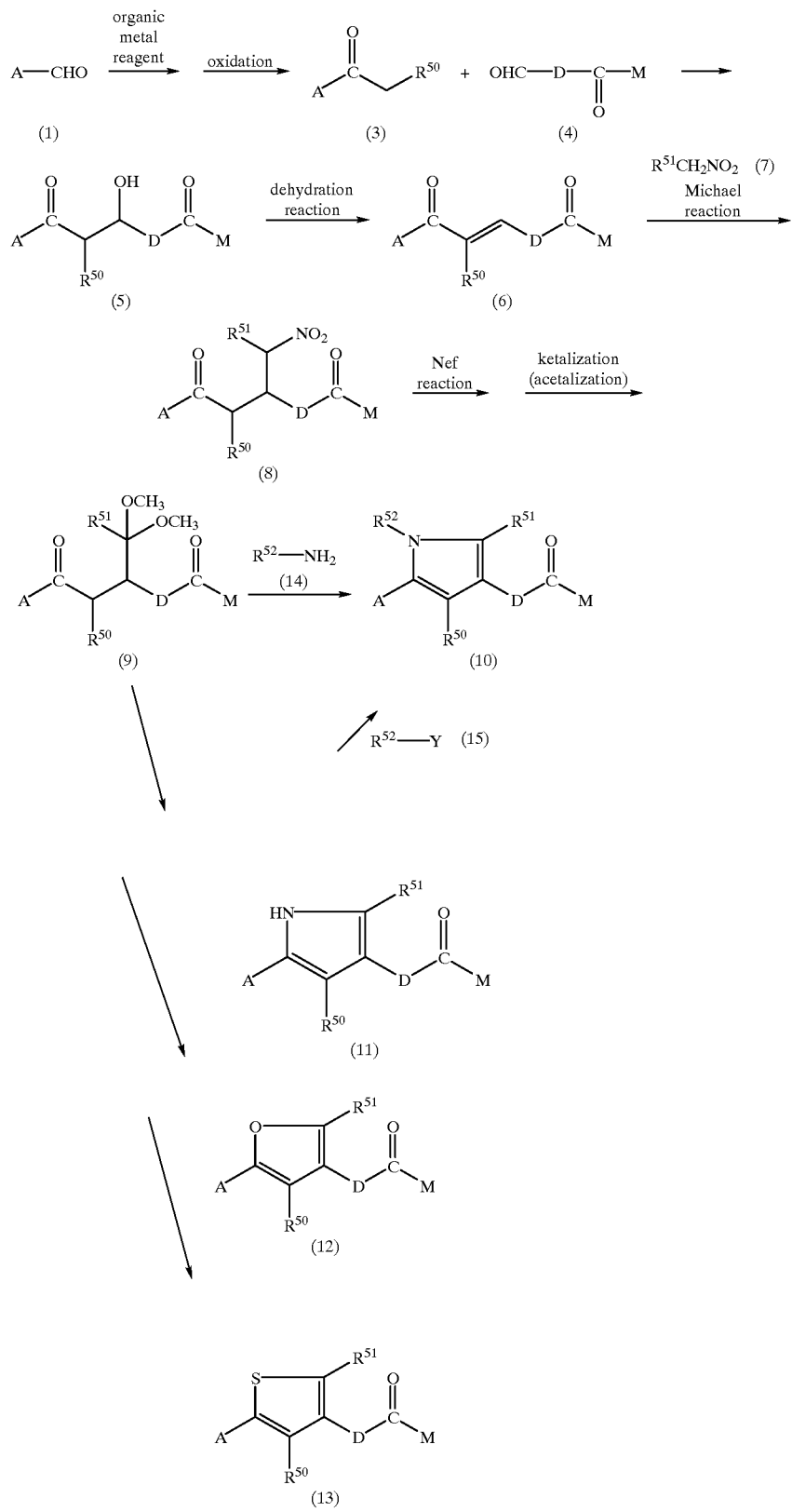

wherein A, D and M have the same meanings as defined above, $R^{50}$ and $R^{51}$ individually represent a hydrogen atom or a lower alkyl group, $R^{52}$ represents a hydrogen atom, a lower alkyl group, an alkenyl group, an alkynyl group, a cycloalkyl group, a cyclokalkylalkyl group, a lower alkoxyalkyl group, an aryl group, a heteroaryl group, an arylalkyl group or a heteroarylalkyl group and Y represents a halogen atom.

A compound of t he formula (3) can be obtained by reacting an aldehyde of the formula (1) with an organic metal reagent and then oxidizing the resulting alcohol derivative. As the organic metal reagent for obtaining the alcohol derivative, Grignard reagent, organic lithium reagent or the like can be used. As a solvent, hexane, diethyl ether, tetrahydrofuran or the like can be used. The reaction temperature falls within a range of from −78° C. to the boiling point of the solvent, with a range of from −78° C. to room temperature being preferred.

As the oxidation reaction, Swern oxidation, manganese dioxide oxidation or chromic acid oxidation can be employed.

A compound represented by the formula (5) can be obtained by reacting the ketone derivative (3) with an aldehyde of the formula (4) in the presence of a catalytic amount of a base and then subjecting the resulting alcohol derivative to dehydration reaction in the presence of an acid. Examples of the base for the preparation of the alcohol derivative include alkali hydroxides such as sodium hydroxide and potassium hydroxide. Examples of the solvent include methanol, ethanol, propanol, tetrahydrofuran and N,N-dimethylformamide. The reaction temperature falls within a range of from 0° C. to the boiling point of the solvent, with a range of from 20 to 40° C. being preferred.

Example of the acid used for the dehydration reaction include hydrochloric acid, sulfuric acid, p-toluenesulfonic acid, trifluoroacetic acid, oxalic acid and phosphoric acid. Exemplary solvents include ethers such as diethyl ether, teatrahydrofuran, 1,4-dioxane and 1,2-dimethoxyethane and aromatic hydrocarbons such as benzene, toluene and xyleane. The reaction is effected at 0° C. to the boiling point of the solvent. In some cases, Compound (6) can be obtained directly from Compound (5) without dehydration reaction.

Compound (6) can be introduced into Compound (8) by acting a catalytic amount of a base to Compound (6) with a nitro compound represented by the formula (7) as a solvent (in the case where the compound is sparingly soluble, tetrahydrofuran, methanol, ethanol or the like is added as needed). Exemplary bases include N-benzyltrimethylammonium hydroxide, triethylamine and diisopropylamine. The reaction is effected at a temperature range of from 0° C. to the boiling point of the solvent, with a temperature range of from 0° C. to room temperature being preferred.

Compound (9) can be obtained by subjecting Compound (8) successively to Nef reaction and ketalization. Ketalization is attained by the addition of a mineral acid such as sulfuric acid or hydrochloric, acid in methanol. The reaction temperature falls within a range of from −78° C. to the boiling point of the solvent, with a range of from −40° C. to room temperature being preferred.

A pyrrole derivative (10) can be obtained by acting a primary amine (14) to Compound (9). Any solvent can be used insofar as it is inert to the reaction. Preferred are aromatic hydrocarbon solvents such as benzene, toluene and xylene, ether solvents such as tetrahydrofuran and 1,2-dimethoxyethane and alcohol solvents such as methanol and ethanol. The reaction is allowed to proceed in the presence of an acid in the above-exemplified solvent. As the acid, that which also serves as a dehydrating agent, for example, hydrochloric acid, sulfuric acid, glacial acetic acid or polyphosphoric acid can be used. The reaction can also be effected by using an acid such as glacial acetic acid as a solvent.

When Compound (9) is reacted using an ammonium salt such as ammonium acetate, ammonium hydrochloride or ammonium sulfate in the presence of an acid, a pyrrole derivative (11) can be obtained. Compound (10) can be obtained by acting a halide (15) to Compound (11) in the presence of a base. Exemplary bases include alkali metal compound such as potassium carbonate, sodium hydride and potassium hydride and metal alkoxides such as sodium methoxide, sodium ethoxide and potassium-tert-butoxide. Examples of the solvent include N,N-dimethylformamide, tetrahydrofuran and 1,2-dimethoxyethane. The reaction temperature ranges from 0° C. to the boiling point of the solvent.

Compound (9) can be introduced into its furan derivative (12) by acting an acid on it. Illustrative acids include sulfuric acid and polyphosphoric acid. The reaction is effected at 0° C. to 100° C. Compound (9) can be introduced into a thiophene derivative (13) by acting, on Compound (9), a sulfide such as phosphorus pentasulfide or hydrogen sulfide. As the solvent, an aromatic hydrocarbon such as benzene, toluene or xylene or pyridine is used and the reaction is effected at a temperature range of from 0° C. to the boiling point of the solvent, preferably from 50° C. to the boiling point of the solvent.

Preparation Process 2

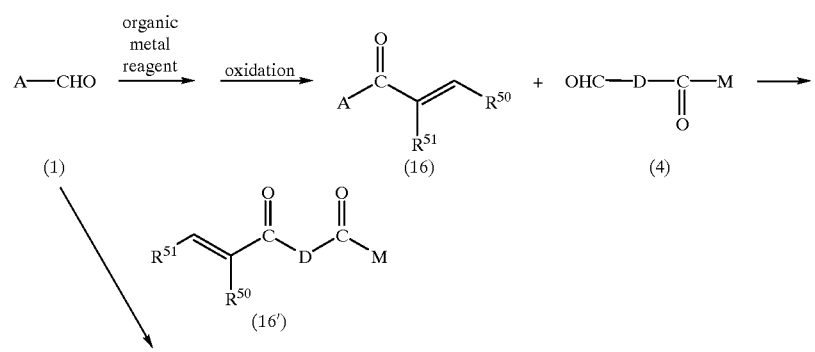

-continued

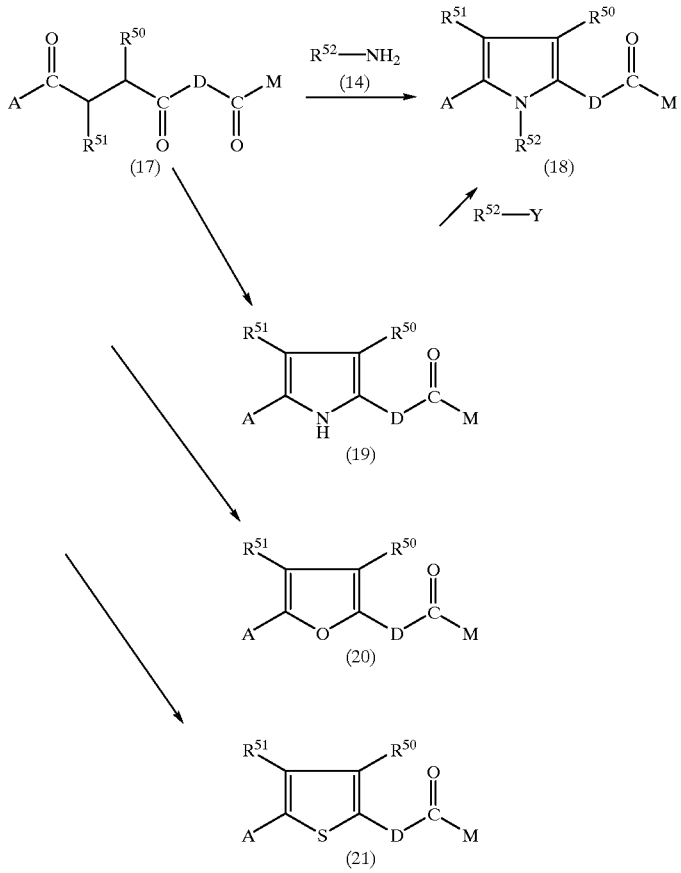

wherein A, D, M, Y, $R^{50}$, $R^{51}$ and $R^{52}$ have the same meanings as defined above.

A compound represented by the formula (16) can be prepared by reacting an aldehyde of the formula (1) with an organic metal reagent as in Preparation Example 1 and then oxidizing the resulting alcohol derivative.

Compound (17) can be obtained by reacting Compound (16) with an aldehyde of the formula (4) in the presence of a base through the use of 3-benzyl-5-(2-hydroxyethyl)-4-methylthiazolium chloride. Examples of the base include potassium carbonate, pyridine and triethylamine, while examples of the solvent include alcohol solvents such as methanol and ethanol, and N,N-dimethylformamide. The reaction temperature ranges from room temperature to the boiling point of the solvent, with a range of from 50° C. to the boiling point of the solvent being preferred.

Alternatively, Compound (17) can be obtained in a similar manner by reacting the aldehyde of the formula (1) with a compound of the formula (16).

From a γ-diketone of the formula (17), its pyrrole derivative (17), furan derivative (20) or thiophene derivative (21) can be obtained in a similar manner to the conversion of Compound (9)) to Compound (10), (12) or (13), respectively, in Preparation Process 1.

Preparation Process 3

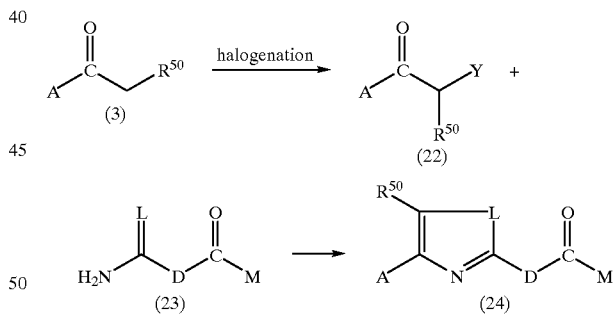

wherein A, D, M, Y and $R^{50}$ have the same meanings as defined above and L represents S or $>NR^{53}$ in which $R^{53}$ represents a hydrogen atom or a lower alkyl group.

A ketone derivative (3) is halogenated at its α position and then the resulting halogenated product (22) is reacted with a thioamide or amidine represented by the formula (23), whereby the corresponding thiazole or imidazole derivative represented by the formula (24) can be prepared. Exemplary halogenating reagents include bromine, copper bromide, N-bromosuccimide, chlorine, N-chlorosuccimide and iodine. The conversion into a heterocyclic compound is attained at the reaction temperature ranging from 0° C. to the boiling point of the solvent in the presence of a base such as pyridine, triethylamine or potassium carbonate in a solvent such as methanol, ethanol, isopropanol, tetrahydrofuran or N,N-dimethylformamide.

Preparation Process 4

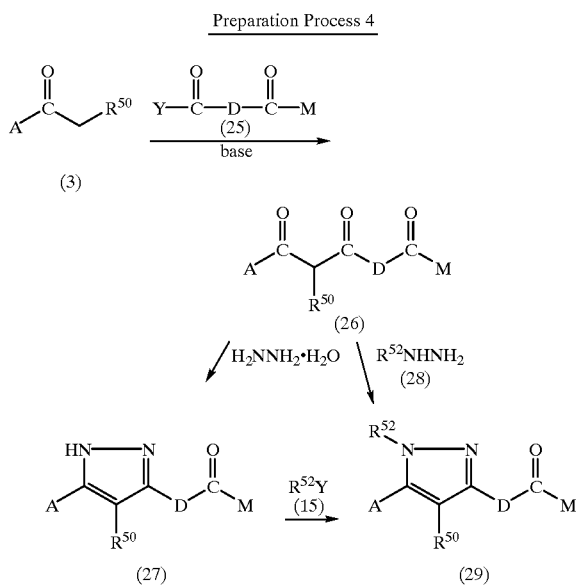

wherein A, D, M, Y, $R^{50}$ and $R^{52}$ have the same meanings as defined above.

A diketone derivative (26) can be obtained by reacting a ketone derivative (3) with an acid halide (25) in the presence of a base. As the base, lithium diisopropylamide or lithium bistrimethyl silylamide brings about good results. Examples of the solvent usable in the above reaction include ether solvents such as diethyl ether, tetrahydrofuran and 1,2-dimethoxyethane. The reaction temperature ranges from −78° C. to the boiling point of the solvent, with −78° C. to room temperature being preferred.

The diketone derivative (26) is reacted with hydrazine hydrate, whereby a pyrazole derivative (27) can be obtained. This reaction can be accislerated by the addition of hydrochloric acid, sulfuric acid, acetic acid, polyphosphoric acid or the like as a dehydrating agent. Any reaction solvent can be used insofar as it is principally inert to hydrazine. Examples include alcohol solvents such as methanol, ethanol and isopropanol, aromatic hydrocarbon solvents such as benzene, toluene and xylene, N,N-dimethylformamide and dimethylsulfoxide. Acids such as acetic acid can also be used as a solvent. The reaction temperature ranges from 0° C. to the boiling point of the solvent, with a range of from room temperature to the boiling point of the solvent being preferred. A pyrazole compound (29) can be obtained by carrying out the same reaction by using a hydrazine represented by the formula (28) or by reacting the pyrazole derivative (27) with a halide (15) in a similar manner to preparation process 1 and separating the resulting isomer by crystallization or column chromatography.

Preparation Process 5

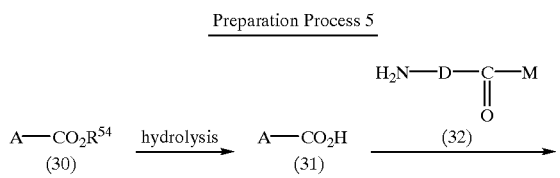

-continued

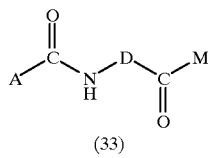

wherein A, D and M have the same meanings as defined above and $R^{54}$ represents a lower alkyl group.

A compound represented by the formula (31) can be obtained by alkali hydrolysis of an ester derivative represented by the formula (30). This reaction is carried out in a mixture of water and an alcohol such as methanol, ethanol or propanol, tetrahydrofuran or 1,4-dioxane in the presence of an alkali hydroxide such as sodium hydroxide or potassium hydroxide used in an excess amount. The reaction temperature falls within a range of room temperature to the boiling point of the solvent mixture, preferably within a range of from room temperature to 60° C. An amide compound represented by the formula (33) can be obtained by converting a carboxylic acid as compound (31) into corresponding acid halide, acid azide or acid anhydride in a manner known to date, followed by the reaction with an amine compound represented by the formula Preparation Process 6

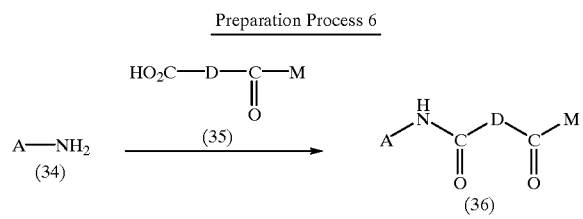

wherein A, D and M have the same meanings as defined above.

A compound of the formula (36) can be obtained by converting a carboxylic acid of the formula (35) into the corresponding acid halide, acid azide or acid anhydride in a manner known to date and then reacting an amine compound of the formula (34) therewith.

Furthermore, other compounds of the formula (1) according to the present invention car also be obtained by converting, in a manner known to date, the group of the compound prepared by any one of the processes described as Preparation Processes 1 to 6 or another process, said group being represented by the formula:

—D—CO—M wherein D and M have the same meanings as defined above.

In the case where the group represented by the formula: —D—CO—M is derived from a carboalkoxy-containing benzoate compound, it can be converted into its free carboxylic acid or physiologically acceptable salt thereof by alkali hydrolysis. The alkali hydrolysis is effected in a mixture of water with an alcohol such as methanol, ethanol or propanol, tetrahydrofuran or 1,4-dioxane in the presence of an alkali hydroxide such as sodium hydroxide or potassium hydroxide used in an excess amount at a temperature ranging from room temperature to the boiling point of the solvent.

The effects of the invention compound will next be described by Pharmacological Experimental Examples.

EXPERIMENTAL EXAMPLE
Receptor Binding Assay by Using Human Promyelocytic Leukemia Cells HL60

It is known that there exists a receptor for all-trans retinoic acid (Retinoic acid receptor: RAR) in the nucleus of HL60 cells [Clara Nervi et: al., Proc. Natl. Acad. Sci., 86, 5854 (1989)]. Specific binding of all-trans retinoic acid with PAR was found using a fraction extracted from the nucleus of HL60 and the binding capacity of each compound with PAR was studied by measuring the binding inhibition rate.

The nucleus-extracted fraction was prepared as described below.

In 15 ml of Solution A [5 mM :sodium phosphate (pH 7.4), 10 mM monothioglycerol, 10% v/v glycerol, 1 mM phenylmethyl sulfonyl fluoride (PMSF), 10 μg/ml of aprotinin and 25 μg/ml of leupeptin], HL60 cells ($5 \times 10^8$) were suspended. The resulting suspension was homogenized, followed by centrifugal separation to remove the supernatant. The precipitate so obtained was suspended in 15 ml of Solution B [10 mM tris-HCl (Tris-HCl) (pH 8.5), 10 mM monothioglycerol, 10% (v/v) glycerol, 1 mM PMSF, 10 μg/ml aprotinin, 25 μg/ml leupeptin and 0.4 M KCl]. After being allowed to stand at 4° C. for one hour, the resulting suspension was subjected to ultracentrifugation at 100,000 xg and 4° C. for one hour. The supernatant so obtained was refrigerated at −80° C. as a nucleus-extracted fraction until practical use (METHODS IN ENZYMOLOGY, 189, 248).

Receptor binding assay was carried out as follows:

To a polypropylene-made 96-well plate, 180 μl of the extracted fraction and 10 μl of all-trans retinoic acid or a diluted invention compound were added, followed by the addition of 10 μl of 10 nM $^3$H-all-trans retinoic acid. The resulting mixture was allowed to stand at 4° C. for 16 hours. To the reaction mixture was added a 3% charcoal-0.3% dextran solution and the resulting mixture was centrifuged to separate free $^3$H-all-trans retinoic acid. The count of the supernatant was determined by a scintillation counter. The specific binding with PAR was determined by deducting the above count from a count at the time when all-trans retinoic acid was added in an amount excessive by 200 times as a value of nonspecific binding. The compounds which will be described below suppressed the binding of $^3$H-all-trans retinoic acid according to the concentration. In addition, the 50% inhibition concentration of each compound was calculated and is shown in Table 1.

Differentiation and Induction Effects on HL60 Cells

It is known that human-derived promyelocytic leukemia cell strains HL60 differentiate into the corresponding granulocytic cells in the presence of all-trans retinoic acid [Breitman, T. Selonick., S. and Coiling, S. Proc. Natl. Acad. Sci., .77, 2936(1980)]. In general, cells after differentiation have come to express specific differentiated antigens on their surface. When the HL60 cells are differentiated into granulocytic cells, CD11b which is a differential antigen between granulocytes and monocytes is expressed on the surface of the cells [Fontana, J A., Reppuci, A. Durham, J P. and Mirand, D. Cancer Res. 46, 2469–2473(1986)]. Effects of the invention compound on the differentiation and induction into granulocyte cells were studied by making use of the above-described phenomenon.

HL60 cells were cultured and kept in RPMI 1640 (a medium formulated by Rosewell Park Memorial Institute) to which 10% bovine fetal serum, 1 mM sodium pyridinate, 50 μM β-mercaptoethanol, 100 IU/ml of Penicillin and 100 μg/ml o f streptomycin had been added.

On each well of a 24-well plate, a 1 ml portion of the suspension containing HL60 in an amount of $1 \times 10^5$ cfu/ml was seeded. The invention compound was then added thereto at varied concentrations, followed by cultivation for 5 days in a 5% $CO_2$-air incubator. After cultivation, the cells of each well were collected in a test tube, to which an FITC-labeled monoclonal antibody against Cd11b, that is, a granulocyte-monocyte specific antigen was added. The cells were then immobilized with 0.2% paraformaldehyde.

The existing ratio of CD11b positive cells in the vial HL60 cell group present in each well was determined using flow cytometry [Miller, L J., Schwarting, R. and Springer, T A. J. Immunol. 137, 2891–2900(1986)]. The existing ratios of CD11b positive cells of compounds which will be described below were increased according to the concentration. The concentration at which the existing ratio of the positive cells becomes 33% is defined as $ED_{1/3}$. The $ED_{1/3}$ of each compound is calculated and is shown in Table 1.

TABLE 1

|  | Receptor binding assay using HL60 cells $IC_{50}$ (nM) | Differentiation and induation effects of HL60 cells $ED_{1/3}$ (nM) |
| --- | --- | --- |
| All-trans-retinoic acid | 1.1 | 1.8 |
| Compound of Ex. 4 | 7.2 | 0.2 |
| Compound of Ex. 6 | 1.6 | 0.056 |
| Compound of Ex. 23 | 11 | 0.6 |
| Compound of Ex. 42 | 2.0 | 0.33 |
| Compound of Ex. 43 | 36 | 0.36 |
| Compound of Ex. 85 | <0.5 | 1.0 |
| Compound of Ex. 99 | 3.4 | 0.047 |
| 1) | 0.5 | 0.94 |

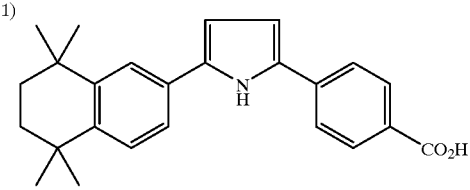

Note) Refer to JP-A-2-240058

As is apparent from the above results, compounds according to the present invention have retinoid receptor agonist effects and are therefore expected as medicaments effective against various diseases, which will be described below, as a preventive and/or therapeutic for autoimmune diseases, immunosuppression upon organ transplantation and malignant neoplasm. The use of the compounds of the present invention are not limited to the following diseases.

Various keratosis, psoriasis, acne, leukoplakia, xeroderma pigmentosum.

Various alopecia such as alopecia areata, alopecia seborrheica, melanoderma cachecticorum.

Postmenopausal osteoporosis, senile osteoporosis, cataplectic osteoporosis, diabetic osteopenia, chronic rheumatism osteopenia, renal osteomalacia, ectopic ossification.

Osteoarthritis, glenoidal periarthritis

Autoimmune diseases such as chronic rheumatoid arthritis, multiple sclerosis (MS), systemic lupus erythematosus (SLE), Behyet disease, mycosis fungoides (MF), progressive systemic sclerosis, dermatomyositis (DM) and nodular arteriosclerosis.

Rejection symptoms upon organ transportation

Atopic dermatitis

Asthma (immediate allergy reaction)

Immune function activation in immunodeficiency, cytomegalovirus infectious diseases of a fetus or upon immune depression, opportunistic infection.

Hyperthyroidism

Cancers such as squamous cell carcinoma, cystocarcinoma, pulmonary carcinoma, esophageal carcinoma, cervical carcinoma, large bower/rectum cancer, prostatic cancer, uterocervical carcinoma, mammary carcinoma, neurocytoma, acute promyelocytic leukemia, acute myelocytic leukemia, osteomyelodysplasia, chronic myelocytic leukemia and cutaneous T-cell lymphoma.

Hyperkalemia

Pulmonary fibrosis, hepatic fibrosis, hepatic cirrhosis.

For the administration of the invention compound as a preventive and/or therapeutic for the above-exemplified disease, it may be orally administered as tablets, powders, granules, capsules or syrups; or it may be parenterally administered as a suppository, injection, external preparation or drops.

These preparations for oral or parenteral administration are formulated in a manner known per se in the art by using an ordinarily used pharmaceutically acceptable carrier.

Subcutaneous, intramuscular and intravenous injections and dropping injection are formulated in a manner known per se in the art by adding, if necessary, a pH regulator, buffer, stabilizer and/or solubilizing agent to a main agent, followed by lyophilization as needed.

EXAMPLES

The present invention will hereinafter be described by examples. It should however be borne in mind that the present invention is not limited to or by the following examples.

Incidentally, preparation examples of a raw material used in the examples of the present invention will be shown as referential examples.

In the following examples and referential examples, Me represents a methyl group and Et represents an ethyl group.

Example 1

4-[4-[2-[2-(5,6,7,8-Tetrahydro-5,5,8,8-tetramethylquinoxalyl)]pyrrolyl]]benzoic acid

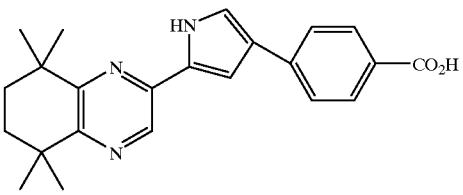

Step 1

2-Acetyl-5,6,7,8-tetrahydro-5,5,8,8-tetramethylquinoxaline

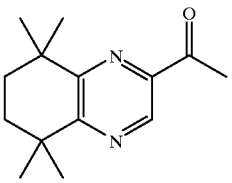

In 180 ml of diethyl ether were dissolved 3.0 g of 5,6,7,8-tetrahydro-5,5,8,8-tetramethyl-2-quinoxalinol, followed by the dropwise addition of a 3M diethyl ether solution of methyl magnesium bromide at 0° C. under a nitrogen gas stream. After stirring for 30 minutes, aqueous saturated ammonium chloride was added to the reaction mixture, followed by extraction with ethyl acetate. The organic layer was washed successively with an aqueous solution of hydrochloric acid, water and saturated saline, dried over anhydrous magnesium sulfate and concentrated under reduced pressure. The residue was subjected to chromatography on a silica gel column (developing solvent: 20% ethyl acetate/n-hexane), whereby 3.2 g of a colorless oil were obtained. A solution of 2.94 ml of dimethyl sulfoxide in 3 ml of dichloromethane was added dropwise to a solution of 41.8 ml of oxalyl chloride in 80 ml of dichloromethane at −60° C., followed by stirring for 5 min. To the reaction mixture was added dropwise a solution of 3.2 g of the above-obtained colorless oil in 40 ml of dichloromethane, followed by stirring for 15 minutes, dropwise addition of 13.8 ml of triethylamine and stirring for further 5 minutes. The reaction mixture was raised to room temperature and stirred for 15 minutes, followed by the addition of water. Then the resulting mixture was extracted with dichloromethane. The organic layer was successively washed with water and saturated saline, dried over anhydrous magnesium sulfate and then concentrated under reduced pressure. The residue was subjected to chromatography on a silica gel column (developing solvent: 10% ethyl acetate/n-hexane), whereby 1.9 g of the title compound were obtained in the form of a pale yellow solid.

Melting point: 68–69° C.; $^1$H-NMR (CDCl$_3$, 400 MHz) δ; 1.33(s,6H), 1.35(s,6H), 1.82(s,4H), 2.68(s,3H), 8.95(s,1H).

Step 2:

Methyl 4-[1-[2-(5,6,7,8-tetrahydro-5,5,8,8-tetramethylquinoxalyl)]-1-oxo-2-propenyl]]benzoate

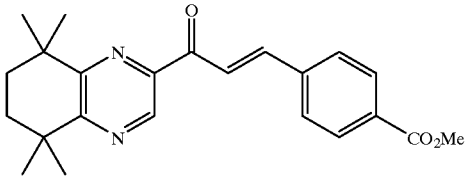

In a solution of 1.9 g of 2-acetyl-5,6,7,8-tetrahydro-5,5,8,8-tetramethylquinoxaline and 1.3 g of monomethyl ester of terephthalaldehydic acid in 50 ml of methanol, a piece of sodium hydroxide was added and the resulting mixture was stirred overnight. The precipitate so formed was collected by filtration and dried under reduced pressure, whereby 2.6 g of the title compound were obtained in the form of a pale yellow solid.

Melting point: 168–170° C.; $^1$H-NMR (CDCl$_3$, 400 MHz) δ; 1.37(s,6H), 1.43(s, 6H), 1.86(s, 4H), 3.95(s,3H), 7.74(d, J=8.2 Hz,2H), 7.95(d,J=16.0 Hz, 1), 8.10(d,J=8.2 Hz,2H), 8.26(d,J=16.0 Hz,1H),9.11(s,1H).

Step 3

Methyl 4-[3-[1-[2-(5,6,7,8-tetrahydro-5,5,8,8-tetramethylquinoxalyl)]-4,4-dimethoxy-1-oxobutyl]]benzoate

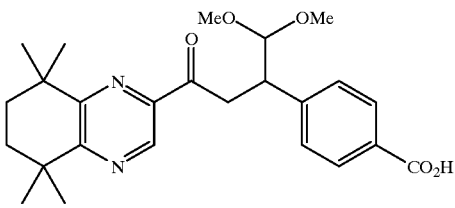

In 30 ml of nitromethane and 9 ml of tetrahydrofuran were dissolved 2.6 g of methyl 4-[1-[2-(5,6,7,8-tetrahydro-5,5,8,3-tetramethylquinoxalyl)]-1-oxo-2-propenyl]benzoate. To the resulting solution were added 1.5 ml of Triton B, followed by stirring overnight. Ethyl acetate was added to the reaction mixture. The resulting mixture was washed successively with an aqueous solution of hydrochloric acid, water, a saturated aqueous solution of sodium bicarbonate, water and saturated saline, dried over anhydrous magnesium sulfate and then concentrated under reduced pressure, whereby a pale yellow oil was obtained. The oil so obtained was dissolved in 70 ml of a 1:1 mixture of tetrahydrofuran and dichloromethane. The resulting solution was added dropwise to a solution of 3.7 ml of sodium methoxide in 23 ml of methanol, which solution had been cooled to −35° C., followed by stirring for 40 min. The reaction mixture was added dropwise to a solution of 9.3 ml of concentrated sulfuric acid in 46 ml of methanol, which solution had been cooled to −35° C. The mixture so obtained was raised to room temperature and stirred for 40 minutes. The reaction mixture was poured into a saturated aqueous solution of sodium bicarbonate, followed by extraction with ethyl acetate. The organic layer was washed successively with water and saturated saline, dried over anhydrous magnesium sulfate and then concentrated under reduced pressure, whereby 2.8 g of the title compound were obtained in the form of a pale brown powder. The resulting powder was provided for the subsequent reaction without purification.

Step 4

Methyl 4-[4-[2-[2-(5,6,7,8-tetrahydro-5,5,8,8-tetramethylquinoxalyl)]pyrrolyl]]benzoate

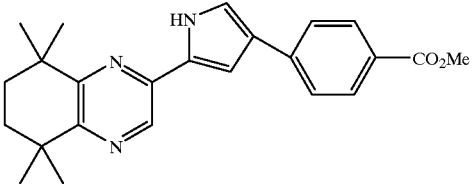

In 5 ml of acetic acid was dissolved 0.25 g of methyl 4-[3-[1-[2-5,6,7,8-tetrahydro-5,5,8,8-tetramethylquinoxalyl]]-4,4-dimethoxy-1-oxobutyl]] benzoate. To the resulting solution was added 0.22 g of ammonium acetate, followed by heating under reflux for one hour. Ice was added to the reaction mixture, followed by extraction with ethyl acetate. The organic layer was washed successively with a saturated aqueous solution of sodium bicarbonate, water and saturated saline, dried over anhydrous magnesium sulfate, and then concentrated under reduced pressure. The residue was subjected to chromatography on a silica gel column ,developing solvent: 10% ethyl acetate/n-hexane), whereby 0.19 g of the title compound was obtained in the form of a dark green solid.

$^1$H-NMR (CDCl$_3$, 400 MHz) δ; 1.34(s,6H), 1.36(s,6H), 1.81(s,4H), 3.93(s,3H), 7.06(dd,J=0.8,1.6 Hz,1H), 7.32(dd, J=1.2,1.6 Hz,1H), 7.63(d,J=8.4 Hz,2H), 8.03(d,J=8.4 Hz,2H), 8.68(s,1H), 9.55(br s,1H).

Step 5

4-[4-[2-[2-(5,6,7,8-Tetrahydro-5,5,8,8-tetramethylquinoxalyl)]pyrrolyl]]benzoic acid

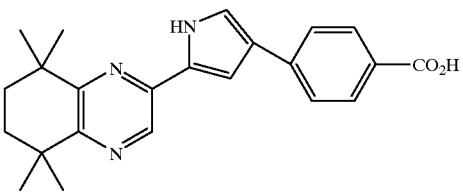

In 10 ml of ethanol was dissolved 0.19 g of methyl 4-[4-[2-[2- (5,6,7,8-tetrahydro-5,5,8,8-tetramethylquinoxalyl)]pyrrolyl]]benzoate. To the resulting solution were added 2 ml of a 5N aqueous solution of sodium hydroxide, followed by stirring at room temperature for 2 hours. The pH of the reaction mixture was adjusted to be weakly acidic by the addition of an aqueous solution of hydrochloric acid. The crystals so precipitated were collected by filtration, washed with water and dried under reduced pressure, whereby 0.14 g of the title compound was obtained in the form of a grayish black solid.

Melting point: 192 to 194° C.; $^1$H-NMR (CDCl$_3$, 400 MHz) δ; 1.27(s,6H), 1.35(s,6H), 1.75(s,4H), 7.30–7.34(m, 1H), 7.54–7.59(m,1H), 7.72(d,J=8.4 Hz,2H), 7.88(d,J=8.4 Hz,2H),8.79(s,1H).

Example 2

4-[4-[2-[2-(5,6,7,8-Tetrahydro-5,5,8,8-tetramethylquinoxalyl)]thienyl]]benzoic acid

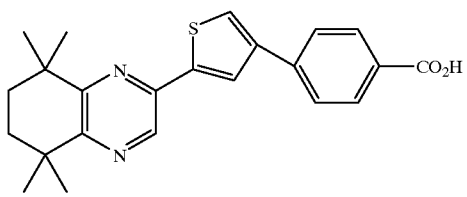

In 10 ml of xylene was dissolved 0.4 g of methyl 4-[3-[1-[2-(5,6,7,8-tetrahydro-5,5,8,8-tetramethylquinoxalyl)]-4,4-dimethoxy-1-oxobutyl] benzoate. To the resulting solution was added 0.2 g of pentaphosphorus disulfide, followed by heating under reflux for 2 hours. The reaction mixture was subjected to chromatography on a silica gel column (developing solvent: 5% ethyl acetate/n-hexane), whereby 0.1 g of a yellow solid was obtained. In a similar manner to the step 5 of Example 1, hydrolysis was carried out to obtain 80 mg of the title compound in the form of a pale brown solid.

Melting point: 247 to 249° C.; $^1$H-NMR (DMSO-$d_6$, 400 MHz) δ; 1.28(s,6H), 1.30(s,6H), 1.77(s,4H), 7.90(d,J=8.4 Hz,2H), 7.99(d,J=8.4 Hz,2H), 8.17(s,1H), 8.42(s,1H), 9.06 (s,1H).

Example 3

4-[4-[2-[2-(5,6,7,8-tetrahydro-5,5,8,8-tetramethylquinoxalyl)]-1-methylpyrrolyl]]benzoic acid

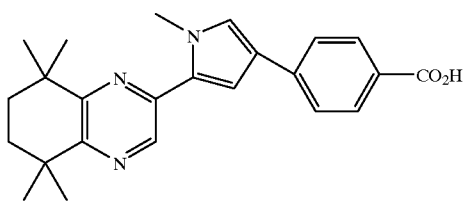

In 10 ml of N,N-dimethylformamide were dissolved 90 mg of methyl 4-[4-[2-[2-(5,6,7,8-tetrahydro-5,5,8,8-tetramethylquinoxalyl)]pyrrolyl]]benzoate. To the resulting solution was added 14 mg of sodium hydride and 29 μl of methyl iodide at 0° C., followed by stirring for one hour. To the reaction mixture was added a saturated aqueous solution of ammonium chloride and the resulting mixture was extracted with ethyl acetate. The organic layer was washed successively with water and saturated saline, dried over anhydrous magnesium sulfate and concentrated under reduced pressure. The residue so obtained was subjected to chromatography on a silica gel column (developing solvent: 5% ethyl acetate/n-hexane), whereby 60 mg of a colorless sold were obtained. The resulting solid was hydrolyzed in a similar manner to Step 5 of Example 1, whereby 52 mg of the title compound were obtained in the form of a pale yellow solid.

Melting point: 300° C. (decomposed); $^1$H-NMR (DMSO-$d_6$, 400 MHz) δ; 1.28(s,6H), 1.31(s,6H), 1.77(s,4H), 3.99(s, 3H), 7.26–7.29(m,1H), 7.57–7.60(m,1H), 7.66(d,J=8.4 Hz,2H), 7.88(d,J=8.8 Hz,2H), 8.79(s,1H).

Example 4

4-[4-[2-[2-(5,6,7,8-Tetrahydro-5,5,8,8-tetramethylquinoxalyl)]furyl]]benzoic acid

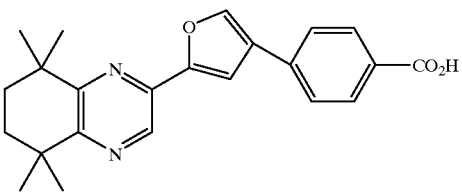

In 10 ml of concentrated sulfuric acid were dissolved 2.0 g of methyl 4-[3-[1-[2-(5,6,7,8-tetrahydro-5,5,8,8-tetramethylquinoxalyl)]-4,4-dimethoxy-1-oxobutyl]] benzoate and the resulting solution was stirred at room temperature overnight. The reaction mixture was poured into a saturated aqueous solution of sodium bicarbonate, followed by extraction with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/n-hexane), whereby 300 mg of a pale yellow solid were obtained. The resulting solid was hydrolyzed in a similar manner to Step 5 of Example 1, whereby 150 mg of the title compound were obtained in the form of a colorless solid.

Melting point: 267 to 269° C.; $^1$H-NMR (CDCl$_3$, 400 MHz) δ; 1.35(s,6H), 1.38(s,6H), 1.83(s,4H), 7.42(d,J=0.8 Hz,1H), 7.67(d,J=8.4 Hz,2H), 7.92(d,J=0.8 Hz,1H), 8.13(d, J=8.4 Hz,2H), 8.77(s,1H).

Example 5

4-[4-[2-[2-(5,6,7,8-Tetrahydro-5,5,8,8-tetramethylquinoxalyl)]-1-ethylpyrrolyl]]benzoic acid

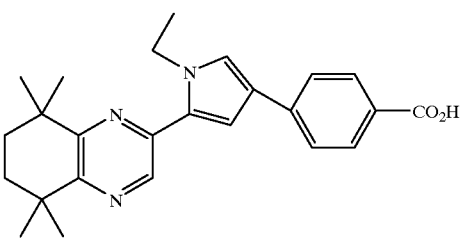

In 2 ml of acetic acid were dissolved 190 mg of methyl 4-[4-[3-[1-[2-(5,6,7,8-tetrahydro-5,5,8,8-tetramethylquinoxalyl)]-4,4-dimethoxy-1-oxobutyl]] benzoate. To the resulting solution was added 51 mg of ethylamine hydrochloride, followed by heating at 70° C. for 4 hours. The reaction mixture was poured into a saturated aqueous solution of sodium bicarbonate and the resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 10% ethyl acetate/n-hexane), whereby 64 mg of a yellow solid were obtained. The resulting solid was hydrolyzed in a similar manner to Step 5 of Example 1, whereby 44 mg of the title compound were obtained in the form of a pale yellow solid.

$^1$H-NMR (DMSO-$d_6$, 400 MHz) δ; 1.28(s,6H), 1.30(s, 6H), 1.35(t,J=6.8 Hz,3H), 1.77(s,4H), 4.48(q,J=6.8 Hz,2H), 7.31(d,J=2.0 Hz,1H), 7.67(d,J=2.0 Hz,1H), 7.69(d,J=8.4 Hz,2H), 7.89(d,J=8.4 Hz,2H), 8.83(s,1H).

Example 6

4-[2-[5-[2-(5,6,7,8-Tetrahydro-5,5,8,8-tetramethylquinoxalyl)]pyrrolyl]]benzoic acid

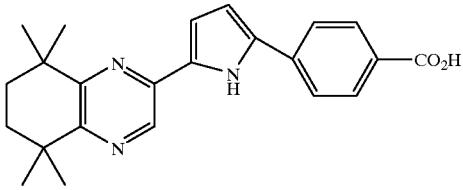

Step 1

1-[2- (5,6,7,8-Tetrahydro-5,5,8,8-tetramethylquinoxalyl)]-1-oxo-2-propene

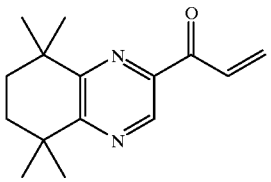

In 100 ml of diethyl ether were dissolved 1.5 g of 5,6,7,8-tetrahydro-5,5,8,8-tetramethyl-2-quinoxalinol, followed by the dropwise addition of 8.3 ml of vinyl magnesium bromide (1M tetrahydrofuran solution) at 0° C. After stirring for one hour, the reaction mixture was added with a saturated aqueous-solution of ammonium chloride. The resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 10% ethyl acetate/n-hexane), whereby 1.84 g of a pale yellow oily substance were obtained. Under a nitrogen gas stream, a solution of 1.26 ml of dimethyl sulfoxide in 5 ml of dichloromethane was added dropwise to a solution of 0.78 ml of oxalyl chloride in 40 ml of dichloromethane at −60° C., followed by stirring for 5 minutes. To the reaction mixture, a solution of 1.84 g of the pale yellow oil in 20 ml of dichloromethane which had been obtained in advance was added dropwise, followed by stirring for 15 minutes. Triethylamine (6.0 ml) was added dropwise to the reaction mixture and the resulting mixture was stirred for 5 minutes, followed by heating to room temperature and stirring for 15 minutes. Water was added to the reaction mixture, followed by extraction with dichloromethane. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/n-hexane), whereby 0.76 g of the title compound was obtained in the form of a pale yellow oily substance.

$^1$H-NMR (CDCl$_3$, 400 MHz) δ; 1.35(s,6H), 1.37(s,6H), 1.84(s,4H), 5.93(dd,J=2.0,10.4 Hz,1H), 6.63(dd,J=2.0,17.2 Hz,1H), 7.82(dd,J=10.4,17.2 Hz,1H), 9.06(s,1H).

Step 2

Methyl 4-[4-[2-(5,6,7,8-tetrahydro-5,5,8,8-tetramethylquinoxalyl)]-4-oxo-1-butanoyl]benzoate

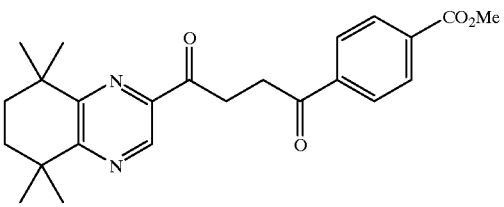

PROCESS 1

In 60 ml of ethanol were dissolved 0.76 g of 1-[2-(5,6,7,8-tetrahydro-5,5,8,8-tetramethylquinoxalyl)]-1-oxo-2-propene, 0.51 g of methyl ester of terephthalaldehydic acid, 85 mg of sodium acetate and 84 mg of 3-benzyl-5-(2-hydroxyethyl)-4-methylthiazolium chloride. The resulting solution was heated under reflux for 6 hours. The reaction mixture was allowed to cool down, and then concentrated under reduced pressure. The residue so obtained was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 10% ethyl acetate/n-hexane), whereby 0.38 g of the title compound was obtained in the form of a yellow solid.

Melting point: 92 to 94° C.;

PROCESS 2

In 10 ml of dimethylformamide were dissolved 300 mg of 5,6,7,8-tetrahydro-5,5,8,8-tetramethylquinoxaline-2-carbaldehyde, 260 mg of methyl 4-acrylcyl-benzoate, 74 mg of 3-benzyl-5-(2-hydroxyethyl)-4-ethylthiazolium chloride and 0.2 ml of triethylamine. The resulting solution was stirred at 100° C. for 30 minutes. After being allowed to cool down, the reaction mixture was extracted with ethyl acetate. The organic layer was successively washed with dilute hydrochloric acid and saturated saline, dried over anhydrous magnesium sulfate and-concentrated under reduced pressure. The residue so obtained was subjected to chromatography on a silica gel column (developing solvent: 7% ethyl acetate/n-hexane), whereby 420 mg of the title compound were obtained in the form of a colorless solid.

$^1$H-NMR (CDCl$_3$, 400 MHz) δ; 1.35(s,6H), 1.38(s,6H), 1.84(s,4H), 3.46(t,J=6.4 Hz,2H), 3.68(t,J=6.4 Hz,2H), 3.96 (s,3H), 8.08(d,J=8.0 Hz,2H), 8.15(d,J=8.0 Hz,2H), 8.97(s, 1H).

Step 3

4-[2-[5-[2-(5,6,7,8-Tetrahydro-5,5,8,8-tetramethylquinoxalyl)]pyrrolyl]]benzoic acid

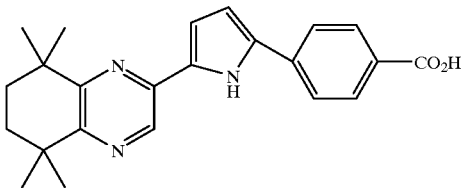

In 50 ml of methanol were dissolved 380 mg of methyl 4-[4-[2-(5,6,7,8-tetrahydro-5,5,8,8-tetramethylquinoxalyl)]-4-oxo-1-butanoyl]benzoate. To the resulting solution were added 358 mg of ammonium acetate, followed by heating under reflux for 8 hours. Methanol was distilled off under reduced-pressure and the residue was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/n-hexane), whereby 260 mg of a yellow solid were obtained. In a similar manner to step 5 of Example 1, a 100 ml portion of the resulting solid was hydrolyzed, whereby 90 mg of the title compound were obtained in the form of a yellow solid.

Melting point: 300° C. (decomposed); $^1$H-NMR (CDCl$_3$, 400 MHz) δ; 1.34(s,6H), 1.40(s,6H), 1.82(s,4H), 6.76(dd, J=2.8,3.8 Hz,1H), 6.84(dd,J=.2.4,3.8 Hz,1H), 7.65(d,J=8.4 Hz,2H), 8.14(d,J=8.4 Hz,2H), 8.68(s,1H), 9.66(br s,1H).

Example 7

4-[2-[5-[2-(5,6,7,8-Tetrahydro-5,5,8,8-tetramethylquinoxalyl)]thienyl]]benzoic acid

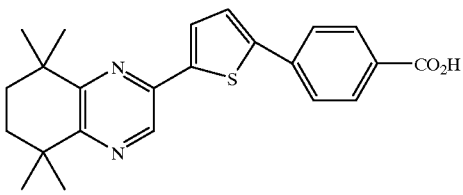

In 10 ml of xylene were dissolved 200 mg of methyl 4-[4-[2-(5,6,7,8-tetrahydro-5,5,8,8-tetramethylquinoxalyl)]-4-oxo-1-butanoyl]benzoate. To the resulting solution was added 0.1 g of pentaphosphorus disulfide, followed by heating under reflux for 2 hours. The reaction mixture was subjected to chromatography on a silica gel column (developing solvent: 5% ethyl acetate/n-hexane), whereby 90 mg of a yellow solid were obtained. The resulting solid was hydrolyzed in a similar manner to Step 5 of Example 1, whereby 67 mg of the title compound were obtained in the form of a pale yellow solid.

Melting point: 292° C. (decomposed). $^1$H-NMR (CDCl$_3$, 400 MHz) δ; 1.20(s,6H), 1.24(s,6H), 1.68(s,4H), 7.31(d,J= 3.6 Hz,1H), 7.47(d, J=3.6 Hz,1H), 7.60(d,J=8.4 Hz,2H), 7.94(d,J=83.4 Hz,2H), 8.58(s,1H).

Example 8

4-[2-[5-[2-(5,6,7,8-Tetrahydro-5,5,8,8-tetramethylquinoxalyl)]furyl]]benzoic acid

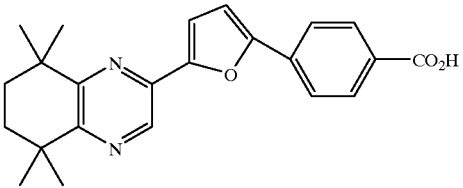

In 2 ml of concentrated sulfuric acid were dissolved 200 mg of methyl 4-[4-[2-(5,6,7,8-tetrahydro-5,5,8,8-tetramethylquinoxalyl)]-4-oxo-1-butanoyl]benzoate, followed by stirring at room temperature overnight. The reaction mixture was poured into a saturated aqueous solution of sodium bicarbonate. The resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/n-hexane), whereby 120 mg of a pale yellow solid were obtained. The resulting solid was hydrolyzed in a similar manner to Step 5 of Example 1, whereby 90 mg of the title compound were obtained in the form of an orange solid.

Melting point: 275° C. (decomposed); $^1$H-NMR (CDCl$_3$, 400 MHz) δ; 1.18(s,6H), 1.20(s,6H), 1.66(s,4H), 6.77(d,J= 3.6 Hz,1H), 7.03(d, J=3.6 Hz,1H), 7.64(d,J=8.4 Hz,2H), 7.94(d,J=8.4 Hz,2H), 8.66(s,1H).

Example 9

4-[2-[5-[2-(5,6,7,8-Tetrahydro-5,5,8,8-tetramethylquinoxalyl) ]-1-methylpyrrolyl]]benzoic acid

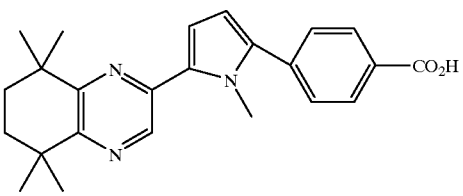

In 10 ml of N,N-ditethylformaminde were dissolved 120 mg of methyl 4-[2-[5-[2-(5,6,7,8-dtetrahydro-5,5,8,8-tetramethylquinoxalyl) ]pyrrolyl]benzoate. To the resulting solution were added 19 mg of sodium hydride and 38 μl of methyl iodide at 0° C., followed by stirring for one hour. A saturated aqueous solution of ammonium chloride was added to the reaction mixture and the resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/n-hexane), whereby 110 mg of a pale yellow solid were obtained. The resulting solid was hydrolyzed in a similar manner to Step 5 of Example 1, whereby 96 mg of the title compound were obtained in the form of a pale yellow solid.

Melting point: 252 to 254° C.; $^1$H-NMR (CDCl$_3$, 400 MHz) δ; 1.35(s,6H), 1.36(s,6H), 1.82(s,4H), 3.96(s,3H), 6.42(d,J=4.0 Hz, 1H), 6.72(d,J=4.0 Hz,1H), 7.59(d,J=8.4 Hz,2H), 8.15(d,J=8.4 Hz,2H), 8.65(s,1H).

Example 10

4-[2-[5-[2-(5,6,7,8-Tetrahydro-5,5,8,8-tetramethylquinoxalyl)]-1-ethylpyrrolyl]benzoic acid

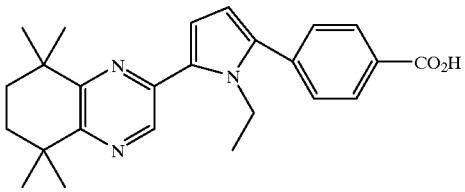

In 2 ml of acetic acid were dissolved 100 ml of methyl 4-[4-[2-(5,6,7,8-tetrahydro-5,5,8,8-tetramethylquinoxalyl)]-4-oxo-1-butarnoyl]benzoate. To the resulting solution were added 30 mg of ethylamine hydrochloride, followed by heating under reflux for 2 days. The reaction mixture was poured into the saturated aqueous solution of sodium bicarbonate and the resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/n-hexane), whereby 48 mg of a colorless oil were obtained. The resulting oil was hydrolyzed in a similar manner to Step 5 of Example 1, whereby 32 mg of the title compound were obtained in the form of a pale yellow solid.

Melting point: 258 to 260° C.; $^1$H-NMR (DMSO-d$_6$, 400 MHz) δ; 1.06(t,J=6.8 Hz,3H), 1.28(s,6H), 1.29(s,6H), 1.77 (s,4H), 4.56(q, J=6.8 Hz,2H), 6.31(d,J=4.0 Hz,1H), 6.89(d, J=4.0 Hz,1H), 7.55(d, J=8.4 Hz,2H), 7.99(d,J=8.4 Hz,2H), 8.78(s,1H).

Example 11

4-[2-[5-[2-(5,6,7,8-tetrahydro-5,5,8,8-tetramethylquinoxalyl)]-1-isopropylpyrrolyl]]benzoic acid

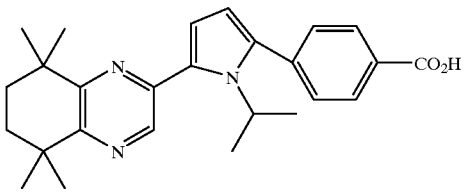

In 3 ml of acetic acid were dissolved 160 mg of methyl 4-[4-[2-(5,6,7,8-tetrahydro-5,5,8,8-tetramethylquinoxalyl)]-4-oxo-1-butanoyl]benzoate. To the resulting solution were added 3 ml of isopropylamine, followed by heating under refrlux for 3 hours. The reaction mixture was poured into, a saturated aqueous solution of sodium bicarbonate and the resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent:5% ethyl acetate/hexane), whereby 120 mg of a yellow solid were obtained. The resulting solid was hydrolyzed in a similar manner to Step 5 of Example 1, whereby 100 mg of the title compound were obtained in the form of a pale yellow solid.

Melting point: 234 to 236° C.; $^1$H-NMR (DMSO-d$_6$, 400 MHz) δ; 1.29(s,6H), 1.32(s,6H), 1.40(d,J=6.8 Hz,6H), 1.78 (s,4H), 4.72–34.83(m,1H), 6. 20(d,J=4.0 Hz,1H), 6.63(d,J= 3.6 Hz,1H), 7.56(d, J=8.4 Hz,2H), 7.99(d,J=8.4 Hz,2H), 8.66(s,1H).

Example 12

4-{2-{5-[2-(5,6,7,8-tetrahydro-5,5,8,8-tetramethylquinoxalyl)]-4-1-cyclopropylpyrrolyl}}benzoic acid

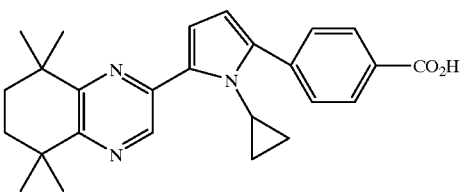

In 3 ml of acetic acid were dissolved 200 mg of methyl 4-[4-[2-(5,6,7,8-tetrahydro-5,5,8,8-tetramethylquinoxalyl)]-4-oxo-1-butanoyl]benzoate. To the resulting solution were added 3 ml of cyclopropylamine, followed by heating under reflux for 2 hours. The reaction mixture was poured into a saturated aqueous solution of sodium bicarbonate and the resulting solution was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetatecdhexane), whereby 210 mg of a pale yellow solid were obtained. The resulting solid was hydrolyzed in a similar manner to Step 5 of Example 1, whereby 164 mg of the title compound were obtained in the form of a pale yellow solid.

$^1$H-NMR (DMSO-d$_6$, 400MHz) δ; 0.14–0.20(m,2H), 0.70–0.76(m,2H), 1.30(s,6H), 1.33(s,6H), 1.79(s,4H), 3.94–4.00(m,1H), 6.43(d,J=3.6 Hz,1H), 6.66(d,J=4.0 Hz,1H), 7.77(d,J=8.4 Hz,2H), 7.96t,J=8.4 Hz,2H), 8.69(s, 1H).

Example 13

4-{2-{5-[2-(5,6,7,8-Tetrahydro-5,5,8,8-tetramethylquinoxalyl)]-1-pentylpyrrolyl}}benzoic acid

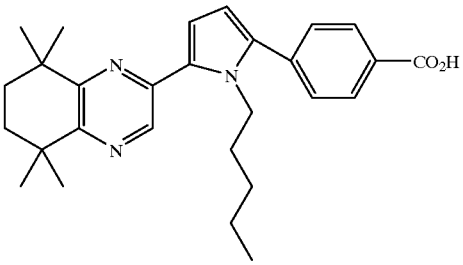

In 2 ml of acetic acid were dissolved 108 mg of methyl 4-[4-[2-(5,6,7,8-tetrahydro-5,5,8,8-tetramethyiquinoxalyl)]-

4-oxo-1-butanoyl]benzoate. To the resulting solution were added 62 μl of amylamine, followed by heating under reflux for 2 hours. The reaction mixture was poured into a saturated aqueous solution of sodium bicarbonate and the resulting solution was extracted with ethyl acetate. The organic layer was successively washed with water and saturated sialine, dried over anhydrous magnesium sulfate and concentrated under reduced pressure. The residue so obtained was subjected to chromatography on a silica gel column (developing solvent: 5% ethyl acetate/hexane), whereby 80 mg of a pale yellow solid were obtained. The resulting solid was hydrolyzed in a similar manner to Step 5 of Example 1, whereby, 66 mg of the title compound were obtained in the form of a pale yellow solid.

$^1$H-NMR (DMSO-$d_6$, 400 MHz) δ; 0.55–0.62(m,3H), 0.84–0.97(m,4H), 1.28(s,6H), 1.30(s,6H), 1.77(s,4H), 3.27–3.85(m,4H), 4.53–4.60(m,2H), 6.34 (d,J=4.0 Hz,1H), 6.87(d,J=3.6 Hz,1H), 7.58(d,J=8.4 Hz,2H), 8.00(d,J=8.0 Hz,2H), 8.76(s,1H).

Example 14

4-{2-{5-[2-(5,6,7,8-Tetrahydro-5,5,8,8-tetramethylquinoxalyl)]-1-isobutylpyrrolyl}}benzoic acid

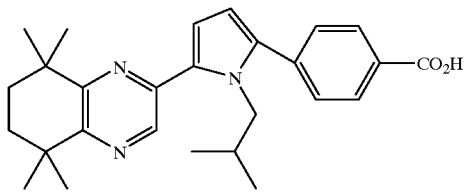

In 2 ml of acetic acid were dissolved 110 mg of methyl 4-4-[2-(5,6,7,8-tetrahydro-5,5,8,8-tetramethylquinoxalyl)]-4-oxo-1-butanoyl]benzoate. To the resulting solution were added 2 ml of isobutylamine, followed by heating under reflux for 2 hours. The reaction mixture was poured into a saturated aqueous solution of sodium bicarbonate and the resulting solution was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/hexane), whereby 75 mg of a pale brown solid were obtained. The resulting solid was hydrolyzed in a similar manner to Step 5 of Example 1, whereby 66 mg of the title compound were obtained in the form of a pale yellow solid.

$^1$H-NMR (DMSO-$d_6$, 400 MHz) δ; 0.40(d,J=6.4 Hz,6H), 1.28(s,6H), 1.32(s,6H), 1.77(s,4H), 4.45–4.55(m,1H), 6.35 (d,J=3.2 Hz,1H), 6.90(d,J=4.0 Hz,1H), 7.57(d,J=8.4 Hz,2H), 7.99(d,J=8.0 Hz,2H), 8.77(s,1H).

Example 15

4-{2-{5-[2-(5,6,7,8-Tetrahydro-5,5-dimethylquinoxalyl)]pyrrolyl}}benzoic acid

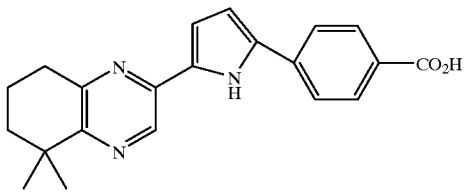

Step 1

Methyl 4-[4-[2-(5,6,7,8-tetrahydro-5,5-dimethylquinoxalyl)]-4-oxo-1-butanoyl]benzoate

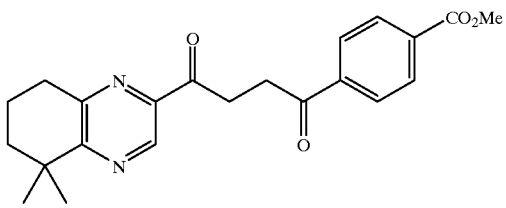

In 10 ml of N,N-dimethylformamide were dissolved 157 mg of a mixture of 5,6,7,8-tetrahydro-5,5-dimethylquinoxaline-2-carbaldehyde and 5,6,7,8-tetrahydro-8,8-dimethylquinoxaline-2-carbaldehyde, 157 mg of methyl 4-acryloyl-benzoate, 111 mg of 3-benzyl-5-(2-hydroxyethyl)-4-methylthiazolium chloride and 345 μl of triethylamine, followed by stirring at 60° C. for 30 minutes. After being allowed to cool down, the reaction mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 10% ethyl acetate/n-hexane), whereby 105 mg of the title compound were obtained as a low polar fraction in the form of a pale yellow solid and 128 mg of methyl 4-[4-[2-(5,6,7,8-tetrahydro-5,5-dimethylquinoxalyl)]-4-oxo-1-butanoyl] benzoate were obtained as a high polar fraction in the form of a pale yellow solid.

Low polar fraction:

H-NMR (CDCl$_3$, 400 MHz) δ; 1.36(s,6H), 1.80–1.86(m, 2H), 1.93–2.00(m,2H),3.02(t,J=6.4 Hz,2H), 3.47(t,J=6.4 Hz,2H), 3.64(t,J=6.4 Hz,2H), 3.96(s,3H), 8.08(d,J=8.8 Hz,2H), 8.14(d,J=8.8 Hz,2H), 9.00(s,1H).

High polar fraction:

$^1$H-NMR (CDCl$_3$, 400 MHz) δ; 1.39(s,6H), 1.82–1.86(m, 2H), 1.94–2.00(m,2H), 3.03(t,J=6.8 Hz,2H), 3.47(t,J=6.4 Hz,2H), 3.69(t,J=6.4 Hz,2H), 3.96(s,3H),8.08(d,J=8.8 Hz,2H), 8.14(d,J=8.8 Hz,2H), 8.92(s,1H).

Step 2

4-{2-{5-[2-(5,6,7,8-tetrahydro-8,8-dimethynquinoxalyl)]pyrrolfyl}}benzoic acid

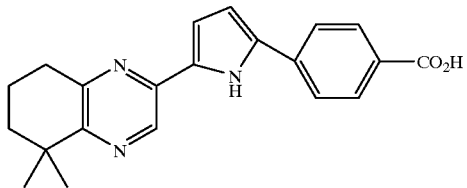

Methyl 4-[4-[2-(5,7,8-tetrahydro-8,8-dimethylquinoxalyl)]-4-oxo-1-butanoyl]benzoate (105 mg) was treated in a similar manner to Steps 4 and 5 of Example 1, whereby 67 mg of the title compound were obtained in the form of a yellow solid.

$^1$H-NMR (DMSO-$d_6$, 400 MHz) δ; 1.28(s,6H), 1.73–1.78(m,2H), 1.84–1.91(m,2H), 2.90–2.95(m,2H), 6.19(dd,J=2.4,3.6 Hz,1H), 6.94(dd,J=2.0,3.6Hz)z,1H), 7.91(d,J=8.8 Hz,2H), 7.95(d,J=8.4 Hz,2H), 8.88(s,1H), 11.72(br s,1H).

Example 16

4-{2-{5-[2-(5,6,7,8-Tetrahydro-8,8-dimethylquinoxalyl)]pyrrolyl}}benzoic acid

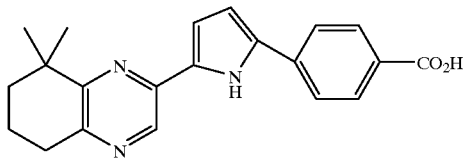

Methyl 4-[4-[2-(5,6,7,8-tetrahydro-8,8-dimethylquinoxalyl)]-4-oxo-1-butanoyl]benzoate (128 mg) was treated in a similar manner to Steps 4 and 5 of Example 1, whereby 76 mg of the title compound were obtained in the form of a yellow solid.

$^1$H-NMR (DMSO-$d_6$, 400 MHz) δ; 1.35(s,6H), 1.72–1.77 (m,2H), 1.80–1.88(m,2H), 2.82–2.88(m,2H), 6.80–6.83(m, 1H), 6.93–6.98(m,1H), 7.89–7.96(m,4H), 8.83(s,1H), 11.54 (br s,1H).

Example 17

4-{2-{5-[5-(1-Isopropyl-2,3-dimethylindolyl)] pyrrolyl}}benzoic acid

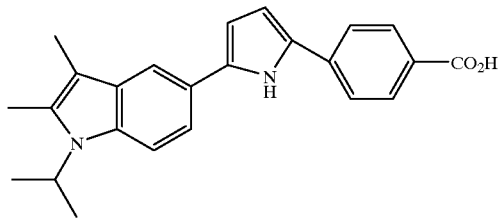

Step 1

1-[5-(1-Isopropyl-2,3-dimethylindolyl)]-1-oxo-2-propene

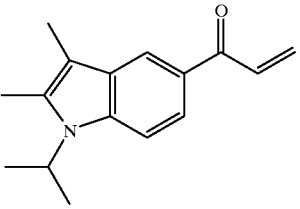

In anhydrous tetrahydrofuran were dissolved 2.2 g of 1-isopropyl-2,3-dimethylindoline-5-carbaldehyde, followed by dropwise addition of 13 ml of vinyl magnesium bromide (1.0 M) under ice cooling. The resulting mixture was stirred at room temperature for 30 minutes. A saturated aqueous solution of ammonium chloride was added to the reaction mixture and the resulting mixture was extracted with ethyl acetate. The organic layer was dried over anhydrous magnesium sulfate, followed by concentration under reduced pressure. The secondary alcohol derivative so obtained was dissolved in 30 ml of acetone, followed by the addition of 12 g of manganese dioxide. The resulting mixture was stirred at room temperature for 12 hours. Manganese dioxide was filtered out through Celite. The solvent was distilled off. The residue so obtained was subjected to chromatography on a silica gel column, whereby 1.4 g of the title compound was obtained.

$^1$H-NMR (CDCl$_3$, 400 MHz) 1.61(d,J=7.2 Hz,6H), 2.28 (s,3H), 2.38(s,3H), 4.66(hept.,J=7.2 Hz, 1H), 5.75(dd,J=2.0, 10.4 Hz,1H), 6.37(dd,J=2.0,16.8Hz,1H), 7.34(dd,J=10.4, 16.8 Hz,1H), 7.46(d,J=9.2 Hz,1H), 7.79(brd,J=9.2 Hz,1H), 8.18(d,J=1.6 Hz,1H).

Step 2

4-{2-{5-[5-(1-Isopropyl-2,3-dimethylindolyl)] pyrrolyl}}benzoic acid

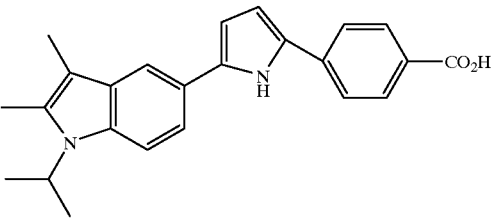

1-[5-(1-Isopropyl-2,3-dimethylindolyl)]-1-oxo-2-propene was treated in a similar manner to Step 2 (process 1) and Step 3 of Example 6, whereby the title compound was obtained.

$^1$H-NMR (CDCl$_3$, 400 MHz) δ; 1.62(d,J=7.2 Hz,6H), 2.29(s,3H), 2.39(s,3H), 4.66(hept.,J=6.8 Hz, 1H), 6.57(t,J= 3.6 Hz,1H), 6.77(t,J=2.8 Hz,1H), 7.18(br s,1H), 7.33(dd,J= 1.6,8.4 Hz,1H), 7.47(d,J=8.4 Hz,1H), 7.62(d,J=8.4 Hz,2H), 8.12(d,J=8.4 Hz,2H), 8.72(br s,1H).

Example 18

4-[5-[2-[2-(5,6,7,8-Tetrahydro-5,5,8,8-tetramethylquinoxalyl)]imidazolyl]]benzoic acid

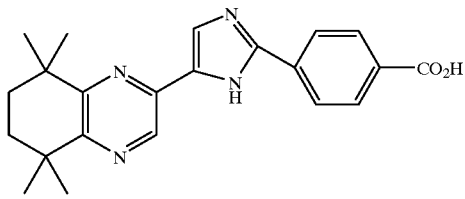

Step 1

2-Bromoacetyl-5,6,7,8-tetrahydro-5,5,8,8-tetramethylquinoxaline

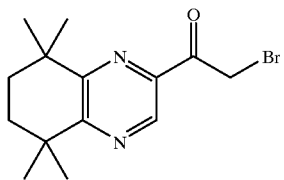

In 5 ml of ethyl acetate were dissolved 1.08 g of cupric bromide. To the resulting solution was added a solution of 700 mg of 2-acetyl-5,6,7,8-tetrahydro-5,5,8,8-tetramethylquinoxaline in 5 ml of chloroform, followed by heating under reflux for 8 hours. After being allowed to cool down, the reaction mixture was added with water and the resulting solution was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/n-hexane), whereby 815 mg of the title compound were obtained in the form of a pale yellow oil.

$^1$H-NMR (CDCl$_3$, 400 MHz) δ; 1.35(s,6H), 1.36(s,6H), 1.84(s,4H), 4.75(s,2H), 9.01(s,1H).

Step 2

4-[5-[2-[2-(5,6,7,8-Tetrahydro-5,5,8,8-tetramethylquinoxalyl)]imidazolyl]]benzoic acid

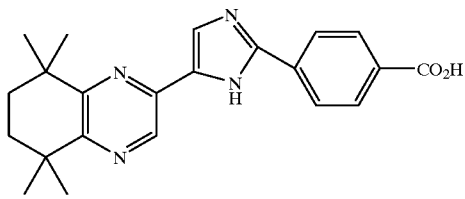

In 10 ml of N,N-dimethylformarnide were dissolved 615 mg of 2-bromoacetyl-5,6,7,8-tetreahydro-5,5,8,8-tetramethylquinoxaline. To the resulting solution were added 370 mg of methyl 4-amidinobenzoate and 958 mg of potassium carbonate, followed by heating under reflux for 2 hours. After the reaction mixture was allowed to cool down, water added thereto. The resulting mixture was then extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 20% ethyl acetate/n-hexane), whereby 100 mg of a yellow oil were obtained. The resulting oil was hydrolyzed in a similar manner to Step 5 of Example 1, whereby 70 mg of the title compound were obtained as a yellow solid.

Melting point: >300° C.; $^1$H-NMR (DMSO-d$_6$, 400 MHz) δ; 1.28(s,6H), 1.32(s,6H), 1.77(s,4H), 7.91(br s,1H), 8.03 (d,J=8.4 Hz,2H), 8.13(br d,J=8.0 Hz,2H), 8.91(s,1H), 13.15 (br s,1H).

Example 19

4-[4-[2-[2-(5,6,7,8-Tetrahydro-5,5,8,8-tetramethylquinoxalyl)]thiazolyl]]benzoic acid

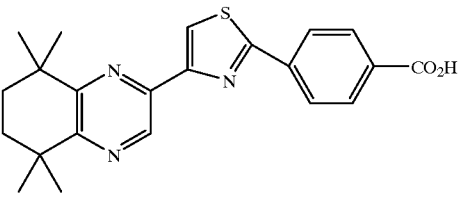

In 10 ml of isopropyl alcohol were dissolved 200 mg of 2-bromoacetyl-5, (5,7,8-tetrahydro-5,5,8,8-tetramethylquinoxaline. To the resulting solution, were added 132 mg of 4-carbomethoxybenzthioamide and 0.1 ml of pyridine, followed by heating under reflux for 2 hours. After the reaction mixture was allowed to cool down, water was added thereto. The resulting mixture was extracted with ethyl acetate. The organic layer was successively washed with water and saturated saline, dried over anhydrous magnesium sulfate and concentrated under reduced pressure. The residue so obtained was3 subjected to chromatography on a silica gel column (developing solvent: 5% ethyl acetate/n-hexane), whereby 135 mg of a colorless solid were obtained. The resulting solid was hydrolyzed in a similar manner to Step 5 of Example 1, whereby 117 mg of the title compound were obtained as a colorless solid.

Melting point: 262° C. (decomposed); $^1$H-NMR (DMSO-d$_6$, 400MHz) δ; 1.30(s,6H), 1.34(s,6H), 1.79(s,4H), 8.07(d, J=8.4 Hz,2H), 8.16(d, J8.0 Hz,2H), 8.45(s,1H), 9.12(s,1H).

Example 20

4-[5-[3-[2-(5,6,7,8-Tetraiydro-5,5,8,8-tetramethylquinoxalyl)l]pyrazolyl]]benzoic acid

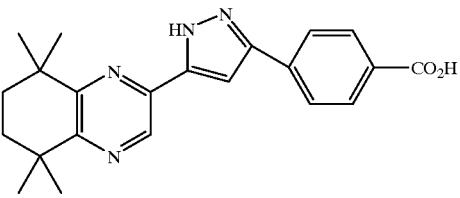

Step 1

Methyl 4-[3-[2-(5,6,7,8-Tetrahydro-5,5,8,8-tetramethylquinoxalyl)]-3-oxo-1-propanoyl]]benzoate

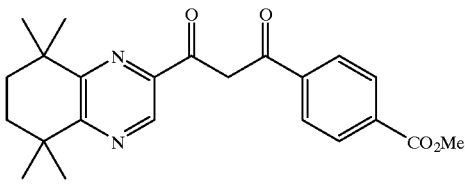

In 10 ml of tetrahydrofuran were dissolved 542 µl of diisopropylamine, followed by the dropwise addition of 1.94 ml of n-butyl lithium (1.6 M n-hexane solution) at 0° C. under a nitrogen gas stream. The resulting mixture was stirred for 30 minutes and then added dropwise to a solution of 600 mg of 2-acetyl-5,6,7,8-tetrahydro-5,5,8,8-tetramethylquionoxaline in 30 ml of tetrahydrofuran at −78° C., followed by stirring for 30 minutes. A solution of 564 mg of monomethyl terephthalate chloride in 10 ml of tetrahydrofuran was then added, followed by stirring. A saturated aqueous solution of amnonium chloride was added to the reaction mixture and the resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate-hexane), whereby 375 mg of a title compound were obtained in the form of a pale yellow solid.

Melting point: 158 to 160° C.; ¹H-NMR (CDCl₃, 400 MHz) δ; 1.37(s,6H), 1.41(s,6H), 1.85(s,4H), 3.96(s,3H), 7.54(s,1H), 8.06(d.J=8.8 Hz,2H), 8.16(d,J=8.8 Hz,2H), 9.10 (s,1H).

Step 2

4-[5-[3-[2-(5,6,7,8-tetrahydro-5,5,8,8-tetramethylquinoxalyl)l]pyrazolyl]]benzoic acid

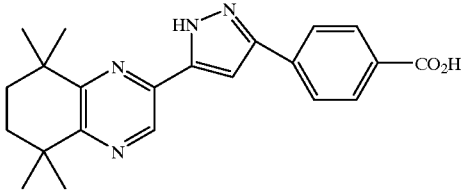

In 2 ml of acetic acid were dissolved 200 mg of methyl 4-[3-[2-(5,6,7,8-tetrahydro-5,5,8,8-tetramethylquinoxalyl)]-3-oxo-1-propanoyl]benzoate. To the resulting solution were added 38 mg of hydrazine monohydrate, followed by heating under reflux for 2 hours. After the reaction mixture was allowed to cool down, it was poured into a saturated aqueous solution of sodium bicarbonate. The resulting mixture seas extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/n-hexane), whereby 190 mg of a colorless solid were obtained. In a similar manner to Step 5 of Example 1, 70 g of the resulting solid were hydrolyzed, whereby 58 mg of the title compound were obtained in the form of a pale yellow solid.

Melting point: 295 to 298° C.; ¹H-NMR (DMSO-d₆, 400MHz) δ; 1.28(s,6H), 1.35(s,6H), 1.78(s,4H), 7.44(br s,1H), 7.92–8.04(m, 4H), 8.92(s,1H).

Example 21

4-[5-[3-[2-(5,6,7,8-Tetrahydro-5,5,8,8-tetramethylquinoxalyl)]-1-methylpyrazolyl]]benzoic acid

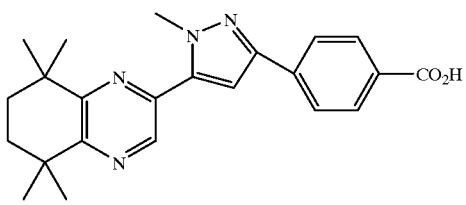

In 10 ml of N,N-dimethylformamide were dissolved 100 mg of methyl 4-[5-[3-[2-(5,6,7,8-tetrahydro-5,5,8,8-tetramethylquinoxalyl)pyrazolyl]]benzoate. To the resulting solution were added 15 mg of sodium hydride and 32 µl of methyl iodide at 0° C., followed by stirring for one hour. A saturated aqueous solution of ammonium chloride was added to the reaction mixture and the resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/n-hexane), whereby 75 mg of a colorless solid were obtained as a low polar fraction and 10 mg of a colorless oil were obtained as a high polar fraction. The high polar fraction was hydrolyzed in a similar manner to Step 5 of Example 1, whereby 58 mg of the title compound were obtained in the form of a pale yellow solid.

¹H-NMR (DMSO-d₆, 400 MHz) δ; 1.30(s,6H), 1.33(s, 6H), 1.80(s,4H), 4.22(s,3H), 7.50(s,1H), 7.91–8.02(m,4H), 8.90(s,1H).

Example 22

4-[3-[5-[2-(5,6,7,8-Tetrahydro-5,5,8,8-tetramethylquinoxanlyl)]-1-methylpyrazolyl]]benzoic acid

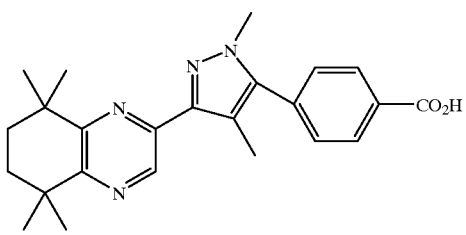

The low polar fraction obtained in Example 15 was hydrolyzed in a similar manner to Step 5 of Example 1, whereby 9 mg of the title compound were obtained as a colorless solid.

Melting point: 240 to 242°° C.; ¹H-NMR (DMSO-d₆, 400 MHz) δ; 1.29(s,6H), 1.31(s,6H), 1.78(s,4H), 3.98(s,3H), 7.06(s,1H), 7.77(d,J=8.4 Hz,2H), 8.05(d,J=8.4 Hz,2H), 8.89 (s,1H).

Example 23

4-[3-[5-[2-(5,6,7,8-Tetrahydro-5,5,8,8-tetramethylquinoxalyl)]isoxazolyl]]benzoic acid

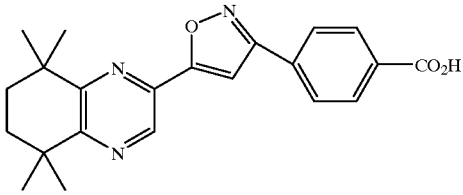

In 10 ml of ethanol were dissolved 80 mg of methyl 4-[3-[2-(5,6,7,8-tetrahydro-5,5,8,8-tetramethylquinoxalyl)]-3-oxo-1-propanoyl]benzoate. To the resulting solution were added 21 mg of hydroxyamine hydrochloride, followed by heating under reflux for 2 hours. After the reaction mixture was allowed to cool down, crystals so precipitated were collected by filtration and dried under reduced pressure, whereby 40 mg of a colorless solid were obtained. The resulting solid was hydrolyzed in a similar manner to Step 5 of Example 1, whereby 32 mg of the title compound were obtained in the form of a colorless solid.

$^1$H-NMR (DMSO-$d_6$, 400 MHz) δ; 1.31(s,6H), 1.36(s, 6H), 1.81(s,4H), 7.76(s,1H), 8.02–8.17(m,4H), 9.02(s,1H).

Example 24

4-{1-{5-[6-(1,2,3,4-tetrahydro-1-isopropylquinolyl)]pyrrolyl}}benzoic acid

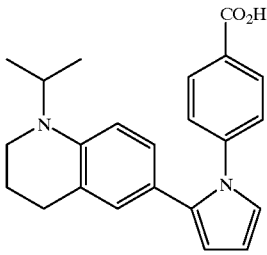

Step 1

1-[6-(1,2,3,4-Tetrahydro-1-isopropylquinolyl)]3-[2-(1,3-dioxolanyl)]propan-1-ol

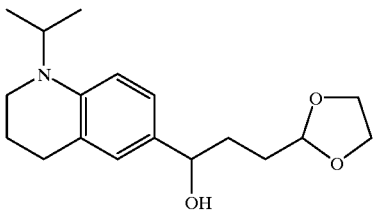

To 3 ml of anhydrous tetrahydrofuran were added 630 mg of a magnesium piece, followed by the addition of a small portion of 4.1 g of 2-(2-bromoethyl)-1,3-dioxolane. When the reaction started, a solution of the remaining portion of 2-(2-bromoethyl)-1,3-dioxolane in tetrahydrofuran was slowly added dropwise to prepare a Grignard reagent. After the resulting mixture was stirred at room temperature for 30 minutes, a 10 ml solution of 4.0 g of 1-isopropyl-1,2,3,4-tetrahydroquinoline-6-carbaldehyde in tetrahydrofuran was slowly added dropwise. The reaction mixture was stirred at room temperature for 30 minutes, followed by the addition of an aqueous solution of ammonium chloride. The resulting mixture was extracted with ethyl acetate. The organic layer was dried over anhydrous magnesium sulfate and then concentrated under reduced pressure. The title compound so obtained (4.0 g) was provided for the subsequent reaction without purification.

Step 2

1-[6-(1,2,3,4-Tetrahydro-1-isopropylquinolyl)]-1-oxo-3-[2-(1,3-dioxolanyl)]propane

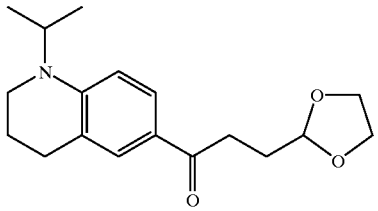

In 20 ml of acetone we,re dissolved 4.0 g of 1-[6-(1,2,3,4-tetrahydro-1-isopropylquinolyl)]-3-[2-(1,3-dioxolanyl)propan-1-ol obtained in Step 1. To the resulting solution were added 20 g of manganese dioxide, followed by stirring at room temperature overnight. The manganese dioxide was filtered out through Celite and the solvent was distilled off. The residue was subjected to chromatography on a silica gel column (developing solvent: 25% ethyl acetate/n-hexane), whereby 1.2 g of the title compound were obtained in the form of a reddish brown oil.

$^1$H-NMR (CDCl$_3$, 400 MHz) δ; 1.20(d,J=6.5 Hz,6H), 1.83–1.96(m,2H), 2.03–2.17(m,2H), 2.77(t,J=6.0 Hz,2H), 2.97(t,J=6.0 Hz,2H), 3.27(t,J=6.0 Hz,2H), 3.85(t,J=7.5 Hz,2H), 3.96(t,J=7.5 Hz,2H), 4.18(hept.,J=6.5 Hz,1H), 4.97 (t,J=5.0 Hz,1H), 6.63(d,J=10.0 Hz,1H), 7.60(br s,1H), 7.71 (br d,J=10.0 Hz, 1H).

Step 3

Methyl 4-{1-{5-[6-(1,2,3,4-tetrahydro-1-isopropylquinolyl)]pyrrolyl}}benzoate

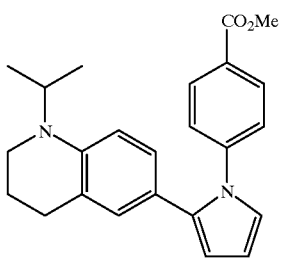

In 50 ml of toluene were dissolved 1.2 g of 1-[6-(1,2,3, 4-tetrahydro-1-isopropylquinolyl)]-1-oxo-3-[2-(1,3-dioxolanyl)]propane. To the resulting solution were added 650 mg of ethyl p-aminobeanzoate and 10 ml of acetic acid, followed by heating under reflux for 5 hours. The reaction mixture was washed with saturated saline, dried over anhydrous magnesium sulfate and concentrated under reduced pressure. The residue so obtained was subjected to chromatography on a silica gel column (developing solvent: 10% ethyl acetate/n-hexane), whereby 100 mg of the title compound were obtained in the form of a brown oil.

¹H-NMR (CDCl₃, 400 MHz) δ; 1.16(d,J=6.8 Hz,6H), 1.39(t,J=7.2 Hz,3H), 1.82–1.90(m,2H), 2.62(t, J=6.4 Hz,2H), 3.14(t,J=6.0 Hz,2H), 4.05(hept.,J=6.8 Hz,1H), 4.37 (q, J=7.2 Hz,2H), 6.29–6.30(m,1H), (3.34(t,J=3.4 Hz,1H), 6.51(d,J=8.4 Hz, 1H), 6.72(dd,J=2.0,8.8 Hz, 1H), 6.78(d,J= 2.0 Hz,1H), 6.89–6.90(m,1H), 7.23–7.27(m,2H), 7.97–8.05 (m,2H).

Step 4

4-{1-{5-[6-(1,2,3,4-Tetrahydro-1-isopropylquinolyl)]pyrrorlyl}}benzoic acid

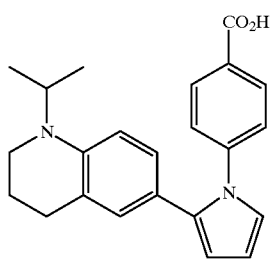

Methyl 4-{1-{5-[6-(1,2,3,4-tetrahydro-1-isopropylquinolyl)]pyrrolyl}}benzoate (100 mg) was hydrolyzed in a similar manner to Step 5 of Example 1, whereby 90 mg of the title compound were obtained in the form of yellow crystals.

¹H-NMR (CDCl₃, 400 MHz) δ; 1.16(d,J=6.4 Hz,6H), 1.83–1.90(m,2H), 2.62(t,J=6.4 Hz,2H), 3.15(t, J=6.0 Hz,2H), 4.05(hept.,J=6.4 Hz,1H), 6.30(br s,1H), 6.34–6.37 (m, 1H), 6.52(d,J=8.4 Hz,1H), 6.73((d,J=8.4 Hz,1H), 6.78 (br s,1H), 6.92(br s,1H), 7.27–7.30(m,2H), 8.03–8.05(m, 2H).

Example 25

4-(5,6-Diisopropyl-2-pyrazinecarbamoyl)benzoic acid

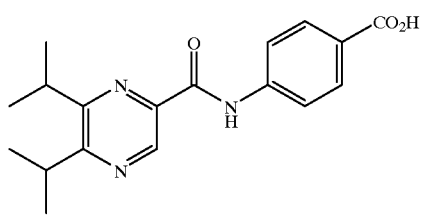

In 10 ml of tetrahydrofuran were dissolved 80 mg of 5,6-diisopropyl-2-pyrazinecarboxylic acid. To the resulting solution, 67 μl of diethyl chlorophosphate, 65 μl of triethylamine and a solution of 64 mg of ethyl p-aminobenzoate in 2 ml of tetrahydrofuran were successively added dropwise at 0° C. under a nitrogen gas stream. After the reaction mixture was allowed to rise back to room temperature, it was stirred overnight. Water was added to the reaction mixture and the resulting solution was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 2% ethyl acetate/n-hexane), whereby 90 mg of a colorless solid were obtained. The resulting solid was hydrolyzed in a similar manner to Step 5 of Example 1, whereby 31 mg of the title compound were obtained in the form of a colorless solid.

Melting point: 226–228° C.; ¹H-NMR (CDCl₃, 400 MHz) δ; 1.34(d,J=6.8 Hz,6H), 1.38(d,J=6.8 Hz,6H), 3.40–3.48(m, 2H), 7.87(d., J=8.8 Hz,2), 8.15(d,J=8.6 Hz,2H), 9.26(s,1H), 9.94(s,1H).

Example 26

6-[1-(4-Carboxybenzamido)]-1-isopropylindoline

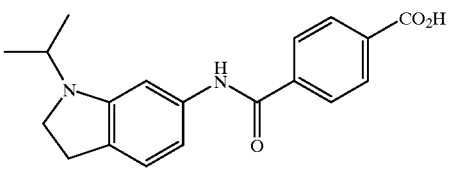

Step 1

1-Isopropyl-6-nitroindoline

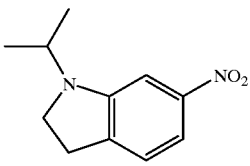

The title compound (6.0 g) was obtained in the form of yellow crystals by reacting 10 g of 6-nitroindoline with 20.7 g of 2-iodopropane and 16.9 g of potassium carbonate in N,N-dimethylformamide.

¹H-NMR (CDCl₃, 400 MHz) δ; 1.18(d,J=6.8 Hz,6H), 3.01(t,J=8.4 Hz,2H), 3.48(t,J=8.8 Hz,2H), 3.86(hept.,J=6.8 Hz,1H), 7.06(d,J=7.6 Hz,1H), 7.26(d,J=0.8 Hz,1H), 7.47 (dd,J=2.0,8.0 Hz,1H).

Step 2

6-[1-(4-Carbomethoxybenzamido)]-1-isopropylindoline

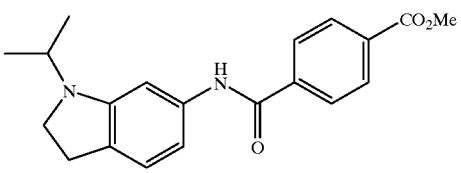

In 34 ml of tetrahydrofuran were dissolved 3.0 g of 1-isopropyl-6-nitroindoline. To the resulting solution were added 47 ml of aqueous ammonia and 34 ml of water, followed by the addition of 171 ml of an aqueous solution of 47 g of sodium hydrosulfite. The resulting mixture was stirred at room temperature for 3 hours, followed by extraction with ethyl acetate. The organic layer was dried over anhydrous magnesium sulfate and then concentrated under reduced pressure, whereby 2.0 g of brown crystals were obtained.

The crystals so obtained were dissolved in 30 ml of toluene. To the resulting solution were added 2.07 g of monomethyl terephthalate chloride and 5 ml of pyridine, followed by stirring at room temperature for 10 hours. Water was added to the reaction mixture and the resulting mixture was extracted with ethyl acetate. The organic layer was dried over anhydrous magnesium sulfate and concentrated under reduced pressure. The residue so obtained was subjected to chromatography on a silica gel column, whereby 800 mg of the title compound were obtained in the form of a colorless solid.

$^1$H-NMR (CDCl$_3$, 400 MHz) δ; 1.16(d,J=6.8 Hz,6H), 2.92(t,J=8.4 Hz,2H), 3.38(t,J=8.4 Hz,2H), 3.84(hept.,J=6.8 Hz,1H), 3.95(s,3H), 6.67(br d,J=7.6 Hz,1H), 6.94(br s, 1H), 6.99(d,J=7.6 Hz,1H), 7.80(br s,1H), 7.91(d,J=8.0 Hz,2H), 8.12(d,J=8.4 Hz,2H).

Step 3

6-[1- (4-Carboxybenzamido)]-1-isopropylindoline

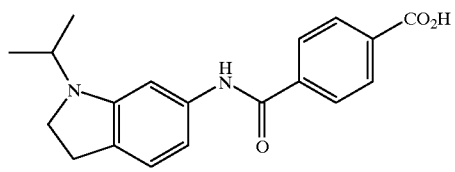

6-[1-(4-Carbomethoxybenzamido)]-1-isopropylindoline (800 mg) was hydrolyzed in a similar manner to Step 5 of Example 1, whereby 374 mg of the title compound were obtained in the form of a brown solid.

$^1$H-NMR (DMSO-d$_6$, 400 MHz) δ; 1.10(d,J=6.4 Hz,6H), 2.81(t,J=8.4 Hz,2H), 3.29(t,J=8.0 Hz,2H), 3.71(hept.,J=6.8 Hz,1H), 6.90–6.94(m,3H), 7.98–8.05(m,4H), 10.11(s,1H).

In a similar manner to the above-described process, the compounds which will be described below were prepared, respectively.

Example 27

4-[4-[2-[2-(5,6-Diisopropylpyrazinyl)]pyrrolyl]]benzoic acid

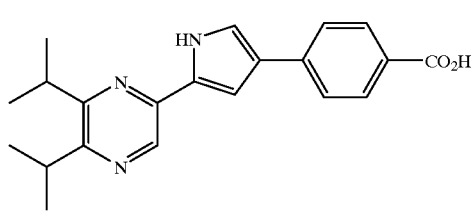

Melting point: 245° C. (decomposed); $^1$H-NMR (CDCl$_3$, 400 MHz) δ; 1.30(d,J=7.6 Hz,6H), 1.32(d,J=7.2 Hz,6H), 3.32–3.40(m,2H), 7.08(br s,1H), 7.:35(br s,1H), 7.67(d,J= 8.4 Hz,2H), 8.10(d,J=8.4 Hz, 2H), 8.70(s,1H), 9.58(br s,1H).

Example 28

4-[4-[2-[2-(5,5,7,7-Tetriamethylcyclopenta[b]pyrazinyl)]pyrrolyl]]benzoic acid

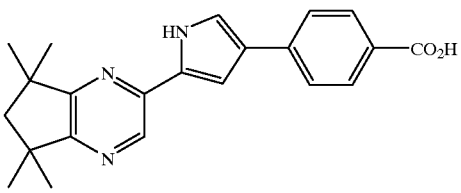

Melting point: 145 to 147° C.; $^1$H-NMR (CDCl$_3$, 400 MHz) δ; 1.38(s,6H), 1.40(s,6H), 2.01(s,2H), 7.10(s,1H), 7.35(s,1H), 7.67(d,J=8.0 Hz,2H), 8.10(d,J=8.8 Hz,2H), 8.72 (s,1H), 9.72(br s,1H).

Example 29

4-[3-[5-[2-(5,6,7,8-Tetrahydro-5,5,8,8-tetramethylquinoxalyl)]-2-methylpyrrolyl]]benzoic acid

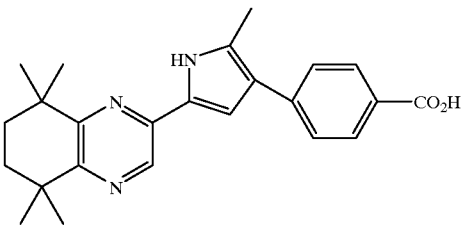

Melting point: 248 to 250° C.; $^1$H-NMR (DMSO-d6, 400 MHz) δ; 1.25(s,6H), 1.34(s,6H), 1.75(s;,4H), 7.11–7.14(m, 1H), 7.57(d, J=8.0 Hz,2H), 7.92(d,J=7.6 Hz,2H), 8.74(s, 1H).

Example 30

4-[4-[2-[2-(5,6-Diisopropylpyrazinyl)]thienyl]]benzoic acid

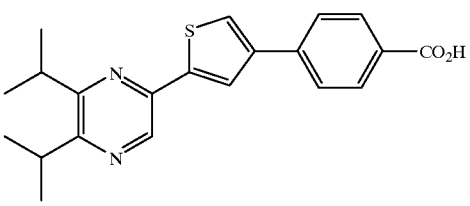

Melting point: 226 to 229° C.; $^1$H-NMR (CDCl$_3$, 400 MHz) δ; 1.31(d,J=6.8 Hz,6H), 1.34(d,J=6.8 Hz,6H), 3.32–3.42(m,2H), 7.65(br s,1H), 7.74(d,J=8.4 Hz,2H), 7.91 (br s,1H), 8.15(d,J=8.0 Hz, 2H), 8.75(s,1H).

Example 31

4-[4-[2-[2-(5,5,7,7,-Tetramethylcyclopenta[b]pyrazinyl)]thienyl]]benzoic acid

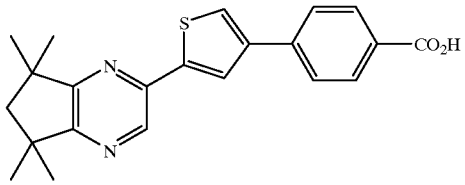

Melting point: 222° C. (decomposed); $^1$H-NMR (CDCl$_3$, 400 MHz) δ; 1.39(s,6H), 1.40(s,6H), 2.03(s,2H), 7.66(d,J=1.2 Hz,1H), 7.76(d, J=:8.0 Hz,2H), 7.96(d,J=1.2!Hz,1H), 8.17(d,J=8.4 Hz,2H), 8.76(s,1H).

Example 32

4-[3-[5-[2-(5,6,7,8-Tetrahydro-5,5,8,8-tetramethylquinoxalyl)]-2-methylthienyl]]benzoic acid

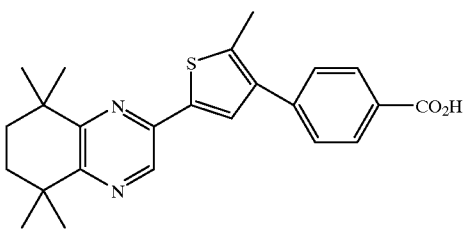

Melting point: 215 a 217° C.; $^1$H-NMR (DMSO-d$_6$, 400 MHz) δ; 1.27(s,6H), 1.29(s,6H), 1.76(s,4H), 2.54(s,3H), 7.62(d,J=8.8 Hz, 2H), 7.95(s,1H), 8.01(d,J=8.0 Hz,2H), 8.97(s,1H).

Example 33

4-[4-[2-[2-(5,6,7,8-tetreahydro-5,5,8,8-tetramethylquinoxalyl)]-1-isopropylpyrrolyl]]benzoic acid

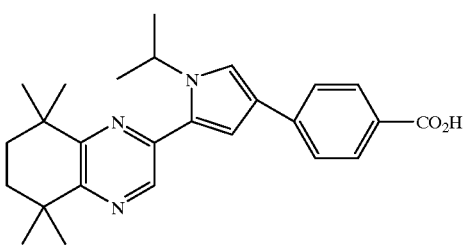

Melting point: 225 to 227° C.; $^1$H-NMR (DMSO-d$_6$, 400 MHz) δ; 1.28 (s,6H), 1.29(s,6H), 1.47(d,J=6.8 Hz,6H), 1.77(s,4H), 5.35–5.46(m,1H), 7.18(s,1H), 7.70–7.79(m,2H), 7.85–7.91(m,3H), 8.77(s,1H).

Example 34

4-[4-[2-[2-(5,6-Diisopropylpyrazinyh)]-1-methylpyrrolyl]]benzoic acid

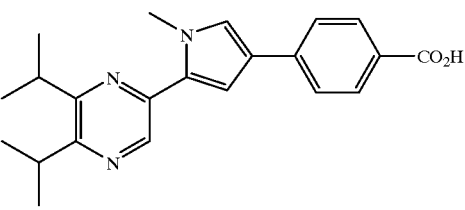

$^1$H-NMR (CDCl$_3$, 400 Hz) δ; 1.31(d,J=6.8 Hz,6H), 1.32(d,J=6.8 Hz,6H), 3.32–3.43(m,2H), 4.07(s, 3H), 6.96(d,J=2.0 Hz,1H), 7.17(d,J=1.6 Hz,1H), 7.62(d,J=8.4 Hz,2H), 8.07(d,J=8.4 Hz,2H), 8.68(s,1H).

Example 35

4-[4-[2-[2-(5,5,7,7-Tetramethylcyclopenta[b]pyrazinyl)]-1-methylpyrrolyl]]benzoic acid

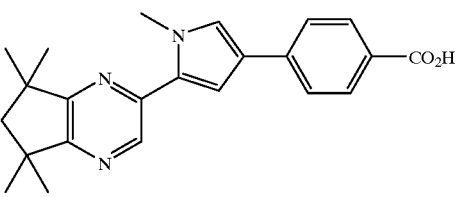

Melting point: 250° C. (decomposed); $^1$H-NMR (CDCl$_3$, 400 MHz) δ; 1.38(s,6H), 1.39(s, 6H), 2.03(s,2H, 4.04(s,3H), 6.94(s,1H), 7.19(s,1H), 7.62(d,J=8.0Hz,2H), 8.08(d,J=8.0Hz,2H), 8.67(s,1H).

Example 36

4-[2-[2-(5,6-Diisopropylpyrazinyl)-]-1-ethylpyrrolyl]]benzoic acid

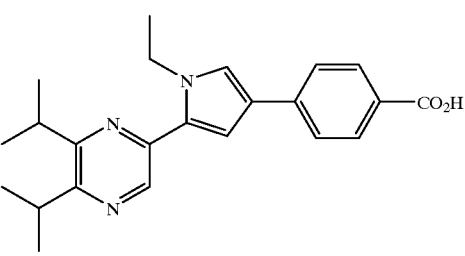

Melting point 272 to 274° C.; $^1$H-NMR (CDCl$_3$, 400 MHz) δ; 1.30(d,J=6.4 Hz,6H), 1.32(d,J=6.0 Hz,6H), 1.44(t, J=7.2 Hz,3H), 3.30–3.42(m,2H), 4.53(q,J=7.2 Hz,2H), 6.96 (br s,1H), 7.22(br s,1H), 7.61(d,J=8.4 Hz,2H). 8.08(d,J=3.4 Hz,2H), 8. 68(s,1H)

Example 37

4-[3-[1,2-Dimethyl-5-[2-(5,6,7,8-tetrahydro-5,5,8,8,-tetramethylquinoxalyl)pyrrolyl]]benzoic acid

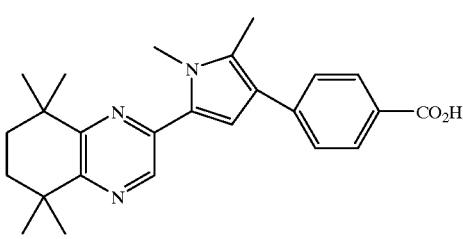

Melting point: 265 to 267° C.; $^1$H-NMR (DMSO-d$_6$, 400 MHz) δ; 1.28(s,6H), 1.31(s,6H), 1.77(s,4H), 2.40(s,3H), 3.90(s,3H), 6.94(s,1H), 7.51(d,J=8.1 Hz,2H), 7.94(d,J=8.4 Hz,2H), 8.73(s,1H).

Example 38

4-[4-[2-[2-(5,6-Diisopropylpyrazinyl)]furyl]]benzoic acid

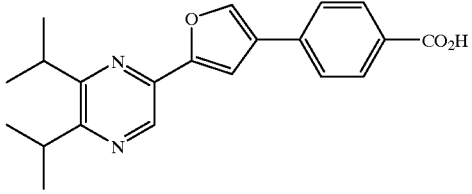

Melting point: 215 to 218° C.; $^1$H-NMR (DMSO-d$_6$, 400 MHz) δ; 1.23(d,J=6.8 Hz,6H), 1.28(d,J=15.8 Hz,6H), 3.38–3.43(m,2H), 7.71(s,1H), 7.83(d,J=8.8 Hz,2H), 7.96(d, J=8.8 Hz,2H), 8.53(s,1H), 8.81(s, 1H).

Example 39

4-[4-[2-[2-(5,5,7,7-Tetramethylcyclopenta[b]pyrazinyl)]-furyl]]benzoic acid

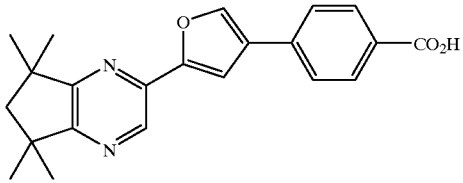

Melting point: 250 to 252° C.; $^1$H-NMR (CDCl$_3$, 400 MHz) δ; 1.39(s,6H), 1.40(s,6H), 2.03(s,2H), 7.48(s,1H), 7.68(d,J=8.4 Hz, 2H), 7.94(s,1H), 8.14(d,J=8.4 Hz,2H), 8.78(s,1H).

Example 40

4-[3-[5-[2-(5,6,7,8-Tetrahydro-5,5,8,8-tetramethylquinoxalyl)]-2-methylfuryl]]benzoic acid

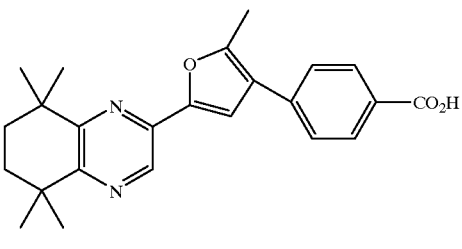

Melting point: 270 to 272° C.; $^1$H-NMR (DMSO-d$_6$, 400 MHz) δ; 1.28(s,6H), 1.31(s,6H), 1.77(s,4H), 2.56(s,3H), 7.49(s,1H), 7.67(d,J=7.2 Hz,2H), 7.99(d,J=7.2 Hz,2H), 8.75 (d,J=1.6 Hz,1H).

Example 41

4-[4-[2-[2-(5,6,7,8-tetrahydro-5,5,8,8-tetramethylquinoxalyl)]-1-(3-pyridylmethyl)pyrrolyl]]benzoic acid

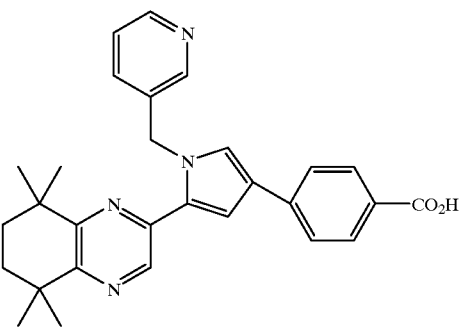

Melting point: 263 to 266° C.; $^1$H-NMR (CDCl$_3$, 400 MHz) δ; 1.09(s,6H), 1.32(s,6H), 1.74(br s,4H), 5.85(s,2H), 7.08(d,J=1.6 Hz,1H), 7.19(d,J=1.6 Hz,1H), 7.20–7.28(m, 2H), 7.35–7.38(m,1H), 7.62(d,J=8.4 Hz,2H), 8.07(d,J=8.4 Hz,2H), 8.45–8.48(m,1H), 8.49–8.53(m,1H), 83.73(s,1H).

Example 42

4-[2-[5-[2-(5,6-Diisopropylpyrazinyl)]pyrrolyl]]benzoic acid

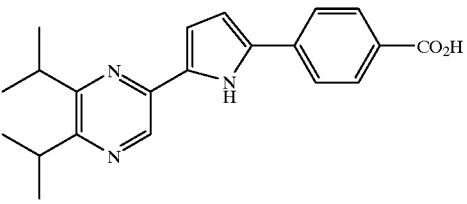

Melting point: 246° C. (decomposed); $^1$H-NMR (CDCl$_3$, 400 MHz) δ; 1.31(d,J=6.8 Hz,6H), 1.36(d,J=6.8 Hz,6H), 3.32–3.42(m,2H), 6.76(br s,1H), 6.82(br s,1H), 7.65(d,J=8.0 Hz,2H), 8.14(d,J=8.4 Hz,2H), 8.67(s,1H).

Example 43

4-[2-[5-[2-(5,5,7,7-Tetramethylcyclopenta[b]pyrazinyl)]-pyrrolyl]]benzoic acid

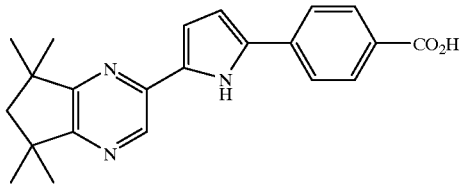

Melting point: 269° C. (decomposed); ¹H-NMR (DMSO-$d_6$, 400 MHz) δ; 1.29(s,6H), 1.35(s,6H), 1.96(s,2H), 6.82(br s,1H), 6.94(br s,1H), 7.93(br s,4H), 8.88(br s,1H).

Example 44

4-[2-[5-[2-(5,8-Dirriethyl-5,6,7,8-tetrahydroquinolyl)]pyrrolyl]]benzoic acid

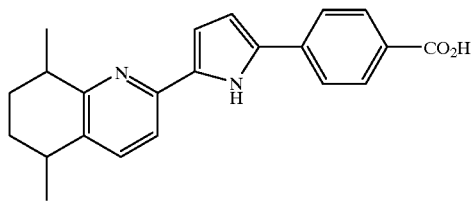

¹H-NMR (DMSO-$d_6$, 400 MHz) δ; 1.23, 1.24(2×d,J=(5.9 Hz,3H), 1.36, 1.39(2×d,J=6.8 Hz,3H), 1.40–1.74(m,2H), 1.80–2.08(m,2H), 2.83–2.94(m,2H), 6.76(m,1H), 6.80(m,1H), 7.55–7.63(m,2H), 11.34(br s,1H).

Example 45

6-[2-[5-[2-(5,6,7,8-Tetrahydro-5,5,8,8-tetramethylquinoxalyl)]pyrrolyl]]nicotinic acid

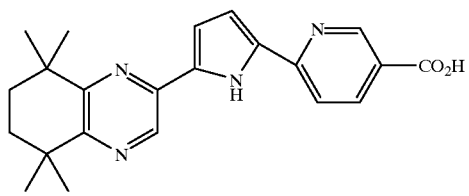

Melting point: 278° C. (decomposed); ¹H-NMR (DMSO-$d_6$, 400 MHz) δ; 1.27(s,6H), 1.34(s,6H), 1.77(s,4H), 7.00(dd,J=2.4,4.0Hz,1H), 7.09(dd,J=2.4,3.6 Hz,1H), 7.94(dd,J=0.4,8.4 Hz,1H), 8.21(dd,J=2.4,8.4 Hz,1H), 8.97(s,1H), 9.03(dd,J=0.8,2.0 Hz,1H), 11.67(br s,1H).

Example 46

4-[2-[5-[2-(5,6,-Diisopropylpyrazinyl)]thienyl]]benzoic acid

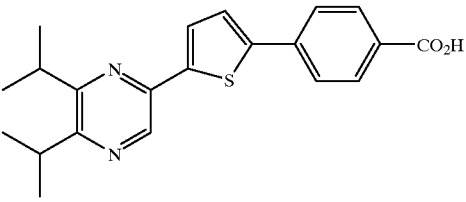

Melting point: 270 to 272° C.; ¹H-NMR (CDCl₃, 400 MHz) δ; 1.31(d,J=6.8 Hz,6H), 1.34(d,J=6.8 Hz,6H), 3.33–3.41(m,2H), 7.46(d,J=4.0 Hz,1H), 7.61(d,J=4.0 Hz,1H), 7.78(d,J=8.4 Hz,2H), 8.12(d,J=8.0 Hz,2H), 8.73(s, 1H).

Example 47

4-[2-[5-[2-(5,5,7,7-Tetramethylcyclopenta[b]pyrazinyl)]-thienyl]]benzoic acid

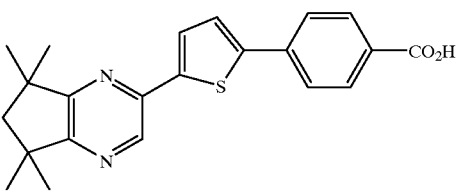

Melting point: 275° C. (decomposed); ¹H-NMR (CDCl₃, 400 MHz) δ; 1.38(s,6H), 1.40(s,6H), 2.03(s,2H), 7.46(d,J=3.6 Hz,1H), 7.64(d, J=3.6 Hz,1H), 7.77(d,J=8.4 Hz,2H), 8.13(d,J=8.4 Hz,2H), 8.74(s,1H).

Example 48

4-[2-[5-[2-(5,6-Diisopropropylpyrazinyl)]furyl]]benzoic acid

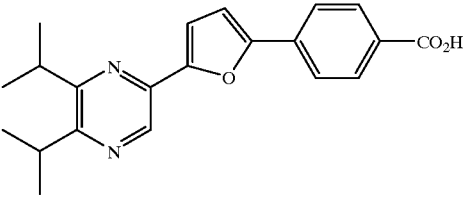

Melting point: 260 to 262° C.; ¹H-NMR (CDCl₃, 400 MHz) δ; 1.32(d,J=6.0 Hz,6H), 1.33(d,J=6.0 Hz,6H), 3.35–3.42(m,2H), 6.95(d,J=3.6 Hz,1H), 7.21(d,J=3.2 Hz,1H), 7.83(d,J=8.4 Hz,2H), 8.14(d,J=8.0 Hz,2H), 8.84(s, 1H).

Example 49

4-[2-[5-[2-(5,5,7,7-Tetramethylcyclopenta[b]pyrazinyl)]-furyl]]benzoic acid

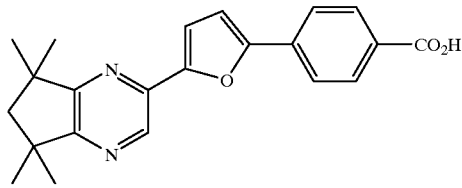

Melting point: 238 to 240° C.; $^1$H-NMR (DMSO-$d_6$, 400 MHz) δ; 1.31(s,6H), 1.33(s,6H), 1.98(s,2H), 7.32(br s,2H), 7.99(br s,4H), 8.95(br s,1H).

Example 50

4-[2-[5-[2-(5,5,7,7-Tetrarmethylcyclopenta[b]pyrazinyl)]-1-methylpyrrolyl]]benzoic acid

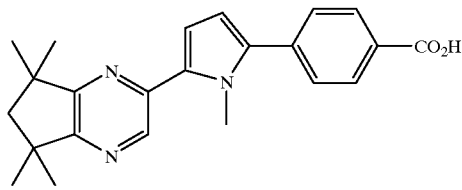

Melting point: 218 to 220° C.; $^1$H-NMR (DMSO-$d_6$, 400 MHz) δ; 1.31(s,6H), 1.33(s,6H), 1.99(s,2H), 3.85(s,3H), 6.43(d,J=4.0 Hz, 1H), 6.78(d,J=4.0 Hz,1H), 7.64(d,J=8.0 Hz,2H), 7.99(d,J=8.4 Hz,2H), 8.72(s,1H).

Example 51

4-[2-[5-[2-(5,6-Diisopropylpyrazinyl)]-1-isopropylpyrrolyl]]benzoic acid

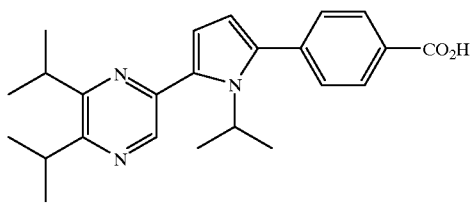

Melting point: 215° C. (decomposed); $^1$H-NMR (DMSO-$d_6$, 400 MHz) δ; 1.23(d,J=6.8 Hz,6H), 1.26(d,J=7.0 Hz,6H), 1.38(d,J=7.0 Hz,6H), 3.28–3.45(m,2H), 4.72–4.80(m,1H), 6.19(d,J=3.6 Hz,1H), 6.59(d,J=3.6 Hz,1H), 7.54(d,J=8.4 Hz,2H), 7.98(d,J==8.4 Hz,2H), 8.63(s,1H).

Example 52

4-[4-[2-[2-(5,6-Diisopropylpyrazinyl)]thiazolyl]]benzoic acid

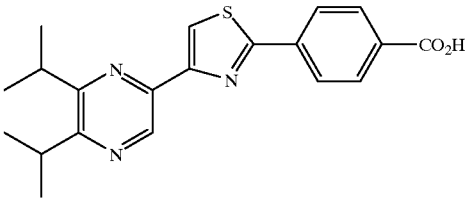

Melting point: 225 to 227° C.; $^1$H-NMR (DMSO-$d_6$, 400 MHz) δ; 1.25(d,J=6.8 Hz,6H), 1.29(d,J=:7.0 Hz,6H), 3.36–3.50(m,2H), 8.08(d,J=8.0 Hz,2H), 8.17(d,J=8.4 Hz,2H), 8.44(s,1H), 9.12(s,1H).

Example 53

4-{2-{5-[2-[5,6,7,8-Tetrahydro-3,5,8,8-pentamethylquinoxalyl)]]pyrrolyl}}benzoic acid

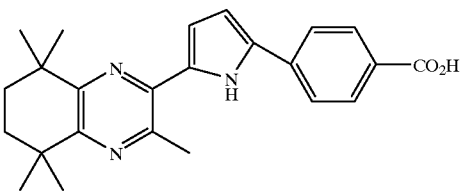

$^1$H-NMR (DMSO-$d_6$, 400 MHz) δ; 1.27(s,6H), 1.36(s, 6H), 1.76(s,4H), 2.63(s,3H), 6.71(dd,J=2.4, 4.0 HZ,1H), 6.83(dd, J=2.8,3.6 Hz,1H), 7.86(d,J=8.4 Hz,2H), 7.94(d, J=8.4 Hz,2H), 11.16(br s,1H).

Example 54

6-{2-{5-[2-[5,6,7,8-Tetrahydro-3,5,5,8,8-pentamethylquinoxalyl)]pyrrolyl}}nicotinic acid

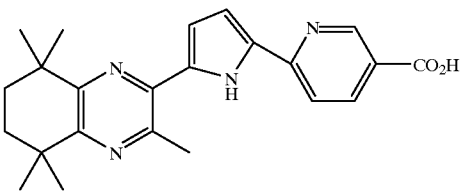

$^1$H-NMR (DMSO-$d_6$, 400 MHz) δ; 1.27(s,6H), 1.34(s, 6H), 1.77(s,4H), 2.66(s,3H), 6.78–6.82(m,1H),7.12–7.15(m, 1H), 7.94(dd,J=0.8,8.4 Hz,1H), 8.22(dd,J=2.0,8.4 Hz, 1H), 9.03(dd,J=0.8,2.4 Hz,1H).

Example 55

4-{2-{5-[2-(5,8-Dimethyl-5,6,7,8-tetrahydroquinolyl)]pyrrolyl}}benzoic acid

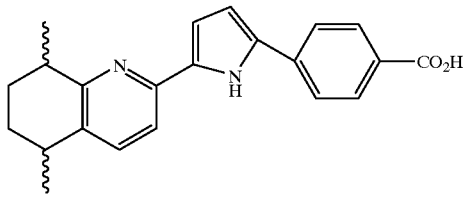

¹H-NMR (DMSO-d₆, 400 MHz) δ; 1.23, 1.24(2×d, J=6.9 Hz,3H), 1.36, 1.39(2×d,J=6.8 Hz,3H), 1.40–1.74(m,2H), 1.80–2.08(m,2H), 2.83–2.94(m, 2H), 6.76(m,1H), 6.80 (m, 1H), 7.55–7.63(m,2H), 11.34(br s,1H).

¹H-NMR(DMSO-d₆, 400 MHz) δ; 1.25(m,3H), 1.38(m, 3H),1.50–2.10(m,4H), 2.82–2.95(m,2H), 6.80(m,2H), 7.95 (m,6H).

Example 56

4-{2-{5-[2-(8-Isopropyl-5-Methyl-5,6,7,8-tetrahydroquinolyl)]pyrrolyl}}benzoic acid

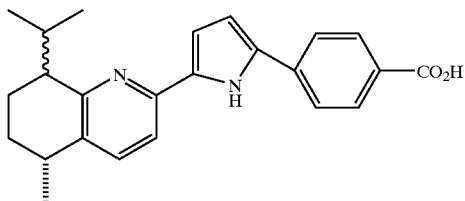

¹H-NMR (DMSO-d₆, 400 MHz) δ; 0.62(m,3H), 1.02, 1.06(2×d,J=6.8 Hz,total 3H), 1.22(d,J=6.83 Hz,3H), 1.30–2.01(m,4H), 2.74–3.02(m,3H), 6.84(m,2H), 7.82–8.04 (m,6H).

Example 57

4-{2-{5-[2-(5,5,7,7-tetramethyl-5,6,7,8-tetrahydroquinolyl)]pyrrolyl}}benzoic acid

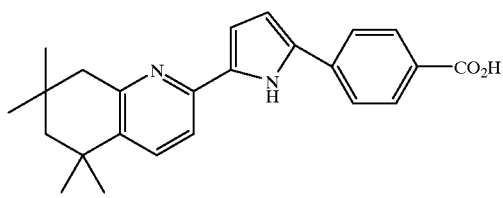

¹H-NMR (DMSO-d₆, 400 MHz) δ; 1.03(s,6H), 1.33(s, 6H), 1.63(s,2H), 2.98(s,2H), 6.98(m,2H), 7.42(m,1H), 7.96 (d,J=8.4 Hz,2H), 8.06(d,J=8.4 Hz,2H), 8.18(m,1H).

Example 58

4-{2-{5-[2-(8-Isopropyl-4-methoxyquinolyl)]pyrrolyl}}benzoic acid

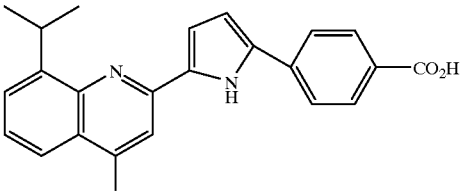

¹H-NMR (DMSO-d₆, 400 MHz) δ; 1.33(d,J=7.0 Hz,6H), 4.11(s,3H, 4.47(hept.,J=6.8 Hz,1H), 6.86(dd,J=1.6,3.6 Hz,1H), 7.14(dd,J=2.0,3.6 Hz,1H), 7.39(t,J=7.6 Hz,1H), 7.53(s,1H), 7.57(dLd,J=0.8,7.2 Hz,1H), 7.90(dd,J=1.2,8.0 Hz,1H), 7.93(d,J=8.8 Hz,2H), 7.97(d,J=8.8 Hz,2H), 11.56 (br s,1H).

Example 59

4-{2-{5-[2-(4-Chloro-8-isopropylquirolyl)]pyrrolyl}}benzoic acid

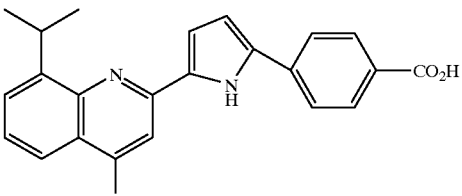

¹H-NMR (DMSO-d₆, 400 MHz) δ; 1.35(d,J=7.0 Hz,6H), 4.49(hept.,J=7.0 Hz,1H), 6.83–6.85(m,1H), 7.19(dd,J=2.0, 3.6 Hz,1H), 7.58(t,J=8.4 Hz,1H), 7.64–7.66(m,1H), 7.86–8.00(m,5H), 8.36(s,1H), 11.71(br s,1H).

Example 60

4-{2-{5-[2-(8-Isopropyl-4-methylquinolyl)]pyrrolyl}}benzoic acid

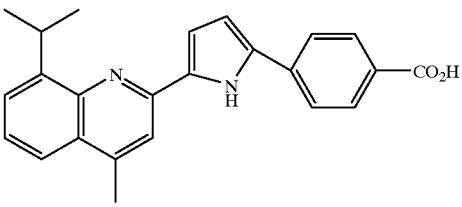

¹H-NMR (DMSO-d₆, 400 MHz) δ; 1.34(d,J=6.8 Hz,6H), 2.69(s,3H), 4.50–4.60(m,1H), 6.85–6.88(m,1H), 7.07–7.10 (m,1H), 7,47)t,J=7.6 Hz,1H), 7.59–7.62(m,1H), 7.82–7.85 (m,1H), 7.93(s,1H), 7.96(s,4H).

Example 61

4-{2-{5-[2-(4-Ehtyl-8-isopropylquinolyl)]pyrrolyl}}benzoic acid

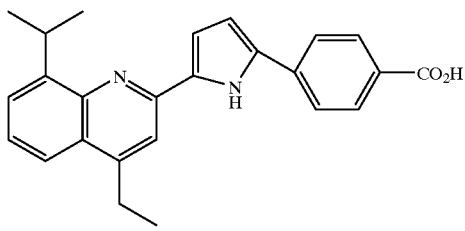

$^1$H-NMR (DMSO-$d_6$, 400 MHz) δ; 1.33(d,J=7.2Hz,6H), 1.36(t,J=7.6 Hz, 3H), 3.10(q,J=7.6Hz,2H), 4.50–4.58(m,1H), 6.84–6.88(m,1H), 7.08–7.12(m,1H), 7.46(t,J=8.0 Hz, 1H), 7.56–7.60(m,1H), 7.86–8.00(m,6H), 11.57(br s,1H).

Example 62

4-{2-{5-[2-(8-Isopropyl-4-phenylquinolyl)]pyrrolyl}}benzoic acid

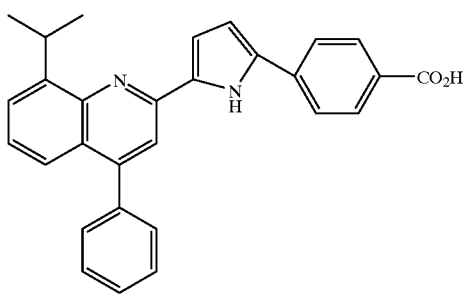

$^1$H-NMR (DMSO-$d_6$, 400 MHz) δ; 1.38(d,J=7.0 Hz,6H), 4.53(hept.J=6.8 Hz,1H), 6.86–6.89(m,1H), 7.16–7.19(m,1H), 7.39–7.43(m,1H), 7.52–7.64(m,7H), 7.94(s,4H), 8.07(s,1H), 11.67(br s,1H).

Example 63

4-{2-{5-[2-(4-Ethoxy-8-isopropylquincolyl)]pyrrolyl)}}benzoic acid

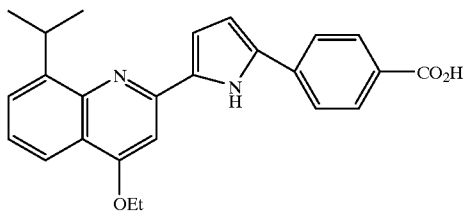

$^1$H-NMR (DMSO-$d_6$, 400 MHz) δ; 1.33(d,J=6.8 Hz,6H), 1.52(t,J=7.0 Hz,3H), 4.37–4.45(m,3H), 6.87–6.94(m,1H), 7.16–7.26(m,1H), 7.38–7.47(m,1H), 7.52–7.68(m,2H), 7.90–8.04(m,5H).

Example 64

4-{2-{5-[2-(4-Isopropoxy-8-isopropylquinolyl)]pyrrolyl}}benzoic acid

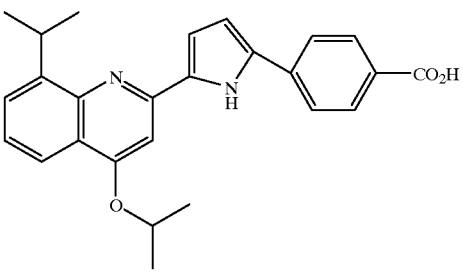

$^1$H-NMR (DMSO-$d_6$, 400 MHz) δ; 1.33(d,J=6.8 Hz,6H), 1.45(d,J=E6.0 Hz,6H), 4.40–4.50(m,1H), 5.07–5.14(m,1H), 6.83–6.88(m,1H), 7.11–7.15(m,1H), 7.37(t,J=7.6 Hz,1H), 7.51(s,1H), 7.56(d,J=6.8 Hz,1H), 7.89(d,J=3.4 Hz,1H), 7.92(d,J=8.4 Hz,2H), 7.97(d,J=3.4 Hz,2H), 11.52(s,1H), 12.80–12.88(m,1H).

Example 65

4-{2-{5-[2-(8-Ethyl-4-methoxyquinolyl)]pyrrolyl}}benzoic acid

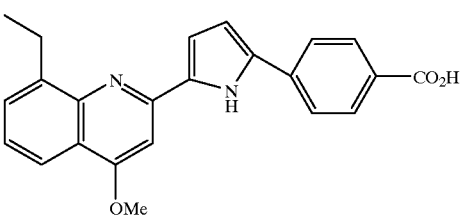

$^1$H-NMR DMSO-$d_6$, 400 MHz) δ; 1.32(t,J=7.2 Hz,3H), 3.29–3.38(m,2H), 4.16(s,3H), 6.89–6.94(m,1H), 7.20–7.30(m,1H), 7.38–7.45(m,1H), 7.55–7.63(m,2H), 7.90–8.00(m,5H).

Example 66

4-{2-{5-[2-(8-Ethyl-4-methylquinolyl)]pyrrolyl}}benzoic acid

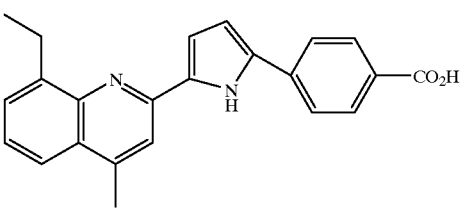

$^1$H-NMR (DMSO-$d_6$, 400 MHz) δ; 1.32(t,J=7.2 Hz,3H), 2.69(s,3H), 3.32–3.40(m,2H), 6.84–6.88(m,1H), 7.06–7.10(m,1H), 7.40–7.45(m,1H), 7.54–7.58(m,1H), 7.82–7.86(m,1H), 7.92(s,1H), 7.95(s,4H), 11.53(,br s,1H).

Example 67

4-{2-{5-[2-(4-Methoxy-8-methylquinolyl)]pyrrolyl}}benzoic acid

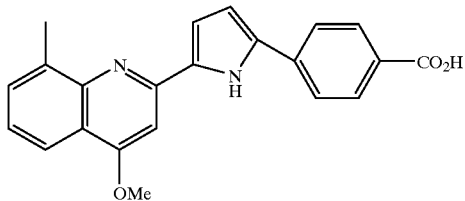

¹H-NMR (DMSO-d₆, 400 MHz) δ; 2.79(s,3H), 4.11(s, 3H), 6.84–6.88(m,1H), 7.13–7.17(m,1H), 7.32(t, J=7.6 Hz,1H, 7.49(s,1H), 7.52–7.56(m,1H), 7.87–7.92(m,1H), 7.92–7.98(m,4H).

Example 68

4-{2-{5-[2-(4,8-Dimethylquinolyl)]pyrrolyl}}benzoic acid

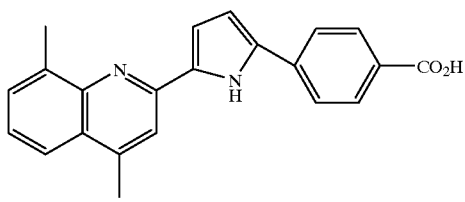

¹H-NMR (DMSO-d₆, 400 MHz) δ; 2.70(s,3H), 2.83(s,3;H), 6.86–6.1)0(m,1H), 7.09–7.13(m,1H), 7.38–7.44(m,1H), 7.56–7.60(m,1H), 7.83–7.87(m,1H), 7.9)0–7.94(m,1H), 7.96(s,4H).

Example 69

4-{2-{5-[2-(5,8-Dimethylquinolyl)]pyrrolyl}}benzoic acid

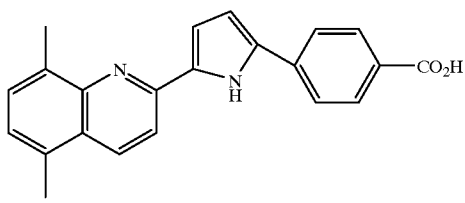

¹H-NMR (DMSO-d₆, 400 MHz) δ; 2.59(s,3H), 2.77(s, 3H), 6.84(m,1H), 7.10(m,1H), 7.20(d,J=6.8 Hz, 1H), 7.44 (d,J=6.8 Hz,1H), 7.94(m,4H), 8.03(d,J=8.8 Hz,1H), 8.37(d, J=8.8 Hz,1H), 11.55(s,1H).

Example 70

4-{2-{5-[2-(8-Methylquinolyl)]pyrrolyl}}benzoic acid

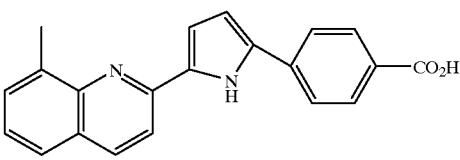

¹H-NMR (DMSO-d₆, 400 MHz) δ; 2.82(s,3H), 6.76(dd, J=2.4,3.6Hz, 1H), 7.08(dd,J=2.0,3.6 Hz,1H), 7.36(t,J=7.6 Hz,1H), 7.55(d,J=7.0 Hz,1H), 7.69(d,J=8.0 Hz,1H), 7.82(d, J=8.4 Hz,2H), 7.91(d,J=8.4 Hz,2H), 8.01(d,J=8.4 Hz,1H), 8.25(d, J=8.4 Hz,1H), 11.45(s,1H).

Example 71

4-{2-{5-[2-(8-Isopropylquinolyl)]pyrrolyl}}benzoic acid

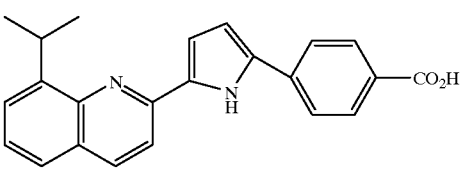

¹H-NMR (DMSO-d₆, 400 MHz) δ; 1.35(d,J=7.2 Hz,6H), 4.52(quint.,J=7.2 Hz,1H), 6.82(m,1H), 7.09(m,1H), 7.43(t, J7.6 Hz,1H), 7.59(d,J=7.2 Hz,1H), 7.69(d,J=8.0 Hz,1H), 7.89(d,J=8.4 Hz,2H), 7.96(m,2H), 8.03(d,J=8.4 Hz,1H), 8.27(d,J=8.4 Hz,1H), 11.55(s,1H).

Example 72

4-{2-{5-[2-(8-Isopropylquinolyl)]-1-isopropylpyrrolyl}}benzoic acid

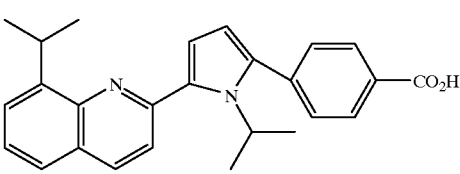

¹H-NMR (DMSO-d₆, 400 MHz) δ; 1.38(d,J=6.8 Hz,6H), 1.48(d,J=7.2 Hz,6H), 4.47(quint.,J=7.0 Hz,1H), 5.54(quint., J=7.0 Hz,1H), 6.25(d,J=4.0 Hz,1H), 6.71(d,J=4.0 Hz,1H), 7.47(t,J=8.0 Hz,1H), 7.63(m,2H), 7.65(d,J=8.0 Hz,2H), 7.73 (d,J=8.4 Hz,1H), 8.11(d,J=8.4 Hz,1H), 8.19(d,J=8.0 Hz,2H).

Example 73

4-{2-{5-[2-(7,8-Dimethylquinolyl)]pyrrolyl≡}benzoic acid

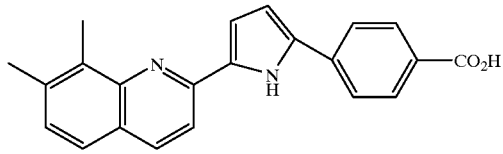

¹H-NMR (DMSO-d₆, 400 MHz) δ; 2.45(s,3H), 2.7(s,3H), 6.86(dd,J=2.4,3.6 Hz,1H), 7.09(dd,J=2.4, 3.6 Hz,1H), 7.32(d,J=8.0 Hz,1H), 7.61(d,J=8.0 Hz,1H), 7.92–7.99(m, 5H), 8.22(d,J=8.8 Hz,1H), 11.60(s,1H), 12.84(br s,1H).

Example 74

4-{2-{5-[2-(5-Isopropyl-8-methylquinolyl)]pyrrolyl}}benzoic acid

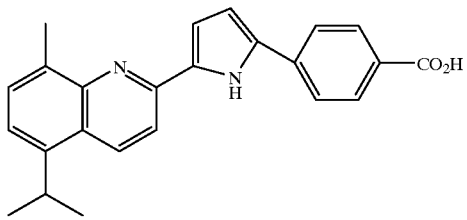

¹H-NMR (DMSO-d₆, 400 MHz) δ; 1.31(d,J=6.8Hz,6H), 2.78(s,3H) 3.69(quint.,J=6.8 Hz,1H), 6.87(m,1H), 7.10(m,1H), 7.28(d,J=8.0 Hz,1H), 7.51(d,J=7.2 Hz,1H), 8.02(d,J=8.8 Hz,1H), 8.52(d,J=8.8 Hz,1H), 11.58(s,1H).

Example 75

4-{2-{5-[2-(6-Isopropylquinolyl)]pyriolyl}}benzoic acid

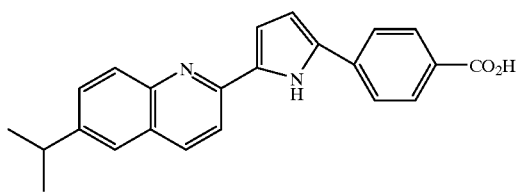

¹H-NMR (DMSO-d₆, 400 MHz) δ; 1.30(d,J=6.8 Hz,6H), 3.09(quint.,J=6.8 Hz,1H), 6.94(m,2H), 7.70–7.80(m,3H), 7.92–8.14(m,6H).

Example 76

4-{2-{5-[2-(7-Isopropylquinolyl)]pyrrolyl}}benzoic acid

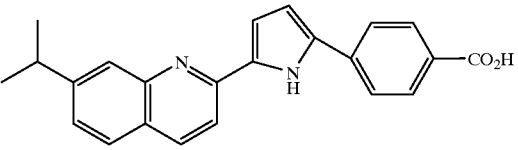

¹H-NMR (DMSO-d₆, 400 MHz) δ; 1.32(d,J=6.8 Hz,6H), 3.23(quint.,J=6.8 Hz,1H), 7.02(m,1H), 7.58(m,1H), 7.92–8.20(m,9H).

Example 77

4-{2-{5-[2-(8-Isopropyl-3-methylquinolyl)]pyrrolyl}}benzoic acid

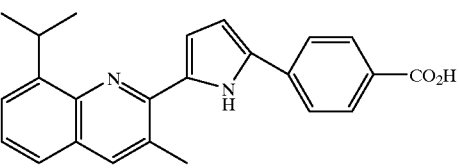

¹H-NMR (DMSO-d₆, 400 MHz) δ; 1.34(d,J=6.8 Hz,6H), 4.52(quint.,J=6.8 Hz,1H), 6.87(m,2H), 7.45(t,J=7.6 Hz,1H), 7.55(d,J=7.2 Hz,1H), 7.66(d,J=7.6 Hz,1H), 7.90(d,J=8.4 Hz,2H), 7.96(d,J=8.4 Hz,2H), 8.14(s,1H), 11.31(s,1H).

Example 78

4-{2-{5-[2-(5,6,7,8-Tetramethylquinolyl)]pyrrolyl}}benzoic acid

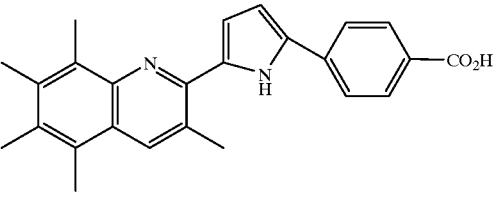

¹H-NMR (DMSO-d₆, 400 MHz) δ; 2.36(s,3H), 2.39(s, 3H), 2.54(s,3H), 2.82(s,3H), 6.86(m,1H), 7.06(m,1H), 7.90–7.98(m,5H), 8.41(d,J=8.8 Hz,1H), 11.58(s,1H).

Example 79

4-{2-{5-[2-(8-Phenylquinolyl)]pyrrolyl}}benzoic acid

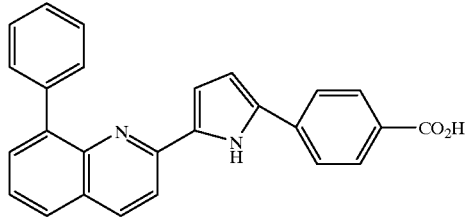

$^{1}$H-NMR (DMSO-$d_6$, 400 MHz) δ; 6.84(m,1H), 6.93(m, 1H), 7.44(t,J=7.2 Hz,1H), 7.52–7.60(m,3H), 7.78(d,J=7.2 Hz,1H), 7.84(m,4H), 7.91(d,J=8.0 Hz,1H), 7.96(d,J=8.4 Hz,2H), 8.15(d,J=8.8 Hz,1H), 8.43(d,J=8.8 Hz,1H).

Example 80

4-{2-{5-[5-(1,2,3-Trimethylindolyl)]pyrrolyl}}benzoic acid

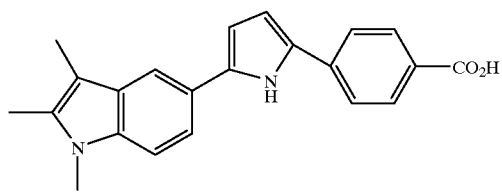

$^{1}$H-NMR (DMSO-$d_6$, 400 MHz) δ; 2.24(s,3H), 2.32(s, 3H), 3.63(s,3H), 6.50–6.56(m,1H), 6.70–6.78(m,1H), 7.32–7.35(m,1H), 7.45–7.49(m,1H), 7.84–7.90(m,5H).

Example 81

4-{2-{5-[5-(1-Isopropyl-2-methylindolyl)]pyrrolyl}}benzoic acid

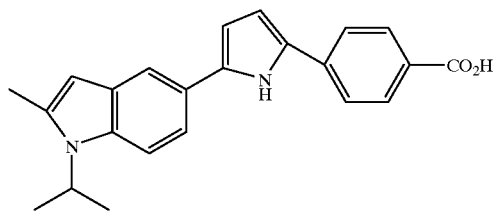

$^{1}$H-NMR (CDCl$_3$, 400 MHz) δ; 1.64(d,J=7.2 Hz,6H), 2.46(s,3H), 4.66(hept.,J=6.8 Hz,1H), 6.24(s, 1H), 6.54–6.56 (m,1H), 6.75–6.77(m,1H), 7.33(dd,J=0.8,8.4 Hz,1H), 7.49 (d,J=8.8 Hz,1H), 7.60(d,J=8.8 Hz,2H), 7.68(d,J=0.8 Hz,1H), 8.11(d,J=8.4 Hz,2H), 8.70(br s,1H).

Example 82

4-{2-{5-[6-(1,2,3,4-Tetrahydro-1-isopropylquinolyl)]pyrrolyl}}benzoic acid

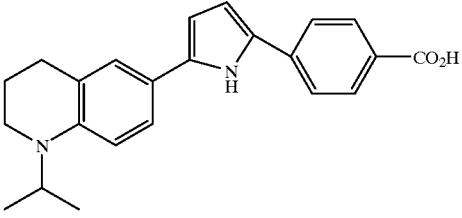

$^{1}$H-NMR (DMSO-$d_6$, 400 MHz) δ; 1.10(d,J=7.4 Hz,6H), 1.82(q,J=7.2 Hz,2H), 2.70(t,J=7.2 Hz,2H), 3.10(t,J=7.2 Hz,2H), 4.04–4.15(m,1H), 6.35(br s,1H), 6.64–6.73(m,2H), 7.32(d,J=2.0 Hz,1H), 7.33(dd,J=2.0,8.2 Hz,1H), 7.80(d,J= 8.4 Hz,2H), 7.83(d,J=8.4 Hz,2H), 11.10(br s,1H).

Example 83

4-{2-{5-[6-(1,4-Dimethyl-1,2,3,4-tetrahydroquinolyl)]pyrrolyl}}benzoic acid

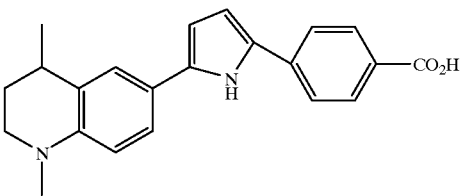

$^{1}$H-NMR (DMSO-$d_6$, 400 MHz) δ; 1.27(d,J=6.8 Hz,3H), 1.60–1.70(m,1H), 1.92–2.02(m,1H), 2.82–2.94 (m,4H), 3.12–3.26(m,2H), 6.39(br s,1H), 6.58(d,J=8.4 Hz,1H), 6.70 (br s,1H), 7.40–7.43(m,2H), 7.80–7.88(m,4H), 11.10(br s,1H), 12.70(br s,1H).

Example 84

4-{2-{5-[6-(1,4,4-Trimethyl-1,2,3,4-tetrahydroquinolyl)]pyrrolyl}}benzoic acid

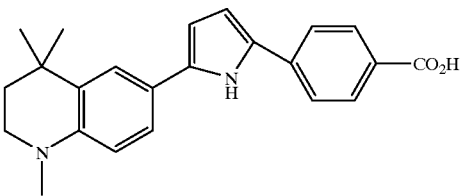

$^{1}$H-NMR (DMSO-$d_6$, 400 MHz) δ; 1.30(s,6H), 1.70–1.78 (m,2H), 2.85(br s,3H), 3.15–3.25(m,2H), 6.40–6.75(m,3H), 7.40–7.60(m,2H), 7.75–8.00(m,4H).

Example 85

4-{2-{5-[7-(1,5,5-Trimethyl-2,3,4,5-tetrahydro-1H-benzazepinyl)]pyrrolyl}}benzoic acid

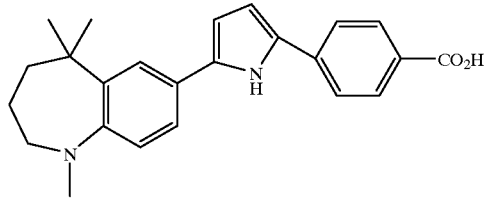

$^1$H-NMR (DMSO-$d_6$, 400 MHz) 67 ; 1.39(s,6H), 1.54–1.62(m,2H), 1.70–1.78(m,2H), 2.80–2.86(m,5H), 6.44–6.50(m,1H), 6.71–6.73(m,1H), 6.94(d,J=8.4 Hz,1H), 7.47–7.51 (m,1H), 7.54–7.56(m,1H), 7.81–7.10(m,4H).

Example 86

4-{2-{5-[6-(1,4-Diisopropyl-1,2,3,4-tetrahydroquinoxalyl)]pyrrolyl}}benzoic acid

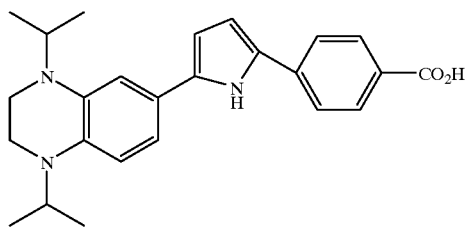

$^1$H-NMR (CDCl$_3$, 400 MHz) δ; 1.21(br s,12H), 3.20(br s,4H), 4.05(br s,2H), 6.60–6.68 (m,3H), 7.40–7.70(m,2H), 8.00–8.20(m,2H), 8.60(br s,2H).

Example 87

4-{2-{5-[7-(4-Isopropyl-3,4-dihydro-2H-1,4-benzooxazinyl)]pyrrolyl}}benzoic acid

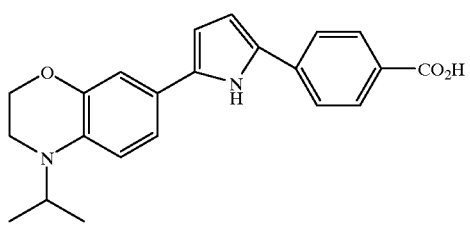

$^1$H-NMR (DMSO-$d_6$, 400 MHz) δ; 1.11(d,J=6.4 Hz,6H), 3.19(br s,2H), 4.10(hept.,J=6.4 Hz,1H), 4.17 (br s,2H), 6.40(br s,1H), 6.69(br s,1H), 6.80(d,J=8.4 Hz,1H), 7.15–7.20(m,2H), 7.80–7.88(m,4H), 11.13(br s,1H), 12.63 (br s,1H).

Example 88

4-(5,6,7,8-Tetrahydro-5,5,8,8-tetramethyl-2-quinoxalinecarbamoyl)benzoic acid

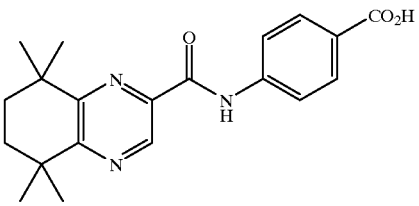

Melting point: 257 to 259° C.; $^1$H-NMR (DMSO-$d_6$, 400 MHz) δ; 1.30(s,6H), 1.40(s,6H), 1.81(s,4H), 7.97(s,4H), 9.05(s,1H), 10.44(s,1H).

Example 89

4-(5,5,7,7-Tetramethyl-2-cyclopenta[b]pyrazinecarbamoyl)benzoic acid

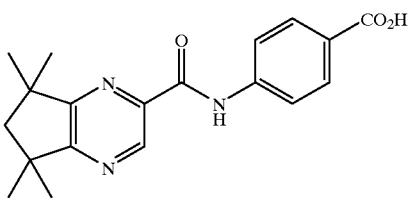

Melting point: 236 to 238° C.; $^1$H-NMR (CDCl$_3$, 400 MHz) δ; 1.41(s,6H), 1.43(s,6H), 2.09(s,3,2H), 7.90(d,J=8.8 Hz,2H), 8.16(d, J=8.8 Hz,2H), 9.30(s,1H), 9.93(s,1H).

Example 90

4-(2,3-Dicyclopentyl-2-pyrazinecarbamoyl)benzoic acid

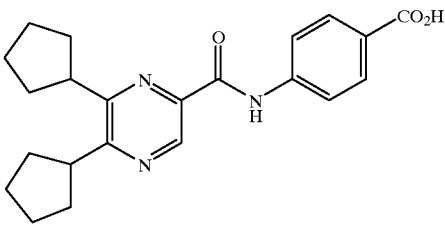

Melting point: 248 to 250° C.; $^1$H-NMR (CDCl$_3$, 400 MHz) δ; 1.70–2.14(m,16H), 3.50–3.60(m,2H), 7.85(d,J=8.8 Hz,2H), 8.15(d,J=8.8 Hz,2H), 9.22(s,1H), 9.93(s,1H).

Example 91

4-(5,6-Diisopropyl-3-[1,2,4]triazinezarbamoyl)benzoic acid

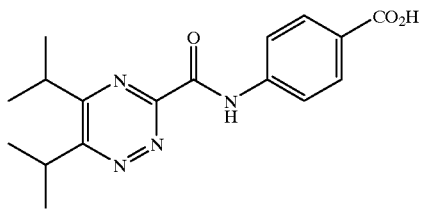

Melting point: 182 to 184° C.; $^1$H-NMR (DMSO-$d_6$, 400 MHz) δ; 1.28(d,J=6.8 Hz,6H), 1.37(d,J=6.8 Hz,6H), 3.44 (quint.,J=6.8 Hz,1H), 3.56(quint.,J=6.8 Hz,1H), 7.95(d,J= 8.6 Hz,2H), 7.98(d,J=8.6 Hz,2H), 11.15(s,1H), 12.80(br s,1H).

Example 92

4-(3-Chloro-2-isopropyloxy-5-pyridinecarbamoyl)benzoic acid

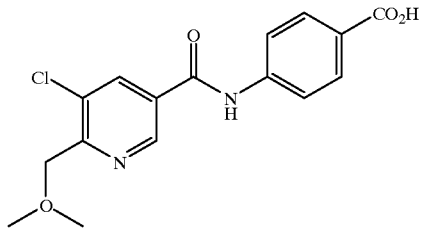

Melting point: 251 to 253° C.; $^1$H-NMR (DMSO-$d_6$, 400 MHz) δ; 1.35(d,J=6.2 Hz,6H), 5.38(hept.,J=6.2 Hz,1H), 7.86(d,J=8.8 Hz,2H), 7.93(d,J=8.8 Hz,2H), 8.39(br s,1H), 8.70(brs,1H), 10.53(br s,1H).

Referential Example 1

5,6,7,8-Tetrahydro-5,5,8,8-tetramethylquinoxaline-2-carbaldehyde

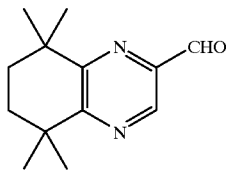

Step 1

5,6,7,8-Tetrahydro-5,5,8,8-tetramethylquinoxaline-2-methanol

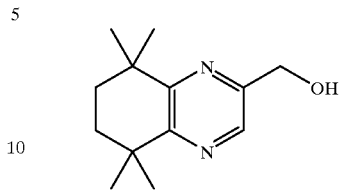

Methanol (500 ml) was added to 14.0 g of 3,3,6,6-tetramethyl-1,2-cyclohexanedione, 15.4 g of DL-2,3-diaminopropionic acid hydrobromide and 13.3 g of sodium hydroxide, followed by heating under reflux for 2 days. After the reaction mixture was allowed to cool down, 15 ml of concentrated sulfuric acid were added. The resulting mixture was heated under reflux for 8 hours. After being allowed to cool down, the reaction mixture was concentrated under reduced pressure. A saturated aqueous solution of sodium bicarbonate was poured into the residue to neutralize it, followed by extraction with ethyl acetate. The organic layer was successively washed with water and saturated saline, dried offer anhydrous magnesium sulfate and concentrated under reduced pressure. The residue so obtained was subjected to chromatography on a silica gel column (developing solvent: 10% ethyl acetate/n-hexane), whereby 15.0 g of a colorless oil were obtained.

The resulting oil was dissolved in 250 ml of tetrahydrofuran, followed by the dropwise addition of a 1M hexane solution of diisobutyl aluminum hydride at −78° C. under a nitrogen gas stream. After the reaction mixture was raised to room temperature and stirred for one hour, it was cooled to −78° C. A saturated aqueous solution of ammonium chloride was added to terminate the reaction. After raised to room temperature, the reaction mixture was added with water under stirring and the precipitate so formed was filtered. The filtrate was; washed with saturated saline, dried over anhydrous magnesium sulfate and concentrated under reduced pressure. The residue so obtained was subjected to chromatography on a silica gel column (developing solvent: 20% ethyl acetate/n-hexane), whereby 7.7 g of the title compound were obtained in the form of a colorless oil.

$^1$H-NMR (CDCl$_3$, 400 MHz) δ; 1.32(s,6H), 1.33(s,6H), 1.80(s,4H), 3.62(t,J=5.1 Hz,1H), 4.74(d, J=5.1 Hz,2H), 8.31 (s,1H).

Step 2

5,6,7,8-Tetrahydro-5,5,8,8-tetramethylquinoxaline-2-carbaldehyde

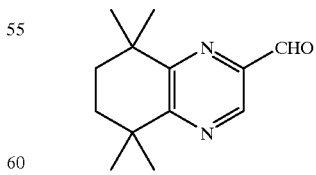

To a solution of 4.58 ml of oxalyl chloride in 250 ml of dichloromethane, a solution of 7.45 ml of dimethyl sulfoxide in 17 ml of dichleoromethane was added dropwise at −60° C. under a nitrogen as stream, followed by stirring for 5 minutes.

A solution of 7.7 9 of 5,6,7,8- tetrahydro-5,5,8,8-tetramethylquinoxaline -2-methanol in 120 ml of dichioromethane was then added dropwise to the reaction mixture and the resulting mixture was stirred for 15 minutes. To the reaction mixture were added with 35.1 ml of triethylamine, followed by stirring for 5 minutes. After the reaction mixture was raised to room temperature and stirred for 15 minutes, water was added and the resulting mixture was extracted with dichloromethane. The organic layer was successively washed with water and saturated saline, dried over anhydrous magnesium sulfate and concentrated under reduced pressure. The residue so obtained was subjected to chromatography on a silica gel column (developing solvent: 10% ethyl acetate/n-hexane), whereby 6.7 g of the title compound were obtained as a pale yellow solid.

$^1$H-NMR (CDCl$_3$, 400 MHz) δ; 1.35(s,6H), 1.37(s,6H), 1.83(s,4H), 8.91(s,1H), 10.1(s,1H).

Referential Example 2

5,6,7,8-Tetrahydro-3,5,5,8,8-pentamethylquinoxaline-2-carbaldehyde

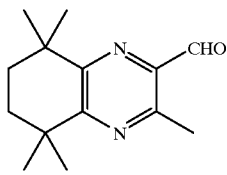

Step 1

5,6,7,8-Tetrahydro-2,3,5,5,8,8-hexamethylquinoxaline

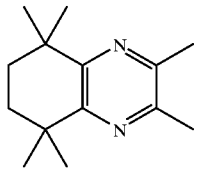

Under a nitrogen stream, 19.6 g of lithium aluminum hydride were suspended in 300 ml of tetrahydrofuran. To the resulting suspension, a solution of 15 g of dimethylglyoxime in 300 mL of tetrahydrofuran was added dropwise while heating under reflux. After heating under reflux for 5 hours, the reaction mixture was cooled to 0° C. and 19.6 ml of water, 19.65 ml of a 15% aqueous solution of sodium hydroxide and 39.2 ml of water were added dropwise successively. The precipitate so formed was filtered through Celite. The filtrate was concentrated, whereby 4.7 g of a colorless oil were obtained. The resulting oil was dissolved in 30 ml of acetic acid. To the resulting solution was added 2,2,5,5-tetramethyl-1,2-hexanedione, followed by heating under reflux for 2 hours. The reaction mixture was then poured into a saturated aqueous solution of sodium bicarbonate, followed by extraction with ethyl acetate. The organic layer was successively washed with water and saturated-saline, dried over anhydrous magnesium sulfate and concentrated under reduced pressure. The residue so obtained was subjected to chromatography on a silica gel column (developing solvent: 2% ethyl acetate/n-hexane), whereby 2.7 g of the title compound were obtained in the form of a colorless solid.

$^1$H-NMR (CDCl$_3$, 400 MHz) δ; 1.28(s,12H), 1.74(s,4H), 2.44(s,6H).

Step 2

5,6,7,8-Tetrahydro-3,5,5,8,8-pentamethylquinoxaline-2-methanol

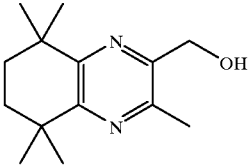

In 10 ml of carbon tetrachloridp were dissolved 570 rmg of 5,6,7,8-tetrahydro-2,3,5,5,8,8hexamethylquinoxaline. To the resulting solution were added 511 mg of N-bromosuccimide and a small amount of azobisisobutylonitrile, followed by heating under reflux for 2 hours. After the reaction mixture was cooled down, 10 ml of hexane were added. The precipitate so formed was filtered and the filtrate was concentrated under reduced pressure, whereby a colorless oils was obtained. The resulting oil was dissolved in 10 ml of 1,4-dioxane. To the resulting solution were added 10 ml of water and 553 mg of sodium carbonate, followed by heating under reflux for 3 hours. The reaction mixture was extracted with ethyl acetate. The organic layer was4 successively washed with water and saturated saline, dried over anhydrous magnesium sulfate and concentrated under reduced pressure. The residue so obtained was subjected to chromatography on a silica gel column (developing solvent: 5% ethyl acetate/-hexane), whereby 436 mg of the title compound were obtained in the form of a yellow solid.

$^1$H-NMR (CDCl$_3$, 400 MHz) δ; 1.30(s,6H), 1.31(s,6H), 1.78(s,4H), 2.38(s,3H).

Step 3

5,6,7,8-Tetrahydro-3,5,5,8,8-pentamethylquinoxaline-2-carbaldehyde

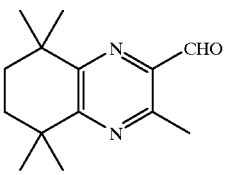

A solution of 923 μl of dimethyisulfoxide in 2 ml of dichloromethane was added dropwise to a solution of 797 pl of oxalyl chloride in 6 ml of dichloromethane at −60° C. under a nitrogen gas stream, followed by stirring for 5 minutes. To the reaction mixture, a solution of 1 g of 5,6,7,8-tetrahydro-3,5,5,8,8-pentamethylquinoxaline-2-methanol in 6 ml of dichloromethane was added dropwise and the resulting mixture was stirred for 15 minutes. Triethylamine (4.8 ml) was then added dropwise to the reaction mixture, followed by stirring for 5 minutes. After the reaction mixture was raised to room temperature and stirred for 15 minutes, water was added thereto. The resulting mixture was extracted with dichloromethane. The organic layer was successively washed with water and saturated saline, dried over anhydrous magnesium sulfate and concentrated under reduced pressure. The residue so obtained was subjected to chromatography on a silica gel column (developing solvent:

10% ethyl acetate/n-hexane), whereby 940 mg of the title compound were obtained in the form of a pale yellow solid.

¹H-NMR (CDCl₃, 400 MHz) δ; 1.32(s,6H), 1.33(s,6H), 1.82(s,4H), 2.78(s,3H), 10.13(s,1H).

Referential Example 3

5,8-Dimethyl-5,1,7,8-tetrahydroquinoline-2-carbaldehyde

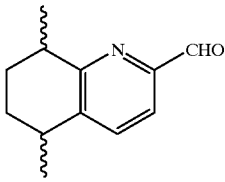

Phosphorus oxychloride (18.6 g, 0.12 mol) was added dropwise to 29.2 g (0.4 mol) of N,N-dimethylformamide under ice cooling. After stirring at room temperature for 30 minutes, the reaction mixture was cooled over ice bath, followed by the dropwise addition of 17.0 g (0.1 mol) of 5,8-dimethyl-5,6,7,8-tetrahydroquinoline. After stirring at room temperature for one hour, the reaction mixture was poured into ice water and neutralized with an aqueous solution of sodium bicarbonate, followed by extraction with ethyl acetate. The organic layer was dried over anhydrous magnesium sulfate and concentrated under reduced pressure. The residue so obtained was subjected to chromatography on a silica gel column (developing solvent: 10% ethyl acetate/n-hexane), whereby 11.4 g of the title compound were obtained in the form of a reddish brown oil.

¹H-NMR (CDCl₃, 400 MHz) δ; 1.31, 1.33(2×d,J=7.1 Hz,total 3H), 1.40, 1.44(2×d,J=7.1 Hz,total 3H), 1.45–1.79 (m,2H), 1.86–2.20(m,2H), 2.94–3.12(m,2H), 7.64(d,J=7.9 Hz,1H), 7.73(d,J=7.9 Hz,1H), 10.01(s,1H).

Referential Example 4

8-Isopropyl-4-methylquinoline-2-carbaldehyde

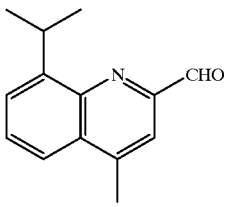

Step 1

Methyl 8-isopropylquinolone-2-carboxylate

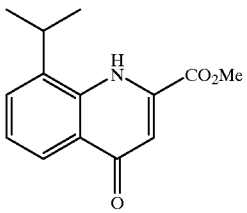

In 200 ml of methanol were dissolved 10 g of 2-isopropylaniline and 3.1 ml of Triton B. Under stirring, 9.1 ml of dimethylacetylene dicarboxylate were added dropwise to the resulting solution, followed by stirring for 24 hours. Methanol was distilled off under reduced pressure and the residue was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/in-hexane), whereby 2.6 g of a brown oil were obtained. The resulting oil was dissolved in 20 ml of diphenyl ether and the resulting solution was stirred at 250° C. for 2 hours. After cooling, the reaction mixture was subjected to chromatography on a silica gel column (developing solvent: 50% ethyl acetate/n-hexane), whereby 1 g of the title compound was obtained in the form of a pale brown solid.

¹H-NMR (CDCl₃, 400 MHz) δ; 1.42(d,J=6.8 Hz,6H), 3.28(hept.,J=6.8 Hz,1H), 4.06(s,3H), 6.97(d,J=1.6 Hz,1H), 7.36(t,J=8.0 Hz,1H), 7.59(dd,J=1.2,7.6 Hz,1H), 8.23(dd., J=0.8,8.4 Hz,1H), 9.10(br s,1H).

Step 2

Methyl 4-trifluromethanesulfonyloxy-8-isopropylquinoline-2-carboxylate

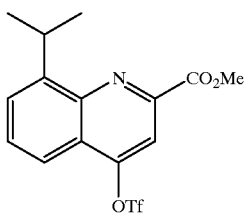

In 100 ml of dichloromethane were dissolved 4.2 g of methyl 8-isopropylquinolone-2-carboxylate, 3 ml of 2,6-lutidine and 209 mg of 4-dimethylaminopyridine under a nitrogen gas stream. Trifluoromethanesulfonic anhydride (3.2 ml) was added dropwise to the resulting solution at 0° C., followed by stirring at room temperature for 24 hours. A saturated aqueous solution of ammonium chloride was added to the reaction mixture and the resulting mixture was extracted with dichloromethane. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/in-hexane), whereby 6.3 g of the title compound were obtained in the form of a colorless solid.

¹NMR (CDCl₃, 400 MHz) δ; 1.40(d,J=6.8Hz,6H), 4.08 (s,3H), 4.43(hept.,J=6.8 Hz,1H), 7.77(t,J=8.0 Hz,1H), 7.80 (dd,J=2.0,7.6 Hz,1H), 7.95(dd,J=2.0,8.0 Hz,1H), 8.12(s, 1H).

Step 3

Methyl 8-isopropyl-4-methylquinoline-2-carboxylate

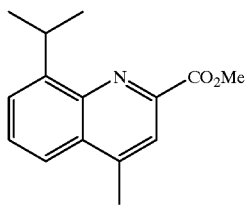

In 30 ml of tetrahydrofuran were suspended 1.8 g of zinc chloride at room temperature unclear a nitrogen gas stream. A 1.4M tetrahydrofuran solution of methyl lithium (9.5 ml) was added dropwise to the resulting suspension and the resulting mixture was stirred for one hour. The reaction mixture was added dropwise to a solution of 1 g of methyl 4-trifluoromethanesulfonyloxy-8-isopropylquinoline-2-carboxylate and 153 mg of tetrakis(triphenylphosphine)palladium in 20 ml of tetrahydrofuran, followed by stirring at room temperature for 65 hours. Dilute hydrochloric acid was added to the reaction mixture and the resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 2% ethyl acetate/n-hexane), whereby 125 mg of the title compound were obtained in the form of a colorless solid.

Step 4

8-Isopropyl-4-methylquinoline-2-carbaldehyde

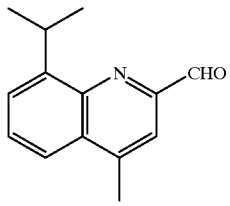

Methyl 8-isopropyl-4-methyl-2-quinolinecarboxylate was dissolved in 10 ml of tetrahydrofuran, followed by the dropwise addition of a 1M hexane solution of diisobutyl aluminum hydride at 0° C. under a nitrogen gas atmosphere. After stirring for 2 hours, saturated aqueous ammonium chloride was added to terminate the reaction. Water was added to the reaction mixture and the precipitate so formed was filtered. The filtrate was concentrated under reduced pressure, whereby 107 mg of 8-isopropyl-4-methylquinoline-2-methanol were obtained in the form of a colorless oil. Under a nitrogen gas stream, a solution of 210 μl of dimethyl sulfoxide in 0.5 ml of dichloromethane was added dropwise to a solution of 172 μl of oxalyl chloride in 1 ml of dichloromethane at −60° C. under a nitrogen gas stream, followed by stirring for 5 minutes. To the reaction mixture, a solution of 107 mg of 8-isopropyl-4-methyl-2-quinolinemethanol in 2 ml of dichloromethane was added dropwise, followed by stirring for 15 minutes, dropwise addition of 1 ml of triethylamine and stirring for 5 minutes. The reaction mixture was raised to room temperature and stirred for one hour. Water was added to the reaction mixture and the resulting solution was extracted with dichloromethane. The organic layer was successively washed with water and saturated saline, dried over anhydrous magnesium sulfate and concentrated under reduced pressure. The residue so obtained was subjected to chromatography on a silica gel column (developing solvent:: 3% ethyl acetate/n-hexane), whereby 87 mg of the title compound were obtained in the form of a pale yellow solid.

$^1$H-NMR (CDCl$_3$, 400 MHz) δ; 1.35(d,J=7.0 Hz,6H), 2.70(,J=1.0 Hz,3H), 4.44(hept.,J=7.0 Hz,3H), 7.59(t,J=1.2 Hz,1H), 7.63(dd,J=1.6,7.2 Hz,1H), 7.79(d,J=1.2 Hz,1H), 7.83(dd,J=2.0,8.0 Hz,1H), 10.13(s,1H).

Referential Example 5

8-Isopropyl-4-methoxyquinoline-2-carbaldehyde

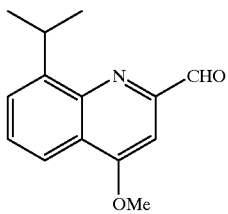

Step 1

Methyl 8-isopropyl-4-methoxyquinoline-2-carboxylate

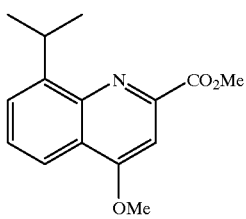

In 10 ml of N,N-dimethylformamide were dissolved 700 mg of methyl 8-isopropylquinoline-2-carboxylate. To the resulting solution were added 1.2 g of potassium carbonate and 195 μl of methyl iodide, followed by stirring at 50° C. for one hour. The reaction mixture was extracted with ethyl acetate. The organic layer was successively washed with water and saturated saline, dried over anhydrous magnesium sulfate and concentrated under reduced pressure. The residue so obtained was subjected to chromatography on a silica gelcoluimn (developing solvent: 5% ethyl acetate/n-hexane), whereby 710 mg of the title compound were obtained in the form of a pale yellow solid.

$^1$H-NMR (CDCl$_3$, 400 MHz) δ; 1.37(d,J=6.8 Hz,6H), 4.05(s,3H), 4.10(s,3H), 4.42(hept.,J:=6.8 Hz, 1H), 7.55(s, 1H), 7.56(t,J=7.6 Hz,1H), 7.65(dd,J=1.2,7.2 Hz,1H), 8.07 (dd,J=1.15,8.0 Hz,1H).

Step 2

8-Isopropyl-4-methyoxyolquinoline-2-carbaldehyde

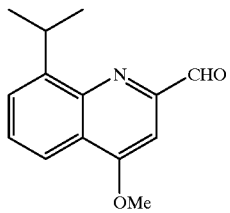

In a similar manner to Step 4 of Referential Example 4, 597 mg of the title compound were obtained in the form of a pale yellow solid.

$^1$H-NMR (CDCl$_3$, 400 MHz) δ; 1.40(d,J=7.0 Hz,6H), 4.10(s,3H), 4.45(hept., J=7.0 Hz,1H), 7.37(s, 1H), 7.59(dd, J=7.2,8.0 Hz,1H), 7.68(dd,J=1.2,7.2 Hz,1H), 8.10(dd, J=1.2, 8.0 Hz,1H), 10.15(s,1H).

Referential Example 6

4-Chloro-8-isopropylquinoline-2-carbaldehyde

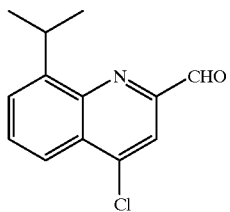

Step 1

Methyl 4-chloro-8-isopropylquinoline-2-carboxylate

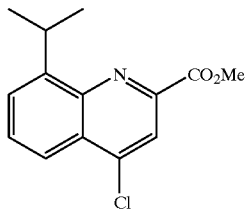

In 6 ml of phosphorus oxychloride were dissolved 700 mg of methyl 8-isopropylquinolone-2-carboxylate and 100 mg of phosphorus pentachloride. The resulting solution was stirred at 80° C. for 15 hours. The reaction mixture was poured into a saturated aqueous solution of sodium bicarbonate and the resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 10% ethyl acetate/n-hexane), whereby 680 mg of the title compound were obtained as a pale brown solid.

$^1$H-NMR (CDCl$_3$, 400MHz) δ; 1.39(d,J=6.8 Hz,6H), 4.06 (s,3H), 4.44(hept., J=6.8 Hz,1H), 7.70(t,J=7.2 Hz,1H), 7.73 (dd,J=2.4, 7.2 Hz,1H), 8.13(dd,J=1.6,8.0 Hz,1H), 8.24(s, 1H).

Step 2

4-Chloro-8-isopropylquinioline -2-carbaldehyde

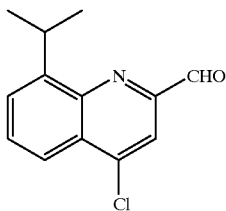

In a similar manner to Step 4 of Referential Example 4, 456 mg of. the title compound were obtained in the form of a pale yellow solid.

$^1$H-NMR (CDCl$_3$, 400 MHz) δ; 1.34(d,J=7.0 Hz,6H), 4.40(hept.,J=7.0 Hz,1H), 7.67(t,J=7.2 Hz,1H), 7.70(dd,J= 2.0,7.2 Hz,1H), 8.01(s,1H), 8.09(dd,J=2.4,6.8 Hz,1H), 10.11 (s,1H).

Referential Example 7

5,8-Dimethylquinoline-2-carbaldehyde

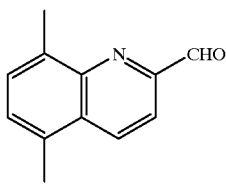

In 50 ml of 6N hydrochloric acid, 10.0 g of 2,5-dimethylaniline were dissolved. To the resulting solution, 6.8 ml of crotonaldehyde were added dropwise under reflux. After the completion of the dropwise addition, the reaction mixture was heated under reflux for further one hour and the reaction was terminated. After the reaction mixture was allowed to cool down to room temperature, 5N sodium hydroxide was added to neutralize the reaction mixture, followed by extraction with ethyl acetate (200 ml×2). The combined organic layers were washed with saturated saline and dried over anhydrous magnesium sulfate. After filtration, the filtrate was concentrated and the product so obtained was purified by chromatography on a silica gel column, whereby 5.8 g of 2,5,8-trimethylquinoline were obtained. In 30 ml of ethanol were dissolved 3.6 g of 2,5,8-trimethylquinoline and 2.8 g of selenium dioxide, followed by heating under reflux for 6 hours. The residue obtained by distilling off ethanol was subjected to chromatography on a silica gel column, whereby 2.3 g of the product were obtained. Since the product was proved to be a mixture of the raw material, aldehyde and a diethylacetal derivative of the aldehyde from the result of $^1$H-NMR, it was treated with 6N-hydrochloric acid (10 ml)-THF (20 ml) and then, extracted with ethyl acetate (100 ml×2). The combined organic layers were washed with a saturated aqueous solution of sodium bicarbonate and dried over anhydrous magnesium sulfate, followed by filtration. The filtrate so obtained was concentrated and the residue was purified by chromatography on a silica gel column, whereby 1.9 g of the title compound were obtained.

$^1$H-NMR (CDCl$_3$, 400 MHz) δ; 2.68(s,3H), 2.85(s,3H), 7.39(d,J=7.2 Hz,1H), 7.54(d,J=7.2 Hz,1H), 8.04(d,J=8.8 Hz,1H), 8.44(d,J=8.8 Hz,1H), 10.23(s,1H).

Referential Example 8

1-Isopropyl-1,2,3,4-tetrahydroquinoline-6-carbaldehyde

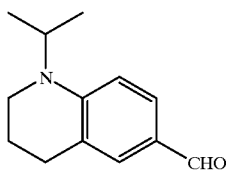

Step 1

1-Isopropyl-1,2,3,4-tetrahydroquinoline

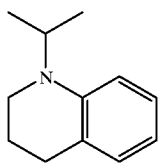

In 60 ml of N,N-dimethylformamide were dissolved 13.8 g of 1,2,3,4-tetrahydroquinoline. To the resulting solution were added 21.1 g of isopropyl iodide and 20.6 g of potassium carbonate, followed by stirring under heat at 60° C. for 5 hours. Water was added to the reaction mixture and the resulting mixture was extracted with ethyl acetate. The organic layer was washed with saturated saline, dried over anhydrous magnesium sulfate and concentrated under reduced pressure. The residue so obtained was subjected to chromatography on a silica gel column (developing solvent: 3% ethyl acetate/n-hexane), whereby 13.1 g of the title compound were obtained in the form of a colorless oil.

$^1$H-NMR (CDCl$_3$, 400 MHz) δ; 1.20(d,J=6.8 Hz,6H), 1.92(tt,J=6.0,6.0 Hz,2H), 2.76(t,J=6.0 Hz,2H),3.18(t,J=6.0 Hz,2H), 4.13(hept.,J=6.8 Hz,1H), 6.57(,dt,J=0.8,7.2 Hz,1H), 6.71(d,J=8.4 Hz,1H), 6.97(dd,J=1.2,7.6 Hz,1H), 7.05–7.10 (m,1H).

Step 2

1-Isopropyl-1,2,3,4-tetrahydroquinoline-2-carbaldehyde

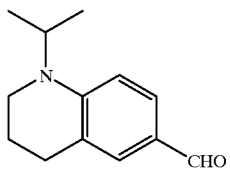

Phosphorus oxychloride (18.6 g) was added dropwise to 29.2 g of N,N-dimethylformamide under ice cooling. The resulting mixture was stirred at room temperature for 30 minutes, followed by the dropwise addition of 17.5 g of 1-isopropyl-1,2,3,4-tetrahydroquinoline slowly under ice cooling. After stirring at room temperature for one hour, the reaction mixture was poured into ice water, neutralized with a saturated aqueous solution of sodium bicarbonate and extracted with ethyl acetate. The organic layer was dried over anhydrous magnesium sulfate and concentrated under reduced pressure. The residue so obtained was subjected to chromatography on a silica gel column (developing solvent: 10% ethyl acetate/n-hexane), whereby 11.4 g of the title compound were obtained as a reddish brown oil.

$^1$H-NMR (CDCl$_3$, 400 MHz) δ; 1.23(d,J=6.5 Hz,6H), 1.90(tt,J=6.0,6.0 Hz,2H), 2.75(t,J=6.0 Hz,2H),3.27(t,J=6.0 Hz,2H), 4.20(hept.,J=6.5 Hz,1H), 6.69(d,J=9.0 Hz,1H), 7.45 (d,J=2.0 Hz,1H), 7.55(dd,J=2.0,9.0 Hz,1H), 9.64(s,1H).

Referential Example 9

1-Isopropylindole-4-carbaldehyde

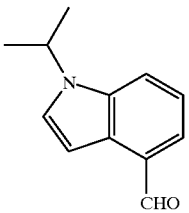

Step 1

Isopropyl 1-isopropylindole-4-carboxylate

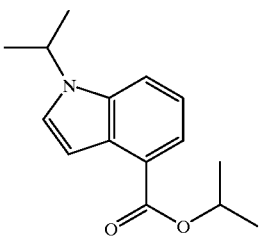

In 50 ml of N,N-dimethylformarnide were dissolved 2.5 g of indole-4-carboxylic acid, followed by the addition of 6.3 g of 2-iodopropane. Under ice cooling, sodium hydride (60% oily) was added in portions and the resulting mixture was stirred at root temperature for 10 hours. Ice was added to the reaction mixture and the resulting mixture was extracted with ethyl acetate. The organic layer was dried over anhydrous magnesium sulfate and concentrated under reduced pressure. The residue was subjected to chromatography on a silica gel column, whereby 2.6 g of the title compound wove obtained in the form of a yellow oil.

$^1$H-NMR (CDCl$_3$, 400 MHz) δ; 1.43(d,J=6.4 Hz,6H), 1.54(d,J=6.4 Hz,6H), 4.72(hept.,J-=6.8 Hz,1H), 5.34(hept., J=6.0 Hz,1H), 7.16(dd,J=0.8,3.6Hz,1H), 7.24(t,J=8.0 Hz,1H), 7.57(dd,J=0.8,8.4 Hz,1H), 7.90(dd,J=1.2,7.6 Hz,1H).

Step 2

1-Isopropylindole-4-carbaldehyde

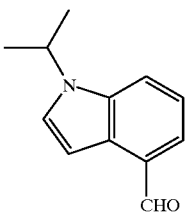

Isopropyl 1-isopropylindole-4-carboxylate (2.6 g) was reduced by diisobutyl aluminum hydride, followed by oxidation with manganese dioxide, whereby the title compound was obtained.

$^1$H-NMR (CDCl$_3$, 400 MHz) δ; 1.56(d,J=6.8 Hz,6H), 4.75(hept.,J=6.8 Hz,1H), 7.26–7.36(m,2H), 7.44 (d,J=3.2 Hz,1H), 7.62–7.67(m,2H), 10.25(s,1H).

Referential Example 10

1,2,3-Trimethyl-indole-5-carbaldehyde

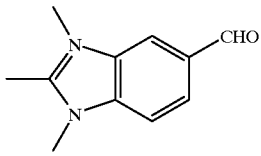

1,2,3-Trimethyl-indole was treated in a similar manner to Referential Example 3, whereby the title compound was synthesized.

$^1$H-NMR (CDCl$_3$, 400 MHz) δ; 2.29(s,3H), 2.37(s,3H), 3.69(s,3H), 7.30(d,J=8.4 Hz,1H), 7.71(dd,J=:0.8,8.4 Hz,1H), 8.03(d,J=0.8 Hz,1H), 10.02(s,1H).

Referential Example 11

5-Isopropyl-1-tertiary-butylpyrazole-3-carbaldehyde

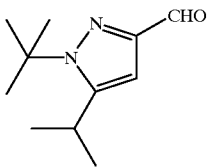

5-Isopropyl-1-tertiary-butylpyrazole was treated in a similar manner to Referential Example 3, whereby the title compound was synthesized.

$^1$H-NMR (CDCl$_3$, 400 MHz) δ; 1.28(d,J=6.0 Hz,6H), 1.68(s,9H), 3.32–3.40(m,1H), 6.66(s,1H), 9.88(s,1H).

Referential Example 12

5,6-Diisopropylpyrazine-2-carboxylic acid

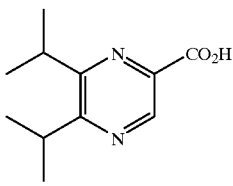

Methanol (30 ml) was added to 600 mg of 2,5-dimethyl-3,4-hexanedione, 593 mg of DL-2,3-diaminopropionic acid hydrochloride and 675 mg of sodium hydroxide. The resulting mixture was heated under reflux for 10 hours, followed by stirring at room temperature overnight. To the reaction mixture were added 2 ml of concentrated sulfuric acid and the resulting mixture was heated under reflux for 8 hours. After being allowed to cool down, the reaction mixture was concentrated under reduced pressure. The residue was poured into a saturated aqueous solution of sodium bicarbonate for neutralization, followed by extraction with ethyl acetate. The organic layer was successively washed with water and saturated saline, dried over anhydrous magnesium sulfate and concentrated under reduced pressure. The residue so obtained was subjected to chromatography on a silica gel column (developing solvent: 10% ethyl acetate/n-hexane), whereby 100 mg of a colorless oil were obtained.

The resulting oil was dissolved in 10 ml of ethanol. To the resulting solution were added 2 ml o:f 5N sodium hydroxide, followed by stirring for 3 hours. Water was added to the reaction mixture and the resulting mixture was made weakly acidic by adjusting its pH with an aqueous solution of hydrochloric acid. The crystals so precipitated were collected by filtration. After washing with water, they were dried under reduced pressure, whereby 80 mg of the title compound were obtained in the form of a colorless solid.

Melting point: 128 to 130° C.;

$^1$H-NMR (CDCl$_3$, 400 MHz) δ; 1.32(d,J=6.8 Hz,6H), 1.33(d,J=6.8 Hz,6H), 3.44(hept.,J=6.8 Hz,1H), 3.46(hept., J=6.8 Hz,1H), 9.19(s,1H).

Referential Example 13

5-Chloro-3-isopropoxy-3-pyridinecarboxylic acid

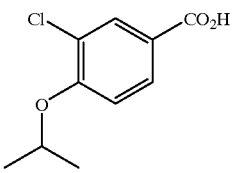

Step 1

Isopropyl 5-chloro-3-isopropoxy-3-pyridinecarboxylate

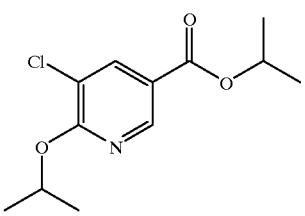

In 20 ml of N,N-diimethylformamide were dissolved 1.0 g of 5-chloro-6-hydroxynicotinic acid. To the resulting solution were added 4.78 g of potassium carbonate and 1.26 ml of 2-iodopropane, followed by stirring under heat at 8° C. for 4 hours. Ice water was added to the reaction mixture and the resulting mixture was extracted with ethyl acetate. The organic layer was successively washed with water and saturated saline, dried over anhydrous magnesium sulfate and concentrated under reduced pressure. The residue so obtained was subjected to chromatography on a silica gel column (developing solvent: 5% ethyl acetate/n-hexane), whereby 600 mg of the title compound were obtained.

$^1$H-NMR (CDCl$_3$, 400 MHz) δ; 1.35(d,J=6.0 Hz,6H), 1.40(d,J=6.0 Hz,6H), 5.23(hept.,J=6.0 Hz,1H), 5.43(hept., J=6.0 Hz,1H), 8.17(d,J=2.4 Hz,1H), 8.67(d,J=:2.0 Hz,1H).

Step 2

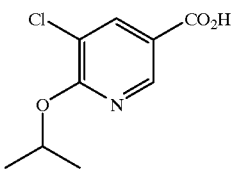

Isopropyl 5-chloro-3-isopropoxy-3-pyridinecarboxylate (300 mg) was hydrolyzed in a similar manner to Referential Example 12, whereby 195 mg of the title compound were obtained in the form of a colorless solid.

$^1$H-NMR (CDCl$_3$, 400 MHz) δ; 1.42(d,J=6.2 Hz,6H), 5.46(hept.,J=6.2 Hz,1H), 8.23(d,J=2.0 Hz, 1H), 8.75(d,J=2.2 Hz,1H).

Referential Example 14

Ethyl 5,6-diisopropyl-3-[1,2,4]triazinecarboxylate

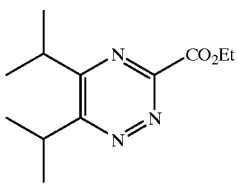

A suspension of 2.5 g of 2,5-dimethyl-3,4-hexanedione and 2.3 g of ethyl 2-amino-2-hydrozonoacetate in 10 ml of acetic acid was heated and stirred at 100° C. for 2 hours under a nitrogen gas stream. The reaction mixture was allowed to cool down and then a saturated aqueous solution of sodium bicarbonate was poured thereto for neutralization, followed by extraction with ethyl acetate. The organic layer was successively washed with saturated saline, dried over anhydrous magnesium sulfate and concentrated under reduced pressure. The residue so obtained was subjected to chromatography on a silica gel column (developing solvent: 10% ethyl acetate/n-hexane), whereby 2.3 g of the title compound were obtained in the form of a yellow oil.

$^1$H-NMR (CDCl$_3$, 400 MHz) δ; 1.34(d,J=6.8 Hz,6H), 1.43(d,J=6.8 Hz,6H), 1.46(t,J=7.2 Hz,3H), 3.34(hept.,J=6.8 Hz,1H), 3.46(hept.,J=6.8 Hz,1H), 4.53(d,J=7.2 Hz,2H).

Referential Example 15

Methyl 4-acryloyl-benzoate

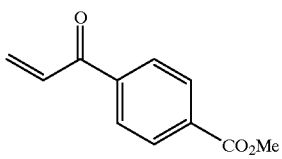

In 150 ml of tetrahydrofuran were dissolved 13.6 g of methyl ester of terephthalaldehyclic acid. To the resulting solution, 100 ml of a 1.0M tetrahydrofuran solution of vinyl magnesium bromide were added dropwise at −78° C., followed by stirring at that temperature for 30 minutes. After quenching with a saturated aqueous solution of ammonium chloride, the reaction mixture was extracted with ethyl acetate (200 ml×2). The combined organic layers were washed with saturated saline, dried over anhydrous magnesium sulfate and then filtered. The filtrate was concentrated and the residue was subjected to chromatography on a silica gel column, whereby 11.6 g of an allyl alcohol derivative were obtained.

The resulting alkyl alcohol derivative (11.6 g) was dissolved n 600 ml of dichloromethane. To the resulting solution were added 3 g of molecular sieve (3A) and 27 g of pyridinium bichromate, followed by stirring at room temperature for 4 hours. The reaction mixture was filtered through Celite. The filtrate was concentrated and the residue was subjected to chromatography on a silica gel column, whereby 5.5 g of the title compound were obtained in the form of a colorless solid.

In a similar manner to the above process, the compounds which will be described below were obtained.

$^1$H-NMR (CDCl$_3$, 400 MHz) δ; 3.96(s,3H), 6.00(d,J=10.4 Hz,1H), 6.46(d,J=17.2 Hz,1H), 7.14(dd,J=10.4,17.2 Hz,1H), 7.98(d,J=8.4 Hz,2H), 8.14(d,J=8.4 Hz,2H).

Referential Example 16

5,6-Diisopropylpyrazine-2-carbaldehyde

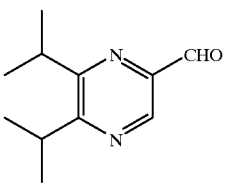

$^1$H-NMR (CDCl$_3$, 400 MHz) δ; 1.31(d,J=6.8 Hz,6H), 1.33(d,J=6.8 Hz,6H), 3.43(hept.,J=6.8 Hz,1H), 3.44(hept., J=6.8 Hz,1H), 8.92(s,1H), 10.12(s,1H).

Referential Example 17

5,5,7,7-tetramethylcyclopenta[b]pyrazine-2-carbaldehyde

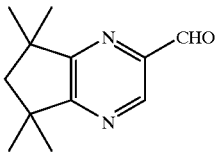

$^1$H-NMR (CDCl$_3$, 400 MHz) δ; 1.38(s,6H), 1.40(s,1H), 2.06(s,2H), 8.94(s,1H), 10.13(s,1H).

Referential Example 18

A mixture of 5,6,7,8-tetrahydro-5,5-dimethylquinoxaline-2-carbaldehyde and 5,6,7,8-tetrahydro-8,8-dimethylquinoxaline-2-carbaldehyde

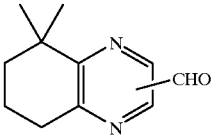

$^1$H-NMR (CDCl$_3$, 400 MHz) δ; 1.37, 1.39(2×s,total 6H), 1.82–1.86(m,2H), 1.93 2.01(m,2H), 3.05 (t,J=6.4 Hz,2H), 8.87, 8.94(2×s,total 1H), 10.09, 10.10(2×s,total 1H).

Referential Example 19

8-Isopropyl-5-methy-1,5,6,7,8-tetrahyroquinoline-2-carbaldehyde

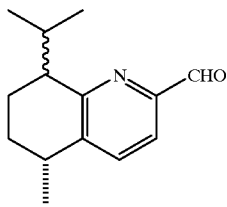

$^1$H-NMR (CDCl$_3$, 400 MHz) δ; 0.63, 0.70(2×d,J=6.8 Hz,total 3H), 1.06, 1.09(2×d,J=6.8 Hz,total 3H), 1.29, 1.:32 (2×d,J=6.8 Hz,total 3H), 1.38–2.09(m,4H), 2.81–3.04(m, 3H), 7.55–7.73(m,2H), 10.01(s,1H).

Referential Example 20

5,5,7,7-Tetramethyl-5,6,7,8-tetrahydroquinoline-2-carbaldehyde

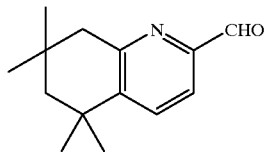

$^1$H-NMR (CDCl$_3$, 400 MHz) δ; 1.04(s,6H), 1.35(s,6H), 1.66(s,2H), 2.81(s,2H), 7.80(s,2H), 10.02 (s,1H).

Referential Example 21

4,8-Dimethylquinoxaline-2-carbaldehyde

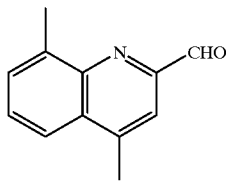

$^1$H-NMR (CDCl$_3$, 400 MHz) δ; 1.55(s,3H), 2.77(d,J=1.0 Hz,3H), 2.90(s,3H), 7.53(dd,J=7.2,8.4 Hz,1H), 7.63–7.67 (m,1H), 7.86(d,J=0.8 Hz,1H), 7.89–7.92(m,1H), 10.23(s, 1H).

Referential Example 22

4-Methoxy-8-methylquinoxaline-2-carbaldehyde

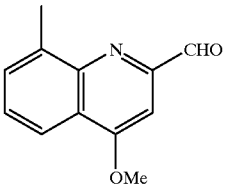

$^1$H-NMR (CDCl$_3$, 400 MHz) δ; 2.80(s,3H), 4.04(s,3H), 7.45(dd,J=6.8,8.4 Hz,1H), 7.32(s,1H), 7.55 –7.58(m,1H), 8.02–8.05(m,1H), 10.10(s,1H).

Referential Example 23

8-Ethyl-4-methylquinoxaline-2-carbaldehyde

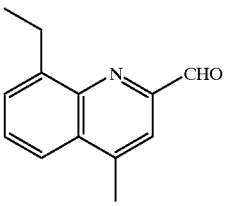

$^1$H-NMR (CDCl$_3$, 400 MHz) δ; 1.34(t,J=7.6 Hz,3H), 2.70(d,J=1.2 Hz,3H), 3.34(q,J=7.6; Hz,2H), 7.55(t,J=7.2 Hz,1H), 7.59(dd,J=2.0,7.2 Hz ,1H), 7.79(d,1, J=0.8 Hz,1H), 7.84(dd,J=2.0,8.0 Hz,1H), 10.12(s,1H).

Referential Example 24

4-Ethyl-8-isopropylquinoxaline-2-carbaldehyde

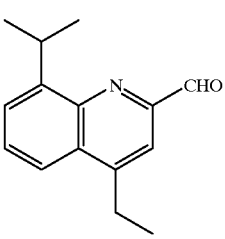

$^1$H-NMR (CDCl$_3$, 400 MHz) δ; 1.41(d,J=7.0 Hz,6H), 1.43(t,J=7.5 Hz,3H), 3.17(dq,J=0.8,7.6 Hz,2H),4.51(hept., J=6.8 Hz,1H), 7.65(t,J=7.2 Hz,1H), 7.69(dd,J=2.0,7.2 Hz,1H), 7.88(s,1H), 7.95(dd,J=2.0,8.0 Hz,1H), 10.20(s,1H).

Referential Example 25

8-Isopropyl-4-phenylquinoxaline-2-carbaldehyde

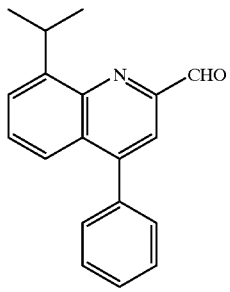

¹H-NMR (CDCl₃, 400 MHz) δ; 1.45(d,J=7.0 Hz,6H),4.56 (hept.,J=7.0 Hz,1H), 7.48–7.56(m,5H), 7.59(dd,J=7.2,8.4 Hz,1H), 7.71(dd,J=1.2,7.2 Hz,1H), 7.82(dd,J=1.6,8.4 Hz,1H), 7.95(s,1H), 10.28(s,1H).

Referential Example 26

4-Ethoxy-8-isopropylquinoxaline-2-carbaldehyde

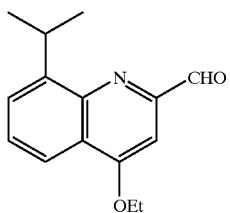

¹H-NMR (CDCl₃, 400 MHz) δ; 1.40(d,J=7.0 Hz,6H), 1.58(t,J=7.0 Hz,3H), 4.34(q,J=7.0 Hz,2H), 4.45(hept.,J=7.0 Hz,1H), 7.34(s,1H), 7.58(dd,J=7.2,8.4 Hz,1H), 7.67(dd, J=1.2,7.6 Hz,1H), 8.13(dd,J=1.2,8.0 Hz,1H), 10.15(s,1H)

Referential Example 27

4-Isopropoxy-8-isopropylquinoxaline-2-carbaldehyde

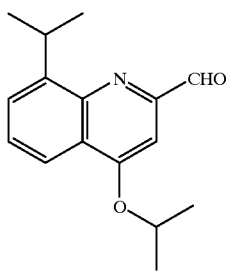

¹H-NMR (CDCl₃, 400 MHz) δ; 1.40(d,J=7.0 Hz,6H), 1.50(d,J=6.0 Hz,6H), 4.40–4.48(m,1H), 4.90–4.96(m,1H), 7.57(dd,J=7.2, 8.4 Hz, 1H), 7.64–7.68(m,1H) 8.12(dd,J=1.2, 8.0 Hz,1H), 10.15(s,1H).

Referential Example 28

8-Ethyl-4-methoxyquinoxaline-2-carbaldehyde

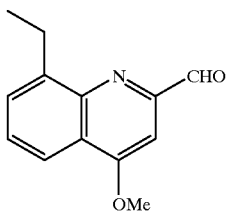

¹H-NMR (CDCl₃, 400 MHz) δ; 1.40(t,J=7.6 Hz,3H), 3.36(q,J=7.5 Hz,2H), 4.11(s,3H), 7.38(s,1H), 7.56(dd,J=7.2, 8.4 Hz,1H), 7.62–7.65(m,1H), 8.10(dd,J=1.6,8.4 Hz,1H), 10.15(s,1H).

Referential Example 29

8-Methylquinoline-2-carbaldehyde

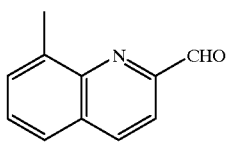

¹H-NMR (CDCl₃, 400 MHz) δ; 2.90(s,1H), 7.57(d(a,J= 6.8,8.0 Hz,1H), 7.66(d,J=6.8 Hz,1H), 7.73(d,J=8.0 Hz,1H), 8.02(d, J=8.8 Hz,1H), 8.27(d,J=8.8 Hz,1H), 10.22(s,1H).

Referential Example 30

8-Isopropylquinoline-2-carbaldehyde

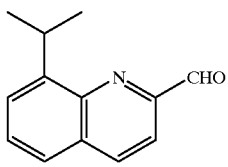

¹H-NMR (CDCl₃, 400 MHz) δ; 1.43(d,J=7.2 Hz,6H), 4.48(quint.,J=7.2 Hz,1H), 7.65(d,J=7.6 Hz,1H),7.71(m,2H), 8.01(d,J=8.4 Hz,1H), 8.27(d,J=8.4 Hz,1H), 10.24(s,1H).

Referential Examples 31

7,8-Dimethylquinoline-2-carbaldehyde

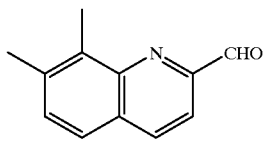

¹H-NMR (CDCl₃, 400 MHz) δ; 2.55(s,3H), 2.84(s,3H), 7.49(d,J=8.4 Hz,1H), 7.64(d,J=8.4 Hz,1H), 7.95(d,J=8.4 Hz,1H), 8.21(d,J=8.4 Hz,1H), 10.23(s,1H).

Referential Example 32

5-Isopropyl-8-methylquinoline-2-carbaldehyde

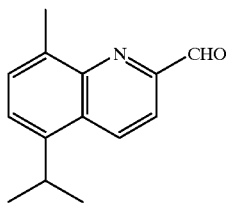

¹H-NMR (CDCl₃, 400 MHz) δ; 1.39(d,J=6.8 Hz,6H), 2.86(s,3H), 3.69(quint.,J=6.8 Hz,1H), 7.49(d,J=7.2 Hz,1H), 7.62(d,J=7.2 Hz,1H), 8.04(d,J=8.4 Hz,1H), 8.58 (d,J=8.4 Hz,1H), 10.24(s,1H).

Referential Example 33

6-Isopropylquinoline-2-carbaldehyde

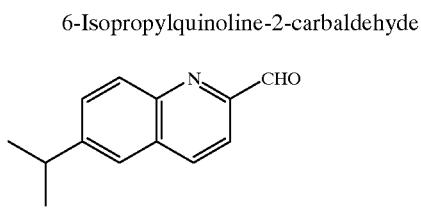

¹H-NMR (CDCl₃, 400 MHz) δ; 1.37(d,J=6.8 Hz,6H), 3.15(quint.,J=6.8 Hz,1H), 7.69(d,J=2.0 Hz,1H),7.74(dd,J=2.0,8.8 Hz,1H), 8.01(d,J=8.4 Hz,1H), 8.18(d,J=8.8 Hz,1H), 8.25(d,J=8.4 Hz,1H), 10.21(s,1ll).

Referential Example 34

7-Isopropylquinoline-2-carbaldehyde

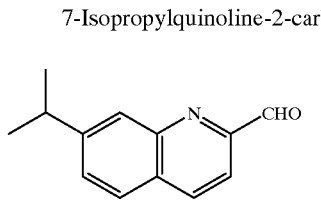

¹H-NMR (CDCl₃, 400 MHz) δ; 1.39(d,J=6.8 Hz,6H), 3.17(quint.,J=6.8 Hz,1H), 7.60(dd,J=2.0,8.8 Hz, 1H), 7.84 (d,J=8.8 Hz,1H), 7.98(d,J=8.4 Hz,1H), 8.07(d,J=2.0 Hz,1H), 8.27(d,J=8.4 Hz,1H), 10.22(s,1H).

Referential Example 35

8-Isopropyl-3-methylquinoline-2-carbaldehyde

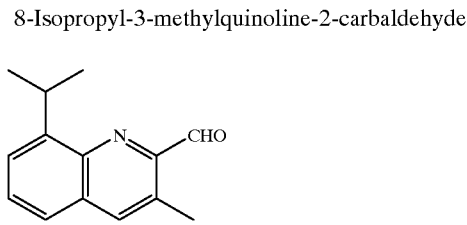

¹H-NMR (CDCl₃, 400 MHz) δ; 1.37(d,J=6.8 Hz,6H), 2.79(s,3H:, 4.44(quint.,J=6.8 Hz,1H), 7.58-7.64(m,3H), 7.98(s,1H), 10.33(s,1H).

Referential Example 36

4,5,6,7-Tetramethylquinoline-2-carbaldehyde

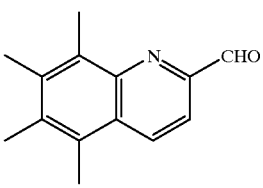

¹H-NMR (CDCl₃, 400 MHz) δ; 2.47(s,3H), 2.49(s,3H), 2.63(s,3H), 2.88(s,3H), 7.95(d,J=8.4 Hz, 1H), 8.45(d,J=8.4 Hz,1H), 10.23(s,1H).

Referential Example 37

8-Phenylquinoline-2-carbaldehyde

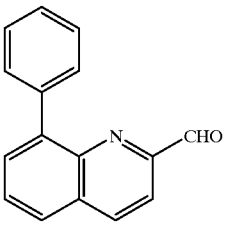

¹H-NMR (CDCl₃, 400 MHz) δ; 7.44–7.55(m,3H), 7.74–7.81(m,3H), 7.85–7.92(m,2H), 8.05(d,J=8.4 Hz,1H), 8.36(d,J=8.4 Hz,1H).

Referential Example 38

1-Isopropyl-2,3-dimethylindoline-5-carbaldehyde

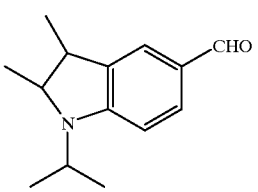

¹H-NMR (CDCl₃, 400 MHz) δ; 1.10(d,J=6.4 Hz,3H), 1.26(d,J=6.8 Hz,3H), 1.29(d,J=6.8 Hz,3H), 1.38(d,J=6.8 Hz,3H), 3.37(hept.,J=7.2 Hz,1H), 3.75–3.82(m,1H), 4.00–4.04(m,1H), 6.37(d,J=8.4 Hz,1H), 7.48–7.52(m,2H), 9.62(s,1H).

Referential Example 39

1-Isopropyl-2-methylindoline-5-carbaldehyde

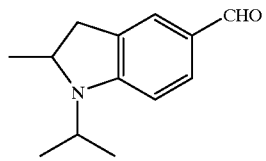

$^1$H-NMR (CDCl$_3$, 400 MHz) δ; 1.28(d,J=6.4 Hz,3H), 1.29(d,J=(6.8 Hz,3H), 1.35(d,J=7.2 Hz,3H), 2.59(dd,J:=5.2, 16.0 Hz,3H), 3.25(dd,J=10.0,16.4 Hz,3H), 3.77(hept.,J=6.8 Hz,1H), 4.05–4.10(m,1H), 6.37(d,J=8.4 Hz,1H), 7.50–7.52 (m,2H), 9.61(s,1H).

Referential Example 40

1,4-Dimethyl-1,2,3,4-tetrahydroquinoline-6-carbaldehyde

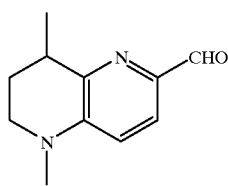

$^1$H-NMR (CDCl$_3$, 400 MHz) δ; 1.30(d,J=7.2 Hz,3H), 1.66–1.74(m,1H), 1.95–2.03(m,1H), 2.86–2.94 (m,1H), 3.02(s,3H), 3.33–3.46(m,2H), 6.57(d,J=9.2 Hz,1H), 7.55–7.58(m,2H), 9.68(s,1H).

Referential Example 41

1,4,4-Trimethyl-1,2,3,4-tetrahydroquinoline-6-carbaldehyde

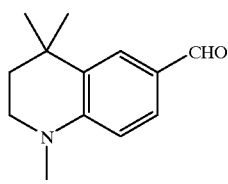

$^1$H-NMR (CDCl$_3$, 400 MHz) δ; 1.30(s,6H), 1.74(t,J=6.4 Hz,2H), 3.03(s,3H), 3.40(t,J=6.0 Hz,2H), 6.57(d,J=8.4 Hz,1H), 7.56(dd,J=2.0,8.8 Hz,1H), 7.70(d,J=2.0 Hz,1H), 9.68(s,1H).

Referential Example 42

1,515-Trimethyl-2,3,4,5-teatrahydro-1H-benzazepine-7-carbaldehyde

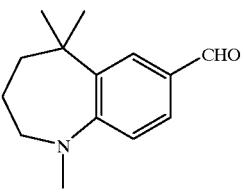

$^1$H-NMR (CDCl$_3$, 400 MHz) δ; 1.39(s,6H), 1.66(t,J=6.4 Hz,2H), 1.78–1.86(m,2H), 2.97(s,3H), 3.05(t,J=5.6 Hz,2H), 6.95(d,J=8.4 Hz,1H), 7.61(dd,J=2.0,8.4 Hz,1H), 7.83(d,J=1.6 Hz,1H), 9.82(s,1H).

Referential Example 43

1,4-Diisopropyl-1,2,3,4-tetrahydroquinoxaline-6-carbaldehyde

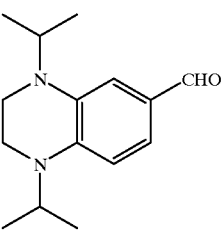

$^1$H-NMR (CDCl$_3$, 400 MHz) δ; 1.19(d,J=6.5 Hz,6H), 1.23(d,J=6.5 Hz,6H), 3.11(d,J=645 Hz,1H), 3.13(d,J=5.0 Hz,1H), 3.38(d,J=5.0 Hz,1H), 3.39(d,J=6.5 Hz,1H), 4.17 (hept.,J=6.5 Hz,2H), 6.65(d,J=8.0 Hz,1H), 7.14(d,J=2.0 Hz,1H), 7.16(dd,J=2.0,8.0 Hz, 1H), 9.64(s,1H).

Referential Example 44

4-Isopropyl-3,4-dihydro-2H-1,4-benzoxazine-7-carbaldehyde

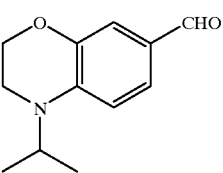

$^1$H-NMR (CDCl$_3$, 400 MHz) δ; 1.23(d,J=6.8 Hz,6H), 3.35(t,J=4.8 Hz,2H), 4.20(t,J=4.4 Hz,2H), 4.20(hept.,J=6.8 Hz,1H), 6.78(d,J=8.4 Hz,1H), 7.28(d,J=2.0 Hz,1H), 7.38 (dd,J=2.0,8.8Hz,1H), 9.68(s,1H).

Referential Example 45

5-Isopropyl-1-(2,2,2-trifluoroethyl)pyrazole-3-carbaldehyde

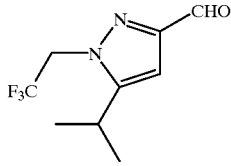

¹H-NMR (CDCl₃, 400 MHz) δ; 1.28(d,J=6.0 Hz,6H), 2.92–3.04(m,1H), 4.76(dd,J=8.0,16.4 Hz,2H), 6.66(s,1H), 9.94(s,1H).

Referential Example 46

5,6,7,8-Tetrahydro-5,5,8,8-tetramethylquinoxaline-2-carboxylic acid

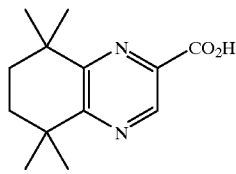

¹H-NMR (CDCl₃, 400 MHz) δ; 1.36(s,12H), 1.85(s,4H), 9.19(s,1H).

Referential Example 47

5,5,7,7-Tetramethylcyclopenta[b]pyrazine-2-carboxylic acid

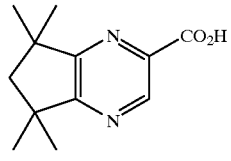

¹H-NMR (CDCl₃, 400 MHz) δ; 1.39(s,6H), 1.40(s,6H), 2.08(s,2H), 9.23(s,1H).

Referential Example 48

2,3-Dicyclopentylpyrazine-2-carboxylic acid

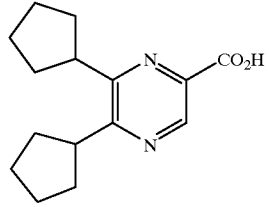

¹H-NMR (CDCl₃, 400 MHz) δ; 1.67–1.82(m,4H), 1.82–1.98(m,8H), 2.00–2.12(m,4H), 3.50–3.60(m, 2H), 9.16(s,1H).

Referential Example 49

Methyl 7,8,9,10-tetrahydro-7,7,10,10-tetramethylphenazine-3-carboxylate

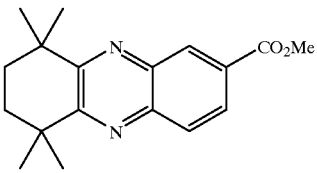

In 2.5 ml of acetic acid were dissolved 962 mg of 3,3,6,6-tetramethyl-1,2-cyclohexanedione and 1.0 g of methyl 3,4-diaminobenzoate. The resulting solution was heated under reflux for 8 hours. After the reaction mixture was allowed to cool down, wager was added. The resulting mixture was extracted with ethyl acetate. The organic layer was successively washed with a saturated aqueous solution of sodium bicarbonate, water and saturated saline, dried over anhydrous magnesium sulfate and concentrated under reduced pressure. The residue so obtained was subjected to chromatography on a silica gel column (developing solvent: 5% ethyl acetate/n-hexane), whereby 1.17 g of the title compound were obtained in the form of a pale yellow oil.

¹H-NMR (CDCl₃, 400 MHz) δ; 1.43(s,6H), 1.44(s,6H), 1.92(s,4H), 3.99(s,3H), 8.01(d,J=8.8 Hz, 1H), 8.22(dd,J= 2.0,8.8 Hz,1H), 8.71(d,J=1.8 Hz,1H).

Referential Examples 50

2,3-Diisopropylquinoxaline-6-carbaldehyde

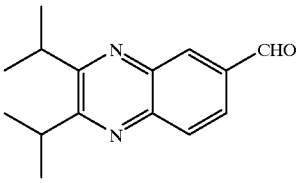

Step 1

Methyl 2,3-diisopropylquinoxaline-6-carboxylate

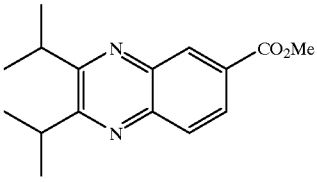

In a similar manner to Referential Example 49, the title compound was obtained.

¹H-NMR (CDCl₃, 400 MHz) δ; 1.39(d,J=6.6 Hz,12H), 3.50–3.60(m,2H), 3.99(s,3H), 8.02(d,J=8.8 Hz, 1H), 8.23 (dd,J=2.0,8.8 Hz,1H), 8.73(d,J=1.8 Hz,1H).

Step 2

2,3-Diisopropylquinoxaline-6-carbaldehyde

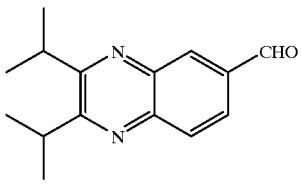

Reduction and oxidation were carried out as in Referential Example 1, whereby the title compound was obtained.

Melting point: 53 to 55° C.;

$^1$H-NMR (CDCl$_3$, 400 MHz) δ; 1.41(d,J=6.8 Hz,12H), 3.56(hept.,J=6.8 Hz,2H), 8.08(d,J=8.8 Hz,1H), 8.11–8.14 (m,1H), 8.49(d,J=1.6 Hz,1H), 10.22(s,1H).

Example 93

4-[1-(1-tert-Butyl-5-isopropylpyrazol-3-yl)ethen-1-yl]benzoic acid

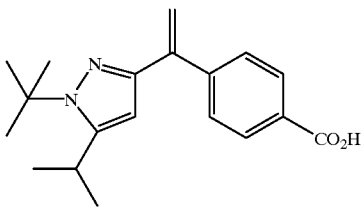

Step 1

α-(1-tert-Butyl-5-isopropylpyrazol-3-yl)-4-(4,4-dimethyl-1,3-oxazolin-2-yl)benzyl alcohol

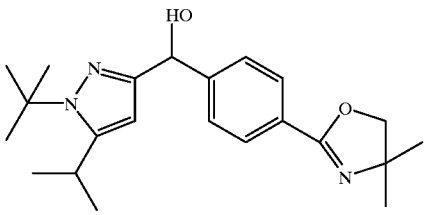

To 20 ml of a solution of 1.15 g of 4-bromo-1-(4,4-dimethyl-1,3-oxazolin-2-yl)benzene in tetrahydrofuran, 3.23 ml of n-BuLi (1.53M hexane solution) were added dropwise at −78° C. under stirring, followed by stirring at the same temperature for 15 minutes. To the reaction mixture was added dropwise a solution of 0.8 g of 1-tert-butyl-5-isopropylpyrazole-3-carbaldehyde in 5 ml of tetrahydrofuran. The resulting mixture was stirred for 30 minutes. After the reaction, 10 ml of a saturated aqueous solution of ammonium chloride were added to the reaction mixture and the resulting mixture was extracted with ethyl acetate. The organic layer was washed with saturated saline, dried over anhydrous magnesium sulfate and concentrated under reduced pressure. The residue so obtained was subjected to chromatography on a silica gel column (developing solvent: 50% ethyl acetate/n-hexane), whereby 0.82 g of the title compound was obtained in the form of a colorless oil.

$^1$H-NMR (CDCl$_3$, 400 MHz) δ; 1.26(d,J=6.0 Hz,3H), 1.28(d,J=6.0 Hz,3H), 1.38(s,6H), 1.64(s,9H), 3.24–3.30(m, 1H), 4.10(s, 2H), 5.73(s,1H), 5.81(s,1H), 7.48(d,J=8.0Hz, 2H), 7.9l(d,J=8.0 Hz,2H).

Step 2

1-(4,4-Dimethyl-1,3-oxazolin-2-yl)-4-phenyl 1-tert-butyl-5-isopropyl-3-pyrazolyl ketone

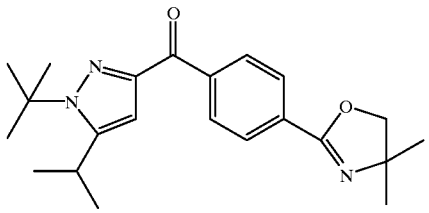

In 10 ml of dichloromethane was dissolved 0.8 g of α-(1-tert-butyl-5-isopropylpyrazol-3-yl)-4-(4,4-dimethyl-1, 3-oxazolin-2-yl)benzyl alcohol, followed by the addition of 20 g of manganese dioxide. The resulting mixture was stirred at room temperature for 5 hours. Manganese dioxide was filtered off through Celite and the solvent was distilled off. The residue was subjected to chromatography on a silica gel column (developing solvent: 20% n-hexane/ethyl acetate), whereby 395 mg of the title compound were obtained in the form of a colorless oil.

$^1$H-NMR (CDCl$_3$, 400 MHz) δ; 1.32(d,J=6.0 Hz,6H), 1.40(s,6H), 1.70(s,9H), 3.35–3.42(m,1H), 4.14(s,2H), 6.88 (s,1H), 8.02(d,J=8.0 Hz, 2H), 8.37(d,J=8.0 Hz,2H).

Step 3

α-(1-tert-Butyl-5-isopropylpyrazol-3-yl)-4-(4,4-dimethyl-1,3-oxazolin-2-yl)styrene:.

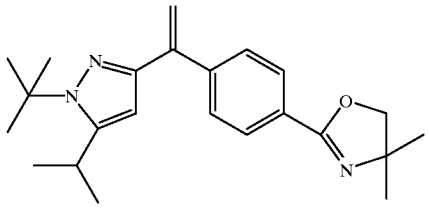

In 10 ml of a suspension of 136 mg of sodium amide in tetrahydrofuran were added 420 mg of methyltriphenylphosphonium bromide eat room temperature, followed by stirring for 24 hours. To the reaction mixture were added 3 ml of a solution of 288 mg of 1-(4,4-dimethyl-1,3-oxazolin-2-yl)-4-phenyl 1-tert-butyl-5-isopropyl-3-pyrazolyl keztone in tetrahydrofuran. The resulting mixture was stirred for 2 hours. After the reaction, 5 ml of a saturated aqueous solution of ammonium chloride were added and the resulting mixture was extracted with ethyl acetate. The organic layer was washed with saturated saline, dried over anhydrous magnesium sulfate and concentrated under reduced pressure. The residue so obtained was subjected t0 chromatography on a silica gel column (developing solvent: 20% n-hexane/ethyl acetate), whereby 280 mg of the title compound were obtained in the form of a colorless oil.

$^1$H-NMR (CDCl$_3$, 400 MHz) δ; 1.26(d,J=6.0 Hz,6H), 1.39(s,6H), 1.68(s,9H), 3.32–3.40(m,1H), 4.10(s,2H), 5.35 (d,J=1.6 Hz,1H), 5.82(d,J=1.6 Hz,1H), 6.07(s,1H), 7.55(d, J=8.0 Hz,2H), 7.90(d,J=8.0 Hz,2H).

Step 4

4-[1-(1-tert-Butyl-5-isopropylpyrazol-3-yl)ethen-1-yl]benzoic acid

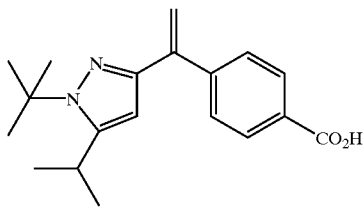

To 5 ml of 130 mg of α-(1-tert-butyl-5-isopropylpyrazol-3-yl)-4-(4,4-dimethyl-1,3-oxazolin-2-yl)styrene in ethanol was added 0.4 ml of a 3N aqueous solution of an acid at room temperature. The resulting mixture wag heated under reflux for 30 minutes. To the reaction mixture was added a 5N aqueous solution of sodium hydroxide to adjust its pH to 11, followed by extraction with dichloromethane. The organic layer was washed with saturated saline, dried over anhydrous magnesium sulfate and concentrated under reduced pressure. To a solution of the residue in 3 ml of 1,4-dioxane were added 100 mg of lithium hydroxide and the resulting mixture was heated at 100° C. for 2 hours. After the completion of the reaction, a 3N aqueous solution of hydrochloric acid was added to adjust the pH to 5, followed by extraction with ethyl acetate. The organic layer was washed with saturated saline, dried over anhydrous magnesium sulfate and concentrated under reduced pressure. The residue so obtained was subjected to chromatography on a silica gel column (developing solvent: 50% dichloromethane/ethyl acetate), whereby 4 mg of the title compound were obtained as a pale yellow solid.

$^1$H-NMR (DMSO-$d_6$, 400 MHz) δ; 1.26(d,J=6.0 Hz,6H), 1.64(s,9H), 3.36–3.40(m,1H), 5.40(d,J=2.0 Hz, 1H), 5.87(d, J=2.0 Hz,1H), 6.11(s,1H), 7.63(d,J=8.8 Hz,2H), 8.07(d, J=8.8 Hz,2H).

Example 94

N-(4-Hydroxyphenyl)-4-{2-{5-[3-(1-tert-butyl-5-isopropylpyrazolyl)]pyrrolyl}}benzoic acid amide

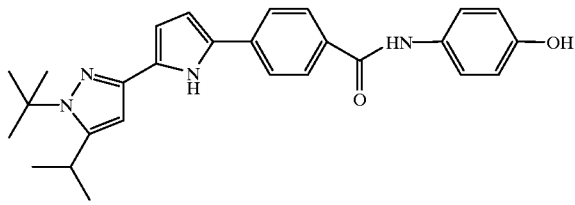

In 5 ml of a solution of 98 mg of 4-{2-{5-[3-(1-tert-butyl-5-isopropylpyrazolyl)]pyrrolyl}}benzoic acid in N,N-dimethylformamide were added 57 mg of dimethyl chlorophosphate and 46 μl of triethylamine. The resulting mixture was stirred for 40 minutes. To the reaction mixture were added 2 ml of a solution of 40 mg of 4-aminophenol in N,N-dimethylformamide at 0° C., followed by stirring at room temperature for 24 hours. Water was added to the reaction mixture and the resulting mixture was extracted with ethyl acetate. The organic layer was successively washed with a 10% aqueous solution of hydrochloric acid, a saturated aqueous solution of sodium bicarbonate and saturated saline, dried over anhydrous magnesium sulfate and concentrated under reduced pressure. The residue so obtained was subjected to chromatography on a silica gel column (developing solvent: 33% ethyl acetate/n-hexane). The solid so obtained was washed with methonol, whereby 3 mg of the title compound were obtained in the form of a colorless solid.

$^1$H-NMR (DMSO-$d_6$, 400 MHz) δ; 1.26(d,J=6.8 Hz,6H), 1.60(s,9H), 6.36(s,1H), 6.58(s,1H), 6.68(br s,1H), 6.71(d,J= 8.4 Hz,2H), 7.51(d,J=8.4 Hz,2H), 7.83(d,J=8.4 Hz,2H), 7.90 (d,J=8.4 Hz,2H), 9.22(s,1H), 9.92(s,1H), 11.15(s,1H).

In a similar manner to Example 93 or 94, the compounds which will be described below were obtained.

Example 95

4-{4-{2-[3-(1-tert-Butyl-5-isopropylpyrazolyl)]furyl}}benzoic acid

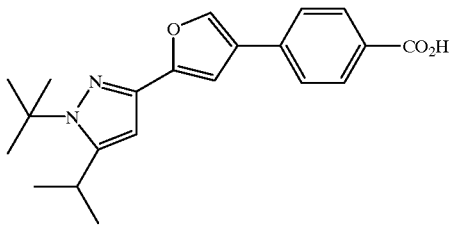

$^1$H-NMR (DMSO-$d_6$, 400 MHz) δ; 1.26(d,J=6.83 Hz,6H), 1.60(s,9H), 3.36–3.40(m,1H), 6.51(s,1H), 7.12(s, 1H), 7.77(d,J=8.4 Hz,2H), 7.93(d,J=8.,4 Hz,2H), 8.29(s, 1H).

Example 96

4-{4-{2-[3-(1-tert-Butyl-5-isopropylpyrazolyl)]-1-methylpyrrolyl}}benzoic acid

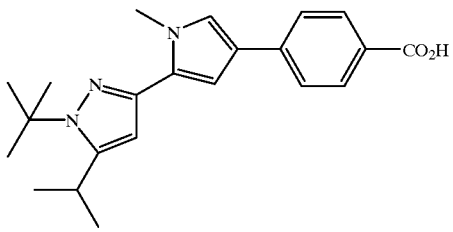

$^1$H-NMR (DMSO-$d_6$, 400 MHz) δ; 1.24(d,J=6.8 Hz,6H), 1.60(s,911), 3.38–3.42(m,1H), 3.88(s,3H), 6.44(s,1H), 6.75 (d,J=2.4 Hz,1H), 7.35(d,J=2.4 Hz,1H), 7.61(d,J=8.4 Hz,2H), 7.85(d,J=8.4 Hz,2H).

Example 97

4-{4-{2-[3-(1-tert-Butyl-5-isopropylpyrazolyl)]-1-isopropylpyrrolyl}}benzoic acid

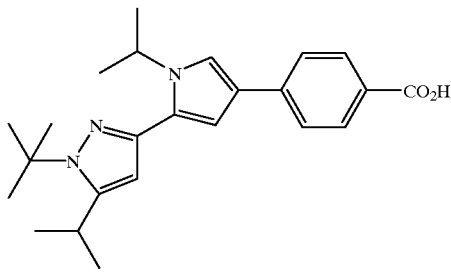

¹H-NMR (DMSO-d₆, 400 MHz) δ; 1.24(d,J=6.8 Hz,6H), 1.40(d,J=6.8 Hz,6H), 1.59(s,9H), 3.30–3.41(m, 1H), 5.22–5.32(m,1H), 6.43(s,1H), 6.71(d,J=2.0 Hz,1H), 7.58(d,J=2.0 Hz,1H), 7.66(d,J=8.4 Hz,2H), 7.84(d,J=8.4 Hz,2H).

Example 98

4-{2-{5-{3-[1-(2,2,2-Trifluoroethyl)-5-isopropylpyrazolyl]}pyrrolyl}}benzoic acid

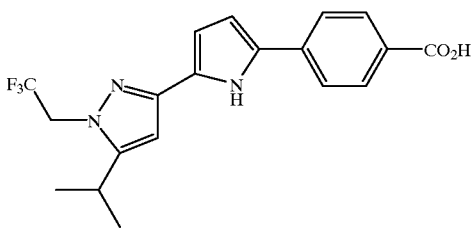

¹H-NMR (DMSO-d₆, 400 MHz) δ; 1.22(d,J=6.0 Hz,6H), 3.08–3.18(m,1H), 5.08(dd,J=8.0,16.4 Hz,2H), 6.47(t,J=2.8 Hz,1H), 6.64(s,1H), 6.72(t,J=2.8 Hz,2H), 7.85(d,J=8.0 Hz,2H), 7.88(d,J=8.0 Hz,2H), 11.48(s,1H).

Example 99

4-{2-{5-[3-(1tert-Butyl-5-isopropylpyrazolyl)]pyrrolyl}}benzoic acid

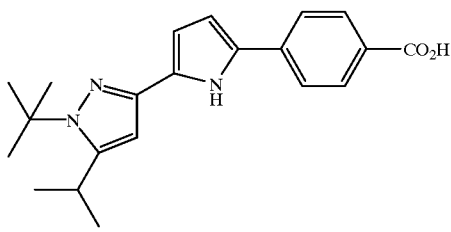

¹H-NMR (DMSO-d₆, 400 MHz) δ; 1.24(d,J=6.0 Hz,6H), 1.60(s,9H), 3.34–3.44(m,1H), 6.37(t,J=2.8 Hz,1H), 6.60(s,1H), 6.68(t,J=2.8 Hz,1H), 7.82(d,J=8.4 Hz,2H), 7.87(d,J=8.4 Hz,2H), 11.25(s,1H).

Example 100

4-{2-{5-[3-(1-tert-Butyl-5-isopropyl-4-methylpyrazolyl)]pyrrolyl}}benzoic acid

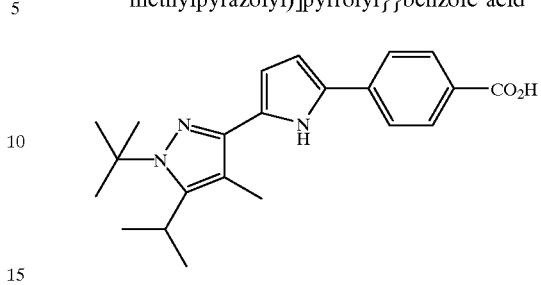

¹H-NMR (DMSO-d₆, 400 MHz) δ; 1.30(d,J=7.2 Hz,6H), 1.61(s,9H), 2.13(s,3H), 6.21(br s,1H), 6.72(br s,1H), 7.81 (d,J=8.4 Hz,2H), 7.86(d,J=8.4 Hz,2H).

Example 101

6-{2-{5-[3-(1-tert-butyl-5-isopropylpyrazolyl)]pyrrolyl}}nicotinic acid

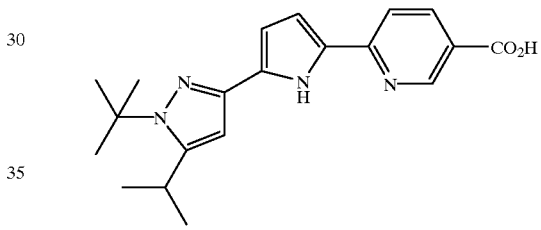

¹H-NMR (DMSO-d₆, 400 MHz) δ; 1.24(d,J=6.0 Hz,6H), 1.62(s,9H), 3.32–3.44(m,1H), 6.56(br s,1H), 6.82(s,1H), 7.36(br s,1H), 8.18(d,J=8.9 Hz,1H), 8.34(dd,J=1.6,8.8 Hz,1H), 8.80(d,J=1.6 Hz,1H).

Example 102

4-{2-{5-[3-(1-tert-Butyl-5-isopropylpyrazolyl)]pyrrolyl}}benzoic acid

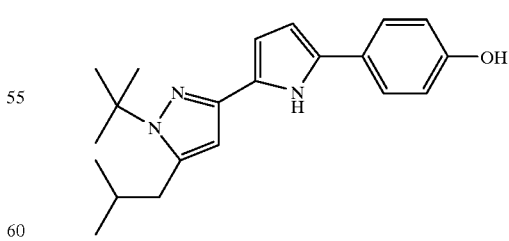

¹H-NMR (DMSO-d₆, 400 MHz) δ; 1.00(d,J=6.0 Hz,6H), 1.60(s,9H), 1.92–2.04(m,1H), 2.68(d,J=7.2 Hz, 2H), 6.40(t, J=2.8 Hz,1H), 6.56(s,1H), 6.69(t,J=2.8 Hz,1H), 7.83(d, J=8.4 Hz,2H), 7.84(d,J=8.4 Hz,2H), 11.25(s,1H).

Example 103

6-{2-{5-[3-(1-tert-Butyl-5-isopropylpyrazolyl)]pyrrolyl}}nicotinic acid

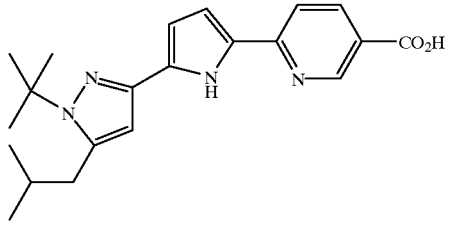

$^1$H-NMR (DMSO-$d_6$, 400 MHz) δ; 1.00(d,J=6.8 Hz,6H), 1.59(s,9H), 1.93–2.20(m,1H), 2.66(d,J=7.2 Hz, 2H), 6.44(t, J=2.4 Hz,1H), 6.71(s,1H), 6.93(t,J=2.4 Hz,1H), 7.80(d, J=8.4 Hz,1H), 8.12(dd,J=2.0,8.4 Hz,1H), 8.95(d,J=2.0 Hz,1H), 11.32(s,1H).

Example 104

4-{2-{5-{3-[5-Isopropyl-1-(2,5-dimethylphenyl)pyrazolyl]}pyrrolyl}}benzoic acid

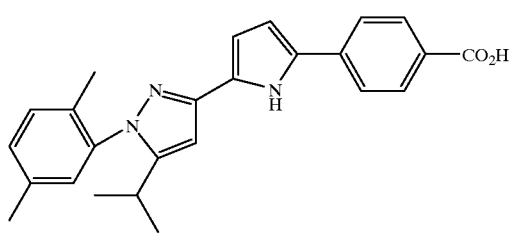

$^1$H-NMR (DMSO-$d_6$, 400 MHz) δ; 1.12(d,J=6.8 Hz,6H), 1.94(s,3H), 2.32(s,3H), 2.58–2.63(m,1H), 6.49(dd,J=2.4,4.0 Hz,1H), 6.69(s,1H), 6.72(dd,J=2.8,4.0 Hz,1H), 7.17(br s,1H), 7.24(d,J=8.0 Hz,1H), 7.29(d,J=8.0 Hz,1H), 7.86(s, 4H), 11.52(s,1H).

Example 105

4-{2-{5-[3-(1,2-Diisopropylpyrazolyl)]pyrrolyl}}benzoic acid

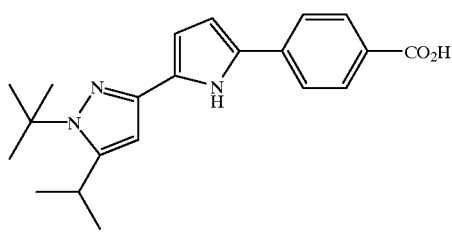

$^1$H-NMR (DMSO-$d_6$, 400 MHz) δ; 1.23(d,J=6.8 Hz,6H), 1.44(d,J=6.8 Hz,6H), 3.02–3.10(m,1H), 4.52–4.63(m,1H), 6.55(t,J=4.0 Hz,1H), 6.57(s,1H), 6.73(dd,J=2.8,3.6 Hz, 1H), 7.88(s,4H), 11.52(s,1H)

Example 106

4-{2-{5-[3-(1-tert-Butyl-5-isopropylpyrazolyl)]-1-isopropylpyrrolyl}}benzoic acid

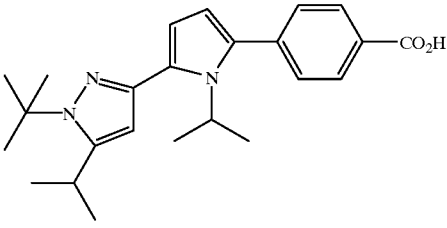

$^1$H-NMR (DMSO-$d_6$, 400 MHz) δ; 1.25(d,J=6.8 Hz,6H), 1.40(d,J=6.8 Hz,6H), 1.61(s,9H), 3.32–3.40(m, 1H), 4.60–4.70(m,1H), 6.12(d,J=3.6 Hz,1H), 6.27(d,J=3.6 Hz,1H), 6.32(s,1H), 7.47(d,J=8.8 Hz,2H), 7.96(d,J=8.8 Hz,2H).

Example 107

6-{2-{5-[3-(1-tert-Butyl-5-isopropylpyrazolyl)]-1-isopropylpyrrolyl}}nicotinic acid

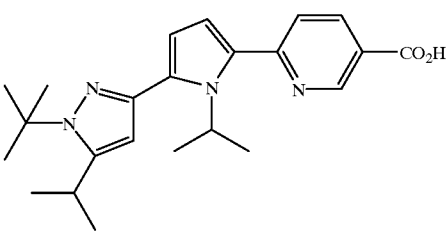

$^1$H-NMR (DMSO-$d_6$, 400 MHz) δ; 1.31(d,J=6.8 Hz,6H), 1.55(d,J=6.8 Hz,6H), 1.69(s,9H), 3.70–3.84(m, 1H), 5.28–5.42(m,1H), 6.26(s,1H), 6.35(d,J=4.0 Hz,1H), 6.56(d, J=4.0 Hz,1H), 7.54(d,J=8.4 Hz,1H), 8.20(dd,J=2.0,8.4 Hz,1H), 9.20(d,J=2.0 Hz,1H).

Example 108

4-{2-{5-[3-(1,5-Diisopropylpyrazolyl)]-1-isopropylpyrrolyl}}benzoic acid

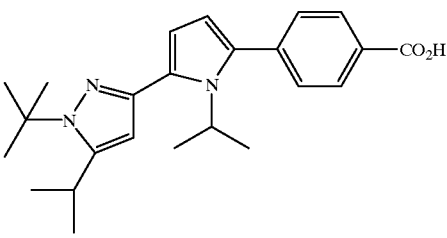

$^1$H-NMR (DMSO-$d_6$, 400 MHz) δ; 1.22(d,J=6.8 Hz,6H), 1.40(d,J=6.8 Hz,6H), 1.41(d,J=6.8 Hz,6H), 3.00–3.10(m, 1H), 4.52–4.64(m,2H), 6.13(s,1H), 6.13(d,J=4.0 Hz,1H), 6.28(d,J=4.0 Hz,1H), 7.48(d,J=8.4 Hz,2H), 7.97(d,J=8.4 Hz,2H).

Example 109

6-{2-{5-[3-(1,5-Diisopropylpyrazolyl)]pyrrolyl}}nicotinic acid

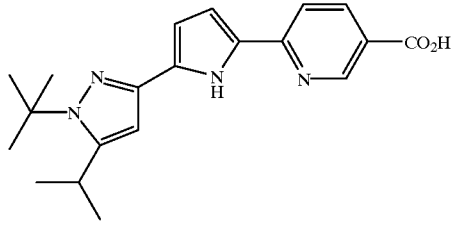

$^1$H-NMR (DMSO-$d_6$, 400 MHz) δ; 1.21(d,J=6.8 Hz,6H), 1.42(d,J=(6.8 Hz,6H), 3.00–3.10(m,1H), 4.48–4.56(m,1H), 6.48(t,J=2.8 Hz,1H), 6.60(s,1H), 6.96(dd,J=2.8,3.2 Hz, 1H), 7.86(d,J=8.0 Hz,1H), 8.14(dd,J=2.0,8.0 Hz,1H), 8.95(d,J=2.0 Hz, 1H).

Example 110

4-{2-{5-[3-(1,5-Diisopropyl-4-methylpyrazolyl)]pyrrolyl}}benzoic acid

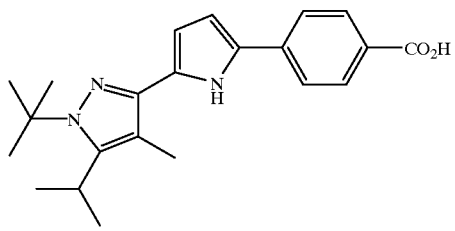

$^1$H-NMR (DMSO-$d_6$, 400 MHz) δ; 1.28(d,J=6.8 Hz,6H), 1.41(d,J=6.8 Hz,6H), 2.10(s,3H), 3.20–3.30(m, 1H), 4.52–4.64(m,1H), 6.24(br s,1H), 6.72(br s,1H), 7.84(s,4H), 11.21(br s,1H).

Example 111

4-{2-{5-[3-(5-Isobutyl-1-isopropylpyrazolyl)]pyrrolyl}}benzoic acid

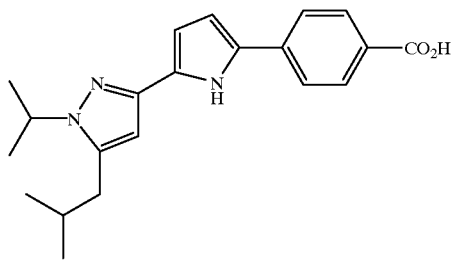

$^1$H-NMR (DMSO-$d_6$, 400 MHz) δ; 0.94(d,J=6.8 Hz,6H), 1.37(d,J=6.8 Hz,6H), 1.80–1.92(m,1H), 2.52(d, J=6.0 Hz,2H), 4.42–4.54(m,1H), 6.40(br s,1H), 6.41(s,1H), 6.69(br s,1H), 7.86(s,4H).

Example 112

4-{2-{5-[3-(5-Isobutyl-1-isopropyl-4-methylpyrazolyl)]pyrrolyl}}benzoic acid

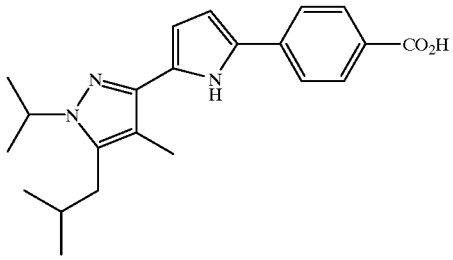

$^1$H-NMR (DMSO-$d_6$, 400 MHz) δ; 0.92(d,J=6.8 Hz,6H), 1.40(d,J=6.8 Hz,6H), 1.70–1.82(m,1H), 2.04(s, 3H), 4.44–4.52(m,1H), 6.29(dd,J=2.0,3.6 Hz,1H),6.74(dd,J=2.8, 3.6 Hz,1H), 7.87(s,4H).

Example 113

4-{2-{5-[3-(1-Ethy-5-isopropylpyrazolyl)]pyrrolyl}}benzoic acid

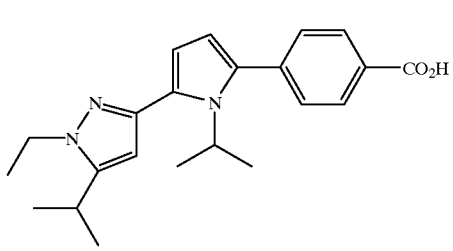

$^1$H-NMR (DMSO-$d_6$, 400 MHz) δ; 1.24(d,J=6.8 Hz,6H), 1.35(t,J=6.8 Hz,3H), 2.94–3.14(m,1H), 4.07(q, J=6.8 Hz,2H), 6.40(t,J=2.0 Hz,1H), 6.45(s,1H), 6.93(t,J=2.4 Hz,1H), 7.84(d,J=8.8 Hz,2H), 7.86(d,J=8.8 Hz,2H).

Example 114

4-{2-{5-[3-(5-Isopropyl-1-propylpyrazolyl)]pyrrolyl}}benzoic acid

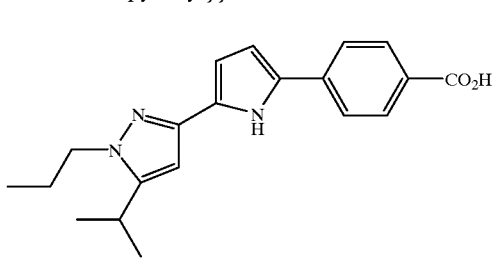

$^1$H-NMR (DMSO-$d_6$, 400 MHz) δ; 0.87(t,J=7.6 Hz,3H), 1.22(d,J=6.8 Hz,6H), 1.70–1.82(m,2H), 2.96–3.14(m,1H), 3.98(t,J=7.6 Hz,2H), 6.40(t,J=2.4 Hz,1H), 6.45(s,1H), 6.69(t,J=2.8 Hz,1H), 7.83(d,J=8.4 Hz,2H), 7.86(d,J=8.4 Hz,2H).

Example 115

5-{2-{5-[3-(1-Ethyl-5-isopropylpyrazolyl)]pyrrolyl}}thiophene-2-carboxylic acid

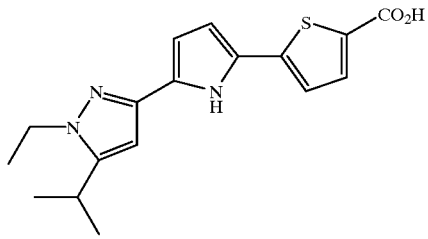

¹H-NMR (DMSO-d₆, 400 MHz) δ; 1.22(d,J=6.8 Hz,6H), 1.34(t,J=7.2 Hz,3H), 2.94–3.12(m,1H), 4.07(q,J=7.2 Hz,2H), 6.36(dd,J=2.4,3.6 Hz,1H), 6.40(s,1H), 6.48(dd,J=2.8,3.6 Hz,1H), 7.43(d,J=3.6 Hz,1H), 7.60(d,J=3.6 Hz,1H), 11.58(br s, 1H).

Example 116

4-{2-{5-{2-[8-Isopropyl-4-(2-furyl)quinolyl]}pyrrolyl}}benzoic acid

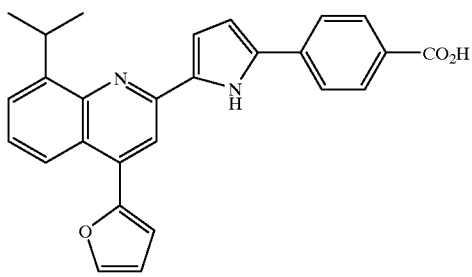

¹H-NMR (DMSO-d₆, 400 MHz) δ; 1.36(d,J=6.8 Hz,6H), 4.48–4.58(m,1H), 6.80–6.83(m,1H), 6.87–6.91 (m,1H), 7.16–7.19(m,1H), 7.26–7.29(m,1H), 7.48–7.54(m,1H), 7.63–7.66(m,1H), 7.97(s,4H), 8.06(br s,1H), 8.21–8.25(m,1H), 8.30(s, 1H), 11.73(br s,1H).

Example 117

4-(1-tert-Butyl-5-isoprolpylpyrazole-3-carbamoyl)benzoic acid

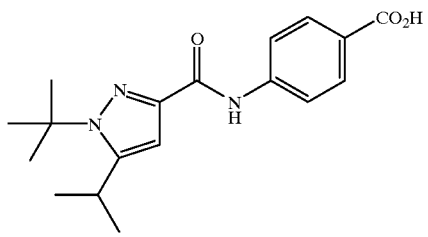

¹H-NMR (DMSO-d₆, 400 MHz) δ; 1.23(d,J=6.8 Hz,6H), 1.64(s,9H), 3.36–3.43(m,1H), 7.88(br s,4H), 9.84(s,1H).

Example 118

Methyl 4-{4-[2-(5,6-diisopropylpyrazinyl)]-4-oxo-1-butanoyl}benzoate

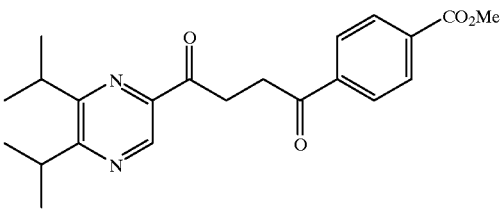

¹H-NMR (CDCl₃, 400 MHz) δ; 1.31(d,J=6.8 Hz,6H), 1.34(d,J=6.8 Hz,6H), 3.38–3.47(m,2H), 3.47(t,J=6.4 Hz,2H), 3.69(t,J=6.4 Hz,2H), 3.96(s,3H), 8.08(d,J=8.4 Hz,2H),8.15(d,J=8.4 Hz,2H), 8.97(s,1H).

Example 119

Methyl 4-{4-[3-(1-tert-butyl-5-isopropylpyrazolyl)]-4-oxo-1-butanoyl}benzoate

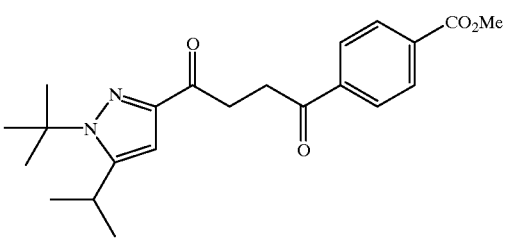

¹H-NMR (CDCl₃, 400 MHz) δ; 1.28(d,J=6.0 Hz,6H), 1.68(s,9H), 3.32–3.40(m,1H), 3.40–3.50(m,4H), 3.94(s,3H), 6.68(s,1H), 8.07(d,J=8.4Hz,2H), 8.12(d,J=8.4 Hz,2H).

Example 120

Methyl 4-{4-[2-(8-Isopropyl-4-methoxyquinolyl)]-4-oxo-1-butanoyl}benzoate

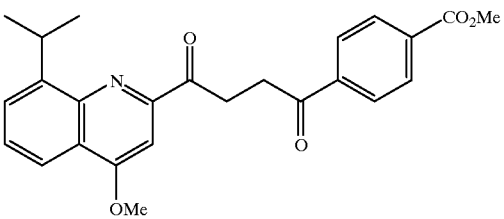

¹H-NMR (CDCl₃, 400 MHz) δ; 1.42(d,J=7.0 Hz,6H), 3.53(t,J=6.0 Hz,2H), 3.91(t,J=6.4 Hz,2H), 4.08(s,3H), 4.37 (hept.,J=7.0 Hz,1H), 7.49(s,1H), 7.56(dd,J=7.2,8.4 Hz,1H), 7.65(dd,J=1.2,7.2 Hz,1H), 8.08(dd,J=1.6,8.4 Hz,1H), 8.11(d,J=8.8 Hz,2H), 8.15(d, J=8.4 Hz,2H).

In a similar manner to the above Referential Example, the compounds which will be described below were obtained.

Referential Example 51

1-tert-Butyl-5-isobutyl-4-methylpyrazole-3-carbaldehyde

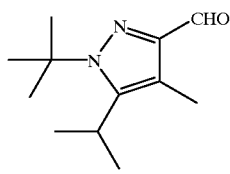

¹H-NMR (CDCl₃, 400 MHz) δ; 1.35(d,J=6.8 Hz,6H), 1.67(s,9H), 2.37(s,3H), 3.48–3.58(m,1H), 9.93(s, 1H).

Referential Example 52

1-tert-Butyl-5-isobutylpyrazole-3-carbaldehyde

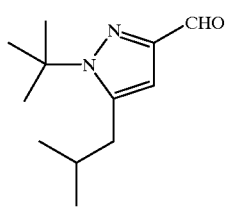

¹H-NMR (CDCl₃, 400 MHz) δ; 1.00(d,J=6.8 Hz,6H), 1.68(s,9H), 1.94–2.08(m,1H), 2.68(d,J=6.0 Hz,2H), 6.62(s,1H), 9.89(s,1H).

Referential Example 53

1,5-Diisopropylpyrazole-3-carbaldehyde

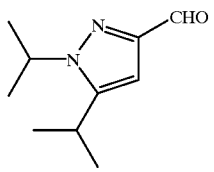

¹H-NMR (CDCl₃, 400 MHz) δ; 1.28(d,J=6.8Hz,6H), 1.53(d,J=6.8 Hz,6H), 2.95–3.04(m,1H), 4.50–4.58(m,1H), 6.58(s,1H), 9.90(s,1H).

Referential Example 54

1,5-Diisopropyl-4-methylpyrazole-3-carbaldehyde

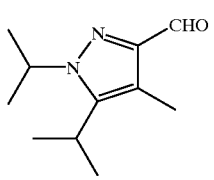

¹H-NMR (CDCl₃, 400 MHz) δ; 1.34(d,J=6.8 Hz,6H), 1.51(d,J=6.8 Hz,6H), 2.33(s,3H), 3.10–3.20(m,1H), 4.52–4.60(m,1H), 9.96(s,1H).

Referential Example 55

5Isoburtyl-1-isopropylpyrazole-3-carbaldehyde

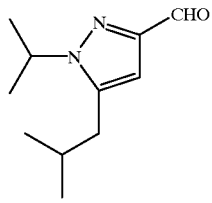

¹H-NMR (CDCl₃, 400 Hz) δ; 0.94(d,J=6.8 Hz,6H), 1.50(d,J=6.8 Hz,6H), 1.84–2.00(m,1H), 2.50(d,J=6.0 Hz,2H), 4.44–4.54(m,1H), 6.52(s,1H), 9.92(s,1H).

Referential Example 56

5-Isobutyl-1-isopropyl-4-methylpyrazole-3-carbaldehyde

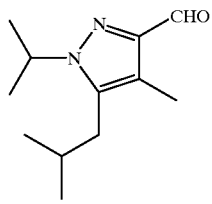

¹H-NMR (CDCl₃, 400 MHz) δ; 0.92(d,J=6.8 Hz,6H), 1.48(d,J=6.8 Hz,6H), 1.84–1.94(m,1H), 2.22(s,3H), 2.46(d, J=6.0 Hz,2H), 4.44–4.52(m,1H), 10.00(s,1H).

Referential Example 57

1-Ethyl-5- isopropylpyrazole-3-carbaldehyde

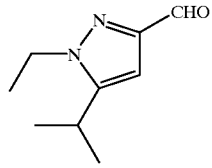

¹H-NMP (CDCl₃, 400 MHz) δ; 1.28(d,J=6.8 Hz,6H), 1.51(t,J=6.0 Hz,3H), 2.92–3.04(m,1H), 4.19(q,J=6.0 Hz,2H), 6.58(s,1H), 9.92(s,1H).

Referential Example 58

5-Isopropyl-1-propylpyrazole-3-carbaldehyde

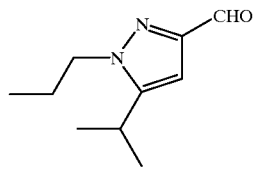

¹H-NMR (CDCl₃, 400 MHz) δ; 0.94(t,J=7.2 Hz,3H), 1.27(d,J==6.8 Hz,6H), 1.90–1.98(m,2H), 2.80–3.00(m,1H), 4.09(t,J=7.2 Hz,2H), 6.78(s,1H), 9.80(s,1H).

Referential Example 59

8-Isopropyl-4-(2-furyl)quinoxaline-2-carbaldehyde

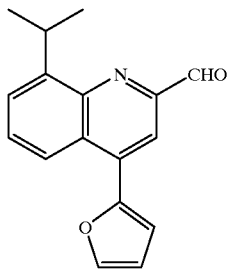

$^1$H-NMR (CDCl$_3$, 400 MHz) δ; 1.42(d,J=7.0 Hz,6H), 4.52(quint.,J=7.0 Hz,1H), 6.65(dd,J=2.0,3.6 Hz, 1H), 7.03 (dd,J=0.8,3.2 Hz,1H), 7.68(dd,J=7.6,8.0 Hz,1H),7.71(dd, J=0.8,1.6 Hz,1H), 7.73(dd,J=2.0,7.6 Hz,1H), 8.23(s,1H), 8.41(dd,J=1.6,8.4 Hz,1H), 10.24(s,1H).

What is claimed is:

1. A heterocycle-containing carboxylic acid derivative represented by the formula (I):

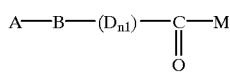

(I)

wherein A is a group represented by the following formula

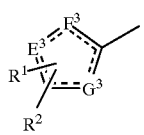

(iii)

in which E$^3$, F$^3$ and G$^3$ are the same or different and each independently represents an oxygen atom or a nitrogen, carbon or sulfur atom which may have a substituent with the proviso where in the ring (iii), E$^3$, F$^3$ and G$^3$ each represents a carbon group which may have a substituent are excluded; R$^1$ and R$^2$ are the same or different and each independently represents a hydrogen atom, a halogen atom, a lower alkyl group which may have a substituent, a cycloalkyl group which may have a substituent, a lower alkoxy group which may have a substituent, a cycloalkyloxy group which may have a substituent, an aryl group which may have a substituent, a heteroaryl group which may have a substituent, an aryloxy group which may have a substituent, a heteroaryloxy group which may have a substituent, a cycloalkylalkyl group which may have a substituent, an arylalkyl group which may have a substituent, a heteroarylalkyl group which may have a substituent, a cycloalkylalkyloxy group which have a substituent, an arylalkyloxy group which may have a substituent, a heteroarylalkyloxy group which may have a substituent, an alkenyl group which may have a substituent or an alkynyl group which may have a substituent, or R$^1$ and R$^2$ are coupled together to form a cycloalkylene group may have a substituent, a carbon group forming said cycloalkylene group which may be substituted by a sulfur atom, an oxygen atom, a sulfinyl group, a sulfonyl group or >NR$^4$, R$^4$ representing a hydrogen atom or a lower alkyl group;

B is a heteroarylene group which may have a substituent, an arylene group which may have a substituent, or a group represented by the following formula:

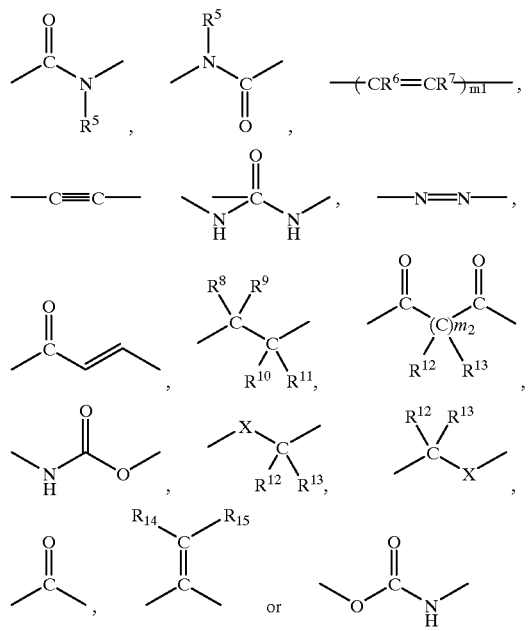

wherein R$^5$ represents a hydrogen atom or a lower alkyl group; R$^6$ and R$^7$ are the same or different and each independently represents a hydrogen atom, a lower alkyl group or a halogen atom and m1 stands for 1 to 3, m$_2$ stands for 0 to 2; R$^8$ to R$^{15}$ are the same or different and each independently represents a hydrogen atom or a lower alkyl group; X represents an oxygen atom, a sulfur atom or >NR$^4$, R$^4$ having the same meaning as defined above;

D is an arylene group which may have a substituent, a heteroarylene group which may have a substituent, or a group represented by the formula: —CR$^6$=CR$^7$—, R$^6$ and R$^7$ having the same meanings as defined above;

n$_1$ stands for 0 to 1;

M is a hydroxyl group, a lower alkoxy group or a group represented by the following formula: —NR$^{16}$R$^{17}$ in which R$^{16}$ and R$^{17}$ are the same or different and each independently represents a hydrogen atom, a hydroxyl group, a lower alkyl group, a lower alkoxy group, a hydroxyalkyl group, an aryl group or a heteroaryl group or R$^{16}$ and R$^{17}$ are coupled together with the adjacent nitrogen atom to form an oxygen- or sulfur-containing ring; and === represents a single bond or double bond; or a physiologically acceptable salt thereof provided that when B is CONH or NHCO and M is a hydroxyl group, n$_1$ is 0 or D is —CR$^6$=CR$^7$—, and further provided that when B is CONH or NCHO and M is a lower alkoxy group or a group of the formula NR$^{16}$R$^{17}$, n$_1$ is 0 or D is —CR$^6$=CR$^7$—.

2. A heterocycle-containing carboxylic acid derivative represented by the formula (I):

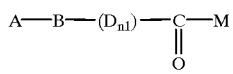

(I)

wherein A is a group represented by the following formula (iii)

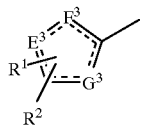

in which $E^3$, $F^3$ and $G^3$ are the same or different and each independently represents an oxygen atom or a nitrogen, carbon or sulfur atom which may have a substituent with the proviso where in the ring (iii), $E^3$, $F^3$ and $G^3$ each represents a carbon group which may have a substituent are excluded; $R^1$ and $R^2$ are the same or different and each independently represents a hydrogen atom, a halogen atom, a lower alkyl group which may have a substituent, a cycloalkyl group which may have a substituent, a lower alkoxy group which may have a substituent, a cycloalkyloxy group which may have a substituent, an aryl group which may have a substituent, a heteroaryl group which may have a substituent, an aryloxy group which may have a substituent, a heteroaryloxy group which may have a substituent, a cycloalkylalkyl group which may have a substituent, an arylalkyl group which may have a substituent, a heteroarylalkyl group which may have a substituent, a cycloalkylalkyloxy group which have a substituent, an arylalkyloxy group which may have a substituent, a heteroarylalkyloxy group which may have a substituent, an alkenyl group which may have a substituent or an alkynyl group which may have a substituent, or $R^1$ and $R^2$ are coupled together to form a cycloalkylene group may have a substituent, a carbon group forming said cycloalkylene group which may be substituted by a sulfur atom, an oxygen atom, a sulfinyl group, a sulfonyl group or >$NR^4$, $R^4$ representing a hydrogen atom or a lower alkyl group;

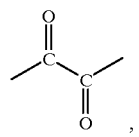

D is an arylene group which may have a substituent, a heteroarylene group which may have a substituent, or a group represented by the formula: —$CR^6$=$CR^7$—, $R^6$ and $R^7$ having the same meanings as defined above;
$n_1$ stands for 0 to 1;
M is a hydroxyl group, a lower alkoxy group or a group represented by the following formula: —$NR^{16}R^{17}$in which $R^{16}$ and $R^{17}$ are the same or different and each independently represents a hydrogen atom, a hydroxyl group, a lower alkyl group, a lower alkoxy group, a hydroxyalkyl group, an aryl group or a heteroaryl group or $R^{16}$ and $R^{17}$ are coupled together with the adjacent nitrogen atom to form an oxygen- or sulfur-containing ring; and === represents a single bond or double bond; or a physiologically acceptable salt thereof.

3. A heterocycle-containing carboxylic acid derivative represented by the formula (I):

(I)

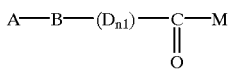

wherein A is a group represented by the following formula (iii)

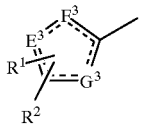

in which $E^3$, $F^3$ and $G^3$ are the same or different and each independently represents an oxygen atom or a nitrogen, carbon or sulfur atom which may have a substituent with the proviso where in the ring (iii), $E^3$, $F^3$ and $G^3$ each represents a carbon group which may have a substituent are excluded; $R^1$ and $R^1$ are the same or different and each independently represents a hydrogen atom, a halogen atom, a lower alkyl group which may have a substituent, a cycloalkyl group which may have a substituent, a lower alkoxy group which may have a substituent, a cycloalkyloxy group which may have a substituent, an aryl group which may have a substituent, a heteroaryl group which may have a substituent, an aryloxy group which may have a substituent, a heteroaryloxy group which may have a substituent, a cycloalkylalkyl group which may have a substituent, an arylalkyl group which may have a substituent, a heteroarylalkyl group which may have a substituent, a cycloalkylalkyloxy group which have a substituent, an arylalkyloxy group which may have a substituent, a heteroarylalkyloxy group which may have a substituent, an alkenyl group which may have a substituent or an alkynyl group which may have a substituent, or $R^1$ and $R^2$ are coupled together to form a cycloalkylene group may have a substituent, a carbon group forming said cycloalkylene group which may be substituted by a sulfur atom, an oxygen atom, a sulfinyl group, a sulfonyl group or >$NR^4$, $R^4$ representing a hydrogen atom or a lower alkyl group;
B is a heteroarylene group which may have a substituent, an arylene group which may have a substituent, or a group represented by the following formula:

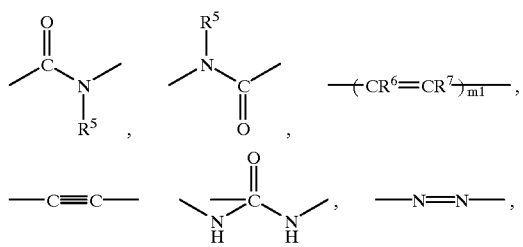

-continued

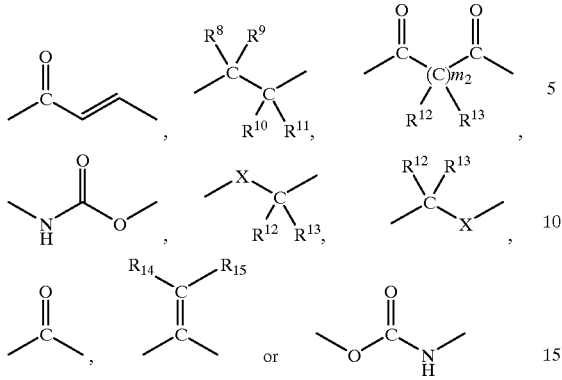

wherein $R^5$ represents a hydrogen atom or a lower alkyl group; $R^6$ and $R^7$ are the same or different and each independently represents a hydrogen atom, a lower alkyl group or a halogen atom and m1 stands for 1 to 3, ma stands for 0 to 2; $R^8$ to $R^{15}$ are the same or different and each independently represents a hydrogen atom or a lower alkyl group; X represents an oxygen atom, a sulfur atom or >$NR^4$, $R^4$ having the same meaning as defined above;

D is a group represented by the formula: —$CR^6$=$CR^7$—, $R^6$ and $R^7$ having the same meanings as defined above;

$n_1$ stands for 0 to 1;

M is a hydroxyl group, a lower alkoxy group or a group represented by the following formula: —$NR^{16}R^{17}$ in which $R^{16}$ and $R^{17}$ are the same or different and each independently represents a hydrogen atom, a hydroxyl group, a lower alkyl group, a lower alkoxy group, a hydroxyalkyl group, an aryl group or a heteroaryl group or $R^{16}$ and $R^{17}$ are coupled together with the adjacent nitrogen atom to form an oxygen- or sulfur-containing ring; and ═══ represents a single bond or double bond; or a physiologically acceptable salt thereof.

4. The compound 4-{2-{5-[3-(5-isobutyl-1-isopropylpyrazolyl)] pyrrolyl}}benzoic acid.

5. A pharmaceutical composition comprising a pharmaceutically effective amount of the heterocycle-containing carboxylic acid derivative or physiologically acceptable salt thereof as claimed in claim 1, 2 or 3 and a pharmaceutically acceptable carrier.

6. A method for treating acute promyelocytic leukemia by administering a pharmaceutically effective dose of the heterocycle-containing carboxylic acid derivative or physiologically acceptable salt thereof as claimed in claim 1, 2 or 3 to a person suffering from acute promyelocytic leukemia.

* * * * *